United States Patent
Dewhurst et al.

(10) Patent No.: US 8,961,977 B2
(45) Date of Patent: Feb. 24, 2015

(54) ANTIGENIC MIMICS OF DISCONTINUOUS EPITOPES OF PATHOGEN RECOGNIZED BY BROADLY NEUTRALIZING ANTIBODIES

(75) Inventors: Stephen Dewhurst, Rochester, NY (US); Mark A. Sullivan, Fairport, NY (US)

(73) Assignee: University of Rochester, Rochester, NY (US)

(*) Notice: Subject to any disclaimer, the term of this patent is extended or adjusted under 35 U.S.C. 154(b) by 1 day.

(21) Appl. No.: 13/577,419

(22) PCT Filed: Feb. 14, 2011

(86) PCT No.: PCT/US2011/024777
§ 371 (c)(1),
(2), (4) Date: Oct. 23, 2012

(87) PCT Pub. No.: WO2011/100700
PCT Pub. Date: Aug. 18, 2011

(65) Prior Publication Data
US 2013/0039927 A1    Feb. 14, 2013

Related U.S. Application Data

(60) Provisional application No. 61/304,093, filed on Feb. 12, 2010, provisional application No. 61/327,317, filed on Apr. 23, 2010.

(51) Int. Cl.
| | | |
|---|---|---|
| C07K 14/78 | (2006.01) | |
| C07K 14/18 | (2006.01) | |
| C12N 15/12 | (2006.01) | |
| C12N 15/63 | (2006.01) | |
| C12N 1/21 | (2006.01) | |
| C12N 5/10 | (2006.01) | |
| C12N 1/13 | (2006.01) | |
| A61K 39/00 | (2006.01) | |
| A61K 39/12 | (2006.01) | |
| A61K 39/21 | (2006.01) | |

(52) U.S. Cl.
CPC ......... *A61K 39/21* (2013.01); *A61K 2039/6031* (2013.01); *A61K 2039/6075* (2013.01); *A61K 2039/64* (2013.01)
USPC .................. 424/159.1; 424/164.1; 424/172.1; 424/184.1; 424/204.1; 424/234.1; 435/252.3; 435/252.34; 435/254.11; 435/254.2; 435/257.2; 435/320.1; 435/325; 435/348; 435/352; 435/362; 435/365; 435/367; 435/419; 435/7.92; 435/7.93

(58) Field of Classification Search
CPC .............. A61K 2039/6056; A61K 2039/6075; A61K 38/363; A61K 39/12; C07K 16/00; A61L 2300/256; A61L 24/106; A61L 26/0042
See application file for complete search history.

(56) References Cited

U.S. PATENT DOCUMENTS

| | | | | |
|---|---|---|---|---|
| 7,598,352 | B2 * | 10/2009 | Koide | 530/388.9 |
| 7,939,083 | B2 * | 5/2011 | Dey et al. | 424/208.1 |
| 8,263,350 | B2 * | 9/2012 | Koide et al. | 435/7.1 |
| 2002/0019517 | A1 * | 2/2002 | Koide | 530/387.1 |
| 2003/0186385 | A1 * | 10/2003 | Koide | 435/69.7 |
| 2007/0117966 | A1 | 5/2007 | Koide et al. | |

FOREIGN PATENT DOCUMENTS

| | | |
|---|---|---|
| WO | 2007144771 A2 | 12/2007 |
| WO | 2008143679 A2 | 11/2008 |

OTHER PUBLICATIONS

Koide A, Koide S. Monobodies: antibody mimics based on the scaffold of the fibronectin type III domain. Methods Mol Biol. 2007;352:95-109.*
Koide A, Bailey CW, Huang X, Koide S. The fibronectin type III domain as a scaffold for novel binding proteins. J Mol Biol. Dec. 11, 1998;284(4)1141-51.*
Batori V, Koide A, Koide S. Exploring the potential of the monobody scaffold: effects of loop elongation on the stability of a fibronectin type III domain. Protein Eng. Dec. 2002;15(12):1015-20.*
Sullivan MA, Brooks LR, Weidenborner P, Domm W, Mattiacio J, Xu Q, Tiberio M, Wentworth T, Kobie J, Bryk P, Zheng B, Murphy M, Sanz I, Dewhurst S. Anti-idiotypic monobodies derived from a fibronectin scaffold. Biochemistry. Mar. 12, 2013;52(10):1802-13. Epub Mar. 1, 2013.*
Desrosiers RC. Prospects for an AIDS vaccine. Nat Med. Mar. 2004;10(3):221-3.*
Matthews TJ, Lyerly HK, Weinhold KJ, Langlois AJ, Rusche J, Putney SD, GalloRC, Bolognesi DP. Prospects for development of a vaccine against HTLV-III-related disorders. AIDS Res Hum Retroviruses. 1987;3 Suppl 1:197-206.*
Burton et al. 'HIV Vaccine Design and the Neutralizing Antibody Problem,' Nat. Immunol. 5(3):233-236 (2004).
Burioni et al. 'Anti-HIV-1 Response Elicited in Rabbits by Anti-Idiotype Monoclonal Antibodies Mimicking the CD4-binding Site,' PLoS One 3(10):33423 (2008).
Zwick et al. 'Identification and Characterization of a Peptide that Specifically Binds the Human, Broadly Neutralizing Anti-human Immunodeficiency Virus Type 1 Antibody B12,' J. Virol 75(14):6692-6699 (2001).
Kwong et al., "HIV-1 and Influenza Antibodies: Seeing Antigens in New Ways," Nat. Immunol. 10(6):573-578 (2009).

(Continued)

*Primary Examiner* — Benjamin P Blumel
*Assistant Examiner* — Rachel Gill
(74) *Attorney, Agent, or Firm* — LeClairRyan, a Professional Corporation

(57) ABSTRACT

The present invention relates to an anti-idiotypic polypeptide scaffold that includes two or more peptide sequences that mimic a discontinuous epitope of a pathogen that is recognized by or induces formation of a broadly neutralizing antibody. Using a fibronectin FNfn10 scaffold bearing two or more modified discontinuous loops, scaffolds that recognize broadly neutralizing antibodies in vitro and from patient serum have been identified. These scaffolds should induce an immune response or mobilize germline specificities to initiate their affinity maturation.

17 Claims, 11 Drawing Sheets

(56) References Cited

OTHER PUBLICATIONS

Ekiert et al., "Antibody Recognition of a Highly Conserved Influenza Virus Epitope," Science 324:246-251 (2009).
Sui et al., "Structural and Functional Bases for Broad-Spectrum Neutralization of Avian and Human Influenza A Viruses," Nat. Struct. Mol. Biol. 1-9 (2009).
Thomson et al., "Germline V-Genes Sculpt the Binding Site of a Family of Antibodies Neutralizing Human Cytomegalovirus," EMBO J. 27:2592-2602 (2008).
McLean et al., "Recognition of Human Cytomegalovirus by Human Primary Immunoglobulins Identifies an Innate Foundation to an Adaptive Immune Response," J. Immunol. 174:4768-4778 (2005).
Zhou et al., "Structural Basis for Broad and Potent Neutralization of HIV-1 by Antibody VRC01," Science 329:811-817 (2010).
Wu et al., "Rational Design of Envelope Identifies Broadly Neutralizing Human Monoclonal Antibodies to HIV-1," Science 329(5993):856-861 (2010).

* cited by examiner

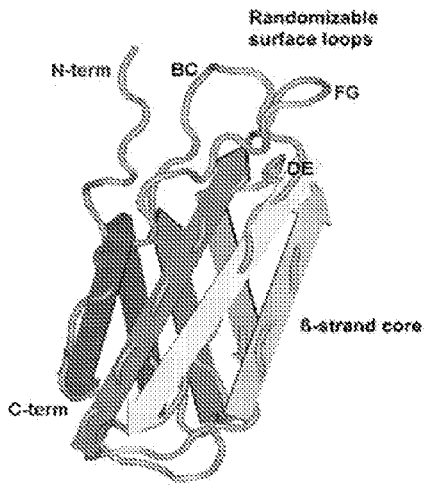

| Library | Size | Potential Amino Acids Encoded |
|---------|------|-------------------------------|
| Lib1 (KMT) | ~1 x 10⁷ | Tyr, Ser, Asp, Ala |
| Lib2 (NHK) | ~4 x 10⁷ | Tyr, Ser, Asp, Ala, Glu, Phe, Leu, Asn, Thr, Ile, Lys, Pro, His, Gln, Val, Met |
| Trimer | ~1 x 10⁹ | All amino acids except Cys |
| Trimer C | ~2 x 10⁸ | As Trimer, but containing a Cys-Cys disulfide bond between the BC and FG loops |

FIG. 1A                                          FIG. 1B

VSDVPRDLEVVAATPTSLLISWDAPAVTVRYYRITYGETGGNSPVQEFTVPGSKSTAT
ISGLKPGVDYTITVYAVTGRGDSPASSKPISINYRTGKKGK

FIG. 1C

```
FNfn10           VSDVPRDLEVVAATPTSLLISWDAPAVTVRYYRITYGETGGNSPVQEFTVPGSKSTATIS  60
XP_001083548_aa  VSDVPRDLEVVAATPTSLLISWDAPAVTVRYYRITYGETGGNSPVQEFTVPGSKSTATIS  60
XP_516072_aa     VSDVPRDLEVVAATPTSLLISWDAPAVTVRYYRITYGETGGNSPVQEFTVPGSKSTATIS  60
XP_001489154_aa  VSDVPRDLEVIATTPTSILISWDAPAVTVRYYRITYGETGGNSPVQEFTVPGSKSTATIS  60
NP_001157250_aa  VSDVPRDLEVIAATPTSLLISWDAPAVTVRYYRITYGETGGSSPVQEFTVPGSKSTATIS  60
XP_536059_aa     VSDVPRDLEVIAATPTSLLISWDAPAVTVRYYRITYGETGGNSPVQEFTVPGSKSTATIS  60
XP_001509150_aa  VSDVPRDLEIIATTPTSLLINWEAPAVTVRYYRITYGETGGTSPVQEFTVPGTKSSATIS  60
AAI45272_aa      VSDIPRDLEVIASTPTSLLISWEPPAVSVRYYRITYGETGGNSPVQEFTVPGSKSTATIN  60
EDL75263_aa      VSDVPRDLEVIASTPTSLLISWEPPAVSVRYYRITYGETGGNSPVQEFTVPGSKSTATIN  60
                 ***:******::*:****:**.*:.***:*************.***********:**:***.

FNfn10           GLKPGVDYTITVYAVTGRGDSPASSKPISINYRT  94
XP_001083548_aa  GLKPGVDYTITVYAVTGRGDSPASSKPISINYRT  94
XP_516072_aa     GLKPGVDYTITVYAVTGRGDSPASSKPISINYRT  94
XP_001489154_aa  GLKPGVDYTITVYAVTGRGDSPASSKPISIDYRT  94
NP_001157250_aa  GLKPGVDYTITVYAVTGRGDSPASSKPVSINYRT  94
XP_536059_aa     GLKPGADYTITVYAVTGRGDSPASSKPVSIDYRT  94
XP_001509150_aa  GLKPGADYIITVYAVTGRGDSPASSKPVSITYRT  94
AAI45272_aa      NIKPGADYTITLYAVTGRGDSPASSKPVSINYKT  94
EDL75263_aa      NIKPGADYTITLYAVTGRGDSPASSKPVSINYQT  94
                 .:***.** **:*****************:** *:*
```

FIG. 1D

|  | CDR1 |  | CDR2 |  |
|---|---|---|---|---|
|  | 27 28 29 30 31 32 |  | 51 52 52A 53 54 55 56 |  |
| 1-69 | G T F S S Y | (SEQ ID NO:37) | I I P I F G T | (SEQ ID NO:38) |
| F10 | V T F S S F | (SEQ ID NO:39) | I S P M F G T | (SEQ ID NO:40) |
| D8 | G T F S A Y | (SEQ ID NO:41) | I I G M F G T | (SEQ ID NO:42) |
| A66 | G P F S M T | (SEQ ID NO:43) | I S P I F R T | (SEQ ID NO:44) |
| G17 | V T F S S Y | (SEQ ID NO:45) | I I G V F G V | (SEQ ID NO:46) |
| D7 | G I F N T N | (SEQ ID NO:47) | V I P L F R T | (SEQ ID NO:48) |
| CR6261 | G P F R S Y | (SEQ ID NO:49) | I I P I F G T | (SEQ ID NO:50) |

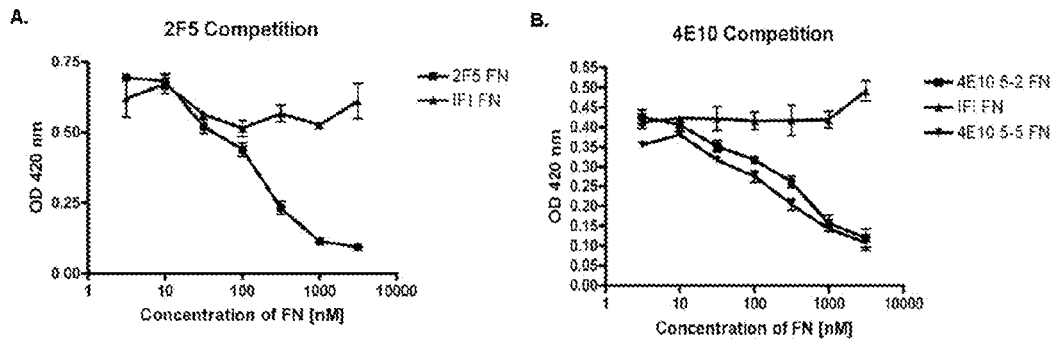
FIGS. 17A-B
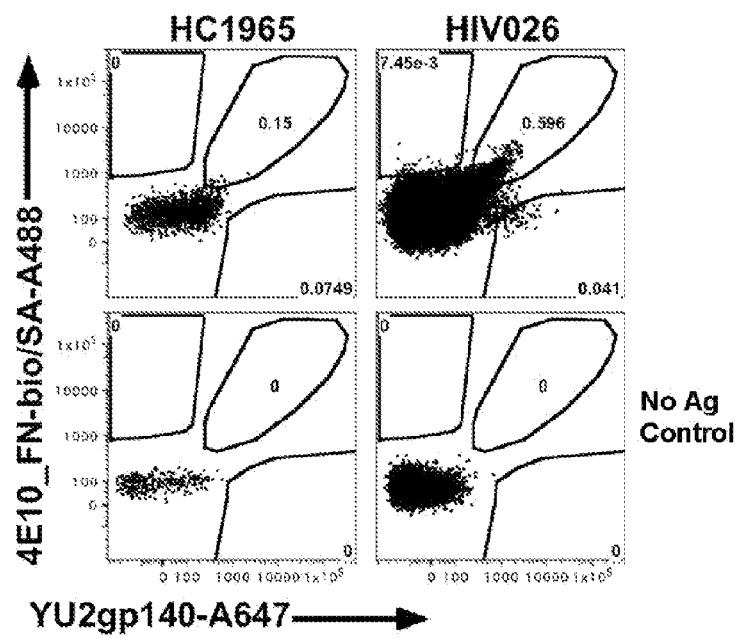
FIG. 18

VRC01GL
VRC01
M2 anti-Flag

US 8,961,977 B2

ANTIGENIC MIMICS OF DISCONTINUOUS EPITOPES OF PATHOGEN RECOGNIZED BY BROADLY NEUTRALIZING ANTIBODIES

This application is a national stage application under 35 U.S.C. §371 of PCT Application No. PCT/US2011/024777, filed Feb. 14, 2011, which claims priority benefit of U.S. Provisional Patent Application Ser. Nos. 61/304,093, filed Feb. 12, 2010, and 61/327,317, filed Apr. 23, 2010 which are hereby incorporated by reference in their entirety.

This invention was made with support from the National Institutes of Health under grants NIH R21 AI087149, N01AI70008-6-0-1, and TL1 RR024135. The U.S. government has certain rights in this invention.

FIELD OF THE INVENTION

The present invention relates generally to polypeptides, more particularly polypeptides derived from the tenth fibronectin type III domain from human fibronectin ("FNfn10"), fibronectin type III domain of human tenascin C, or domain III of flavivirus Env, which have activity in (i) binding to a neutralizing monoclonal antibody reactive to a pathogen (e.g., virus or bacteria), (ii) inducing a neutralizing immune response against the pathogen, (iii) binding to unmutated genomic antibody genes capable of directly neutralizing the infectivity of the pathogen, or (iv) binding to unmutated genomic antibody genes capable of giving rise to broadly neutralizing antibodies through somatic hypermutation. Encoding nucleic acid molecules, compositions containing the polypeptides or nucleic acid molecules, and antibodies raised against the polypeptides are also disclosed.

BACKGROUND OF THE INVENTION

The development of an effective vaccine for a number of viral and bacterial pathogens is a substantial unmet human health need. In particular, there is a need for human immunodeficiency virus type-1 (HIV-1) vaccine (Johnston et al., "An HIV Vaccine—Challenges and Prospects," *N Engl J Med.* 359(9):888-90 (2008), Barouch et al., "Challenges in the Development of an HIV-1 Vaccine," *Nature* 455(7213):613-9 (2008)). A major roadblock in this process is the present inability to elicit broadly neutralizing antibodies (BNA) that recognize the HIV-1 envelope, following immunization with candidate HIV-1 vaccines. This is believed to reflect, in part, the sequestration of key neutralizing epitopes on HIV-1 Env (Pantophlet, "GP120: Target for Neutralizing HIV-1 Antibodies," *Annu Rev Immunol.* 24:739-69 (2006); Walker, "Toward an AIDS Vaccine," *Science* 320(5877):760-4 (2008)).

The surface HIV-1 envelope glycoprotein subunit, gp120, is a major target for virus-neutralizing antibodies (Pantophlet, "GP120: Target for Neutralizing HIV-1 Antibodies," *Annu Rev Immunol.* 24:739-69 (2006)), but immunization with recombinant gp120 failed to elicit broadly neutralizing antibodies and failed to demonstrate protective efficacy in a Phase III clinical trial (Gilbert et al., "HIV-1 Virologic and Immunologic Progression and Initiation of Antiretroviral Therapy Among HIV-1-infected Subjects in a Trial of the Efficacy of Recombinant Glycoprotein 120 Vaccine," *J Infect Dis.* 192 (6):974-83 (2005); Gilbert et al., "Correlation Between Immunologic Responses to a Recombinant Glycoprotein 120 Vaccine and Incidence of HIV-1 Infection in a Phase 3 HIV-1 Preventive Vaccine Trial," *J Infect Dis.* 191(5):666-77 (2005)). Other approaches have attempted to use more native (oligomeric) forms of the envelope spike and/or re-engineered forms of the HIV-1 envelope, designed to display otherwise sequestered domains that may serve as targets for BNA. However, these approaches have yet to elicit the desired antibody response (Herrera et al., "The Impact of Envelope Glycoprotein Cleavage on the Antigenicity, Infectivity, and Neutralization Sensitivity of Env-pseudotyped Human Immunodeficiency Virus Type 1 Particles," *Virology* 338(1):154-72 (2005) and Poignard et al., "Heterogeneity of Envelope Molecules Expressed on Primary Human Immunodeficiency Virus Type 1 Particles as Probed by the Binding of Neutralizing and Normeutralizing Antibodies," *J Virol.* 77(1):353-65 (2003)).

HIV-1 Env presents a recalcitrant antigenic target in part because of the extensive glycosylation that hides antibody epitopes, and also because conserved domains which can serve as potential targets for broadly neutralizing antibodies are either physically sequestered or represent transient conformational intermediates (Wei et al., "Antibody Neutralization and Escape by HIV-1," *Nature* 422(6929):307-12 (2003); Wyatt et al., "The Antigenic Structure of the HIV gp120 Envelope Glycoprotein," *Nature* 393(6686):705-11 (1998); Rizzuto et al., "A Conserved HIV gp120 Glycoprotein Structure Involved in Chemokine Receptor Binding," *Science* 280 (5371):1949-53 (1998); and Kwong et al., "Structure of an HIV gp120 Envelope Glycoprotein in Complex with the CD4 Receptor and a Neutralizing Human Antibody," *Nature* 393 (6686):648-59 (1998), which are hereby incorporated by reference in their entirety). These considerations have led to attempts to rationally design improved Env immunogens that are better able to induce broadly neutralizing antibodies, and to create synthetic mimics of neutralizing antibody epitopes (Pantophlet, "GP120: Target for Neutralizing HIV-1 Antibodies," *Annu Rev Immunol.* 24:739-69 (2006); Saphire et al., "Crystal Structure of a Neutralizing Human IGG Against HIV-1: a Template for Vaccine Design," *Science* 293(5532):1155-9 (2001); Calarese et al., "Dissection of the Carbohydrate Specificity of the Broadly Neutralizing Anti-HIV-1 Antibody 2G12," *Proc Natl Acad Sci USA* 102(38):13372-7 (2005); Zwick et al., "Identification and Characterization of a Peptide that Specifically Binds the Human, Broadly Neutralizing Anti-human Immunodeficiency Virus Type 1 Antibody b12," *J Virol.* 75(14):6692-9 (2001); Ni et al., "Toward a Carbohydrate-based HIV-1 Vaccine: Synthesis and Immunological Studies of Oligomannose-containing Glycoconjugates," *Bioconjug Chem.* 17(2):493-500 (2006); Pashov et al., "Antigenic Properties of Peptide Mimotopes of HIV-1-associated Carbohydrate Antigens," *J Biol Chem.* 280(32):28959-65 (2005); Pashov et al., "Multiple Antigenic Mimotopes of HIV Carbohydrate Antigens—relating Structure and Antigenicity," *J Biol Chem.* (281): 29675-29683 (2006)). However, such an immunogen has not been developed.

There is also a need for new influenza virus vaccines to fight emerging avian influenza A viruses. The 2009 H1N1 influenza A virus (IAV) epidemic underscores the ability of antigenically novel IAV strains to rapidly infect human populations, creating the potential for a new viral pandemic. This same epidemic confirmed that conventional methods of generating the IAV vaccine are unsuitable for immediate response to the pathogen.

Highly pathogenic avian influenza A viruses that possess a new H5 subtype of hemagglutinin have been linked to numerous instances of human transmission, resulting in severe disease or death (Beigel et al., "Avian Influenza A (H5N1) Infection in Humans," *N. Engl. J. Med.* 353:1374-85 (2005); Tran et al., "Avian Influenza A (H5N1) in 10 Patients in Vietnam," *N. Engl. J. Med.* 350:1179-88 (2004)). There is considerable concern with regard to the pandemic potential of these viruses, due to the lack of H5-specific immunity in human populations and the widespread presence of virus in bird populations throughout Asia, Africa and Europe (Li et al., "Genesis of a Highly Pathogenic and Potentially Pandemic H5N1 Influenza Virus in Eastern Asia," *Nature* 430:209-13 (2004); Olsen et al., "Global Patterns of Influenza a Virus in Wild Birds," *Science* 312:384-8 (2006)). Moreover, resistance of these strains to existing antiviral drugs such as oseltamivir has been described (de Jong et al., "Oseltamivir Resistance During Treatment of Influenza A (H5N1) Infection," *N. Engl. J. Med.* 353:2667-72 (2005)). While human-to-human transmission of these highly pathogenic avian influenza virus strains appears to be rare (Ungchusak et al., "Probable Person-to-Person Transmission of Avian Influenza A (H5N1),"*N Engl J Med* 352:333-40 (2005)), there is a pressing need to develop new vaccines against influenza A (H5N1) virus.

Human clinical trials have shown that baculovirus-expressed recombinant hemagglutinins (rHA) can elicit serum antibody responses in both healthy and elderly adults (Lakey et al., "Recombinant Baculovirus Influenza A Hemagglutinin Vaccines Are Well Tolerated and Immunogenic in Healthy Adults," *J. Infect. Dis.* 174:838-41 (1996); Treanor et al., "Evaluation of a Recombinant Hemagglutinin Expressed in Insect Cells as an Influenza Vaccine in Young and Elderly Adults," *J. Infect. Dis.* 173:1467-70 (1996); Treanor et al., "Dose-Related Safety and Immunogenicity of a Trivalent Baculovirus-Expressed Influenza-Virus Hemagglutinin Vaccine in Elderly Adults," *J. Infect. Dis.* 193:1223-8 (2006); Treanor et al., "Safety and Immunogenicity of a Recombinant Hemagglutinin Vaccine for H5 Influenza in Humans," *Vaccine* 19:1732-7 (2001)). However, because the HA is administered as a soluble protein without adjuvant, relatively high doses have been required to achieve protective immunity; this has been a particular problem for the H5 rHA (Treanor et al., "Safety and Immunogenicity of a Recombinant Hemagglutinin Vaccine for H5 Influenza in Humans," *Vaccine* 19:1732-7 (2001)), as well as for egg-derived H5 vaccines in humans (Treanor et al., "Safety and Immunogenicity of an Inactivated Subvirion Influenza A (H5N1) Vaccine," *N. Engl. J. Med.* 354:1343-51 (2006)). Moreover, current data suggest that alum, the most widely available adjuvant for vaccines in humans, will not have a significant dose-sparing effect for H5 vaccines in man (Bresson et al., "Safety and Immunogenicity of an Inactivated Split-Virion Influenza A/Vietnam/1194/2004 (H5N1) Vaccine: Phase I Randomized Trial," Lancet: published online May 11, 2006 DOI:10.1016/S0140-6736 (06)68656-X (2006); Powers et al., "Influenza A Virus Vaccines Containing Purified Recombinant H3 Hemagglutinin Are Well Tolerated and Induce Protective Immune Responses in Healthy Adults," *J. Infect. Dis.* 171:1595-9 (1995)).

An inactivated subvirion vaccine developed by Sanofi has recently been evaluated in a human clinical trial. This product induces protective antibody levels in only 45% of recipients, even when used at a high dose, but was nonetheless recently recommended for licensure by VRBPAC as a "stop-gap" measure. This underscores the need to develop alternative approaches to increase the immunogenicity of H5 vaccines, and decrease the dose needed to achieve protective immunity—such that large-scale production will become feasible.

Monoclonal antibodies with broadly-neutralizing (BN) activity against group 1 influenza viruses have recently been identified, and shown to react against a conserved conformational epitope located in the stem of the hemagglutinin (HA) ectodomain, thereby preventing membrane fusion. Broad spectrum antibodies of this type are not, however, generated during influenza virus infection or immunization in humans. This is thought to be a consequence of an immunodominant response to the exposed globular head domain of HA.

It would be desirable, therefore, to generate an antigenic mimic of discontinuous pathogen epitopes that are recognized by broadly neutralizing antibodies, and which can be directly administered to an individual to induce an immune response against the pathogen of interest, or to bind to unmutated genomic antibody genes capable of either directly neutralizing the infectivity of a pathogen of interest or giving rise to broadly neutralizing antibodies.

The present invention overcomes these and other deficiencies in the art.

SUMMARY OF THE INVENTION

A first aspect of the present invention relates to an anti-idiotypic polypeptide scaffold that includes two or more peptide sequences that mimic a discontinuous epitope of a pathogen that is recognized by or induces formation of a broadly neutralizing antibody.

According to one embodiment, the polypeptide is a fibronectin type III (Fn3) polypeptide including: at least two Fn3 β-strand domain sequences with a loop region sequence linked between adjacent β-strand domain sequences; and optionally, an N-terminal tail of at least about 2 amino acids, a C-terminal tail of at least about 2 amino acids, or both; wherein at least one loop region sequence, the N-terminal tail, or the C-terminal tail comprises an amino acid sequence which varies by deletion, insertion, or replacement of at least two amino acids from a corresponding loop region, N-terminal tail, or C-terminal tail in a wild-type Fn3 domain of fibronectin, and wherein the polypeptide is an antigenic mimic of a pathogen (e.g., viral or bacterial) neutralizing epitope.

According to further embodiment, the polypeptide comprises β-strand domain sequences A, B, C, D, E, F, and G of a wild-type mammalian Fn3 domain of fibronectin with loop region sequences AB, BC, CD, DE, EF, and FG linked between adjacent β-strand domain sequences. The polypeptide also optionally includes an N-terminal tail of at least about 2 amino acids, a C-terminal tail of at least about 2 amino acids, or both. At least one loop region sequence of the polypeptide comprises a modified amino acid sequence which varies by deletion, insertion, or replacement of at least two amino acids from a corresponding loop region in the wild-type mammalian Fn3 domain of fibronectin, and the polypeptide either (i) binds specifically to a neutralizing monoclonal antibody reactive to a pathogen (e.g., virus or bacteria), (ii) induces a neutralizing immune response against the pathogen, (iii) binds to unmutated genomic antibody genes capable of directly neutralizing the infectivity of the pathogen, or (iv) binds to unmutated genomic antibody genes capable of giving rise to broadly neutralizing antibodies through somatic hypermutation.

A second aspect of the present invention relates to a nucleic acid molecule encoding a polypeptide of the present invention.

A third aspect of the present invention relates to a DNA construct which includes a DNA molecule encoding a polypeptide of the present invention, a promoter-effective DNA molecule operably coupled 5' of the DNA molecule, and a transcription termination DNA molecule operably coupled 3' of the DNA molecule.

A fourth aspect of the present invention relates to an expression vector into which is inserted a DNA construct according to the present invention.

A fifth aspect of the present invention relates to a host cell transformed with a DNA construct or nucleic acid molecule according to the present invention.

A sixth aspect of the present invention relates to a composition comprising a pharmaceutically acceptable carrier and a polypeptide according to the present invention.

A seventh aspect of the present invention relates to a vaccine comprising a pharmaceutically acceptable carrier and either a polypeptide according to the present invention, a DNA molecule according to the present invention, an expression vector according to the present invention, or a combination thereof.

An eighth aspect of the present invention relates to a method of imparting resistance to viral or bacterial infection comprising administration of a vaccine according to the present invention to a mammal under conditions effective to induce a protective immune response against the virus or bacteria.

A ninth aspect of the present invention relates to an isolated antibody raised against a polypeptide according to the present invention, or a binding fragment thereof.

A tenth aspect of the present invention relates to a pharmaceutical composition comprising a pharmaceutically acceptable carrier and an antibody, or a binding fragment thereof, according to the present invention.

An eleventh aspect of the present invention relates to a method of treating a viral or bacterial infection comprising administering to a patient an antibody or fragment thereof according to the present invention, or a pharmaceutical composition according to the present invention, under conditions effective to neutralize the virus or bacteria, and thereby treat the viral or bacterial infection.

A twelfth aspect of the present invention relates to a method for inducing a neutralizing antibody response in a subject. The method comprises the steps of providing a subject in need of a neutralizing antibody response and administering a vaccine according to the present invention in a manner effective to induce a neutralizing antibody response.

A thirteenth aspect of the present invention relates to an assay for detecting reactivity between a polypeptide of the present invention and a broadly neutralizing antibody. The assay includes contacting the polypeptide with the broadly neutralizing antibody, and determining whether the broadly neutralizing antibody binds specifically to the polypeptide. This can be achieved using a labeled polypeptide or a labeled broadly neutralizing antibody.

A fourteenth aspect of the present invention relates to a method for detecting a neutralizing antibody in serum. The method comprises providing a polypeptide according to the present invention comprising a label, contacting the labeled polypeptide with serum from an individual, and detecting whether the polypeptide binds specifically to an antibody present in the serum, where the detecting is carried out using the label.

Several lines of evidence suggest that, if an appropriate immunogen were available, HIV-1 specific BNA could be elicited. First, a small number of monoclonal antibodies (Mab) have been identified that possess neutralizing activity against a wide range of HIV-1 strains, including primary isolates (Pantophlet, "GP120: Target for Neutralizing HIV-1 Antibodies," *Annu. Rev. Immunol.* 24:739-69 (2006), which is hereby incorporated by reference in its entirety). Perhaps the best characterized of these is Mab b12, which recognizes a discontinuous epitope within the CD4 binding site of the HIV-1 envelope (Burton et al., "A Large Array of Human Monoclonal Antibodies to Type 1 Human Immunodeficiency Virus from Combinatorial Libraries of Asymptomatic Seropositive Individuals," *Proc Natl Acad Sci USA* 88(22):10134-7 (1991); Burton et al., "Efficient Neutralization of Primary Isolates of HIV-1 By a Recombinant Human Monoclonal Antibody," *Science* 266(5187):1024-7 (1994), which are hereby incorporated by reference in their entirety). Second, a number of HIV-1 infected subjects make broadly neutralizing antibody responses (Scheid et al., "Broad Diversity of Neutralizing Antibodies Isolated From Memory B Cells in HIV-infected Individuals," *Nature* 458(7238):636-40 (2009); Li et al., "Analysis of Neutralization Specificities in Polyclonal Sera Derived from Human Immunodeficiency Virus Type 1-infected Individuals," *J Virol.* 83(2):1045-59 (2009); Gray et al., "Antibody Specificities Associated with Neutralization Breadth in Plasma from Human Immunodeficiency Virus Type 1 Subtype C-infected Blood Donors," *J Virol.* 83(17): 8925-37 (2009); Binley et al., "Profiling the Specificity of Neutralizing Antibodies in a Large Panel of Plasmas from Patients Chronically Infected with Human Immunodeficiency Virus Type 1 Subtypes B and C," *J Virol.* 82(23): 11651-68 (2008); Pantophlet, "GP120: Target for Neutralizing HIV-1 Antibodies," *Annu Rev Immunol.* 24:739-69 (2006), which are hereby incorporated by reference in their entirety). Finally, in many cases, the broad virus-neutralizing activity present in these rare patient sera can be attributed to "b12-like" antibodies that recognize the CD4 binding site in the HIV-1 envelope (Li et al., "Analysis of Neutralization Specificities in Polyclonal Sera Derived from Human Immunodeficiency Virus Type-1 Infected Individuals," *J. Virol.* 83(2):1045-59 (2008), which is hereby incorporated by reference in its entirety).

One way of solving the problem of epitope sequestration on HIV-1 Env is to develop antigenic mimics of sequestered, conformational epitopes on HIV-1 Env, which can then be used as immunogens to elicit BNA. Previous attempts to derive antigenic mimics of the Env epitope recognized by Mab b12 have been unsuccessful, despite the identification of two linear peptides that bind with high affinity to the b12 Mab (Dorgham et al., "Immunogenicity of HIV Type 1 gp120 CD4 Binding Site Phage Mimotopes," *AIDS Res Hum Retroviruses* 21(1):82-92 (2005), which is hereby incorporated by reference in its entirety). The lack of antigenic mimicry between these Mab b12-binding peptides and the native Env epitope recognized by Mab b12 has been attributed to the fact that the authentic gp120 epitope bound by b12 is discontinuous—unlike the peptide mimotopes (Saphire et al., "Structure of a High-affinity "Mimotope" Peptide Bound to HIV-1-Neutralizing Antibody b12 Explains its Inability to Elicit gp120 Cross-reactive Antibodies," *J Mol Biol.* 369(3):696-709 (2007), which is hereby incorporated by reference in its entirety).

As described infra, an innovative solution to this problem relates to exploiting a unique molecular scaffold that can be diversified in up to three discontinuous, but interacting, surface exposed loops (Koide et al., "Monobodies: Antibody Mimics Based on the Scaffold of the Fibronectin Type III Domain," *Methods Mol Biol.* 352:95-109 (2007), which is hereby incorporated by reference in its entirety). This is fundamentally different from conventional phage display peptide libraries, which are diversified only a single continuous peptide domain and, thus, ill-suited for the identification of antigenic mimics of discontinuous epitopes (Scott et al., "Searching for Peptide Ligands with an Epitope Library," *Science* 249(4967):386-90 (1990); Smith et al., "Libraries of Peptides and Proteins Displayed on Filamentous Phage," *Methods Enzymol.* 217:228-57 (1993), which are hereby incorporated by reference in their entirety).

This innovative approach can also be used to identify other polypeptides that elicit BNA specific to, or that induce a neutralizing immune response to, other viruses or bacteria. Thus, this approach is not limited to HIV-1. In particular, antigenic mimics (or polypeptides) of other neutralizing epitopes are included (Scheid et al., "Broad Diversity of Neutralizing Antibodies Isolated From Memory B Cells in HIV-infected Individuals," *Nature* 458(7238):636-40 (2009); Li et al., "Analysis of Neutralization Specificities in Polyclonal Sera Derived from Human Immunodeficiency Virus Type 1-infected Individuals," *J Virol.* 83(2):1045-59 (2009); Gray et al., "Antibody Specificities Associated with Neutralization Breadth in Plasma from Human Immunodeficiency Virus Type 1 Subtype C-infected Blood Donors," *J Virol.* 83(17): 8925-37 (2009); Binley et al., "Profiling the Specificity of Neutralizing Antibodies in a Large Panel of Plasmas from Patients Chronically Infected with Human Immunodeficiency Virus Type 1 Subtypes B and C," *J Virol.* 82(23): 11651-68 (2008), which are hereby incorporated by reference in their entirety)—including conformational epitopes on Env trimers (Walker et al., "Broad and Potent Neutralizing Antibodies from an African Donor Reveal a New HIV-1 Vaccine Target," *Science* 326(5950):285-9 (2009), which is hereby incorporated by reference in its entirety), as well as epitopes derived from the glycan shield of the envelope (Hessell et al., "Broadly Neutralizing Human Anti-HIV Antibody 2G12 is Effective in Protection Against Mucosal SHIV Challenge Even at Low Serum neutralizing Titers," *PLOS Pathog.* 5(5): e1000433 (2009), which is hereby incorporated by reference in its entirety).

For example, monoclonal antibodies with broadly-neutralizing (BN) activity against group 1 influenza viruses have recently been identified, and shown to react against a conserved conformational epitope located in the stem of the hemagglutinin (HA) ectodomain, thereby preventing membrane fusion. Broad spectrum antibodies of this type are not, however, generated during influenza virus infection or immunization in humans. This is thought to be a consequence of an immunodominant response to the exposed globular head domain of HA. One way of overcoming this problem is to develop antigenic mimics of this broadly neutralizing epitope, which can then be used as immunogens to elicit BN antibodies. Such immunogens will have considerable value as part of a pre-pandemic vaccine, intended to elicit protective immunity to a broad range of emerging influenza A viruses (IAV), including H5N1 viruses and the 2009 H1N1 virus. Thus, by exploiting a unique molecular scaffold that can be diversified in up to three discontinuous, but interacting, surface exposed loops, antigenic mimics of conformational HA epitopes (such as this broadly neutralizing "fusion pocket" epitope) can be identified. These antigenic mimics can then be used to elicit broadly neutralizing antibodies against influenza viruses, with reactivity to multiple virus strains—including the 2009 H1N1 influenza A virus and emerging H5N1 viruses.

As demonstrated in the accompanying Examples, using routine screening procedures it is possible to identify polypeptides of the invention that bind specifically to broadly neutralizing antibodies of a pathogen. FNfn10 clones have been constructed with randomized BC and FG loops, which were then selected for binding to a panel of HIV-1 broadly neutralizing monoclonal antibodies (Mab) by phage display technology. This resulted in the generation of surrogates of both linear Mab epitopes (2F5 and 4E10 Mab) and of conformational Mab epitopes (b12 Mab). Surrogates of linear Mab epitopes frequently displayed sequence homology to the corresponding native epitopes; in contrast, surrogates of the conformational b12 epitope did not do so. Analysis of several of the b12 epitope surrogates revealed that they engage the b12 antibody via similar contact residues to HIV-1 Env, unlike the well characterized b12-binding B2.1 peptide. Representatives of the surrogates (b12, 2F5, and 4E10) were able to compete with native antigen for binding to their respective Mab. Finally, the 4E10 epitope surrogate reacted selectively with sera from HIV-1 infected subjects with detectable levels of virus-neutralizing antibodies, but not with sera from virus-negative controls.

Because these mimics of the present invention bind specifically to b12, competitively inhibit its binding to HIV-1 Env and contact the same antibody residues that are used to bind to HIV-1 Env, FNfn10 clones possessing these abilities should be useful as a vaccine to induce broadly neutralizing MAbs or promote germline progenitor expansion.

Further, accompanying Examples also demonstrate that FNfn10-derived anti-idiotype reagents can be used to selectively amplify specific B cell populations that represent the source of broadly-neutralizing antibodies ("bNab" or "Mab") directed against HIV-1 or other pathogens of interest, including influenza.

BRIEF DESCRIPTION OF THE DRAWINGS

FIG. 1A illustrates the FNfn10 molecular scaffold. β strands A-G of the FNfn10 molecular scaffold are shown, along with the 3 discontinuous surface exposed loops that can be randomized (BC, FG, and DE). The structure was generated using CN3D (source data file=MMDB IB 57520). FIG. 1B is a table of possible amino acids within libraries used to create variable BC and FG loops of the FNs (including those shown in Table 1, below). FIG. 1C shows the sequence of the mature FNfn10 protein (after proteolytic removal of the N-terminal MQ residues) (SEQ ID NO:1). The BC (Asp23-Val29) and FG (Gly77-Ser84) loops are in boldface. The DE loop is located from residues 52 thru 55. FIG. 1D is a CLUSTAL multiple sequence alignment for the tenth Fn3 domain of human (FNfn10) (SEQ ID NO:2), *Macaca mulatta* (accession no. XP_001083548 (aa 1662-1755) (SEQ ID NO:3)), *Pan troglodytes* (accession no. XP_516072 (aa 1748-1841) (SEQ ID NO:4)), *Bos Taurus* (accession no. NP_001157250 (aa 1446-1541) (SEQ ID NO:5)), *Canis familiaris* (accession no. XP_536059 (aa 1553-1646) (SEQ ID NO:6)), *Equus caballus* (accession no. XP_001489154 (aa 1538-1631) (SEQ ID NO:7)), *Mus musculus* (accession no. AAI45272 (aa 1446-1540) (SEQ ID NO:8)), *Rattus norvegicus* (accession no. EDL75263 (aa 1446-1540) (SEQ ID NO:9)), and *Ornithorhynchus anatinus* (accession no. XP_001509150 (aa 541-636) (SEQ ID NO:10)). The alignment shows the conservation of the β-strand domain sequences A, B, C, D, E, F, and G among mammals generally and, particularly, among the mammals shown.

FIG. 5 shows results from a competition ELISA assay that demonstrates oligomeric HIV-1 gp140 competitively inhibits binding of IgG1 b12 Mab to immobilized b12-FN-3-5. Purified, biotinylated protein corresponding to a representative b12 Mab-binding FNfn10 clone (b12-FN-3-5) was bound to streptavidin coated wells (Pierce), and washed 3× with PBS+ 0.05% Tween (PBS-T). Each condition was repeated in duplicate. Serial 2-fold dilutions of oligomeric HIV-1 gp 140 (YU-2) from 12.5 to 0.2 μg/ml were pre-incubated with a fixed amount of IgG1 b12 Mab (1:3000) at 37° C. for one hr, before being added to FN-b12-5 coated wells. The plate was incubated at RT for one hr, washed 5× with PBS-T and 50 μl per well of phosphatase substrate (KPL) was added. Absorbance was read at OD630. The results show that oligomeric HIV-1 gp140 (YU-2) competitively inhibits binding of the IgG1 b12 Mab to immobilized b12-FN-3-5 protein.

FIG. 6 shows kinetic analysis of binding of b12 3-5 FN to b12 Mab.

FIG. 7 shows the results of an ELISA assay. In particular, 2F5, 4E10 and F105 Mab binding clones were selected from the FNfn10 two loop display library. The FNfn10 two loop display library was selected against the immobilized Mabs indicated along the top of the Figure (b12, 4E10, 2F5, F105). Individual phage clones that were derived from this selection process were then tested for their ability to bind to the indicated immobilized HIV-1 Env specific Mabs or an irrelevant IgG1 Mab, using an ELISA assay (see left figure label). The phage ELISA was performed as described with reference to FIG. 3, supra. Phage clones were identified that bound specifically to each of the selecting Mabs, but not to unrelated/irrelevant Mabs (e.g., clone E3 for the 4E10 Mab, clones F1-F3 for the 2F5 Mab and clone FF11 for the F105 Mab, as well as several clones for the b12 Mab).

FIG. 8 illustrates the binding specificity of selected b12 mimotopes. Monoclonal antibodies were generated by cloning synthetic fragments encoding the variable regions of b12 and two single amino acid mutants (Y98A and Y53G in VH) into vectors for mammalian cell expression. Heavy and light chain plasmids were co-transfected into HEK293T cells and the medium was collected 72 hours later. Antibodies were purified on protein-G magnetic beads and coated at ~5 mg/ml. FN and the peptide mimotope B2.1 (positive control) phage (Zwick et al., "Identification and Characterization of a Peptide that Specifically Binds the Human, Broadly Neutralizing Anti-human Immunodeficiency Virus Type 1 Antibody b12," *J Virol.* 75(14):6692-9 (2001), which is hereby incorporated by reference in its entirety) were prepared by PEG precipitation from 1.2 ml cultures, re-suspended in 0.3 ml in TBS+ 0.5% casein and 50 μl was added to the wells. After 1 hour incubation at RT, the wells were washed 10 times and diluted anti-M13-HRP conjugate was added for 1 hour. After washing, HRP substrate (TMB) was added. FN-CRP1 and FN-CRP2 were used as negative controls.

FIG. 9 shows analysis of additional b12-binding clones from other peptide libraries. This shows that these clones bind to wild-type b12, but not to the Y98A, Y53G or W100A mutant antibodies.

FIG. 10A-B illustrate the binding specificity of b12 scFv and heavy chain point mutants for purified b12-FN-3-5bio protein. FIG. 10A shows a phage ELISA of the wt b12 and two point mutants, Y98A and W100A scFvs. The b12 antibody variable regions were cloned in a scFv format into the AP-III6 display vector as described in Haidaris et al., "Recombinant Human Antibody Single Chain Variable Fragments Reactive with *Candida Albicans* Surface Antigens," *J Immunol Methods* 257(1-2):185-202 (2001), which is hereby incorporated by reference in its entirety, and the VH mutations were introduced separately using site-directed mutagenesis. Phage preparations were diluted and applied to wells coated with gp140 trimer to measure antigen binding and anti-Flag Mab M2 to measure display of the scFvs. FIG. 10B shows the results after aliquots of each phage were applied to streptavidin-coated wells containing biotinylated b12-FN3-5 protein, and bound phage was detected with anti-M13-HRP.

FIG. 11 shows gel filtration profile and native gel analysis of YU2gp140 glycoprotein produced in 293-F cells. FreeStyle 293-F cells (Invitrogen) were transfected at a cell density of $1\times10^6$ cells per ml. Briefly, 37.5 μg of pcDNA3CMV-YU2 DNA was mixed with 37.5 μl of transfection reagent and added to the FreeStyle™ cell culture. Total supernatant containing the His6-tagged HIV Env gp140 protein was collected 4 days post-transfection, purified on a Ni-NTA affinity column (Qiagen), and concentrated using a 50 kDa MWCO centricon device. This Purified YU2gp140 protein was then subjected to analysis by Superdex 200 gel filtration chromatography. By this analysis, the recombinant protein formed a major peak that migrates at the position of ferritin (440 kDa). A small shoulder migrating closer to thyroglobulin (669 kDa) most likely corresponds to residual dimer or trimers. The peak fraction was collected, concentrated, and analyzed by native gel and Coomassie staining (inset). The positions of molecular weight standards are indicated by arrows (Amersham).

FIG. 12 shows conserved HA contact residues in anti-HA antibodies that recognize the "fusion pocket" epitope in the stalk domain of HA.

FIG. 13 shows the results of an ELISA assay. In particular, results of ELISA analysis of binding specificity of epitope surrogates displayed on phage are shown. Each Mab, top axis, was coated at 5 μg/mL on polystyrene plates in triplicate. 50 μL of each phage prep was added to individual rows as indicated on the left axis and bound phage was detected by anti-M13-HRP conjugate (GE Healthcare) at a 1:2000 dilution, as per the vendor's recommendation. It can be readily appreciated that each of the phage clones reacted specifically with its cognate antibody, but not with irrelevant/unrelated antibodies.

FIG. 14 shows the results of an ELISA assay. ELISA analysis of the specificity of selected b12 reactive phage clones is shown. Purified preps of WT b12 Mab and three b12 Mab mutants known to be incapable of binding to HIV-1 Env (Y53G, Y98A, W100A) were captured on polystyrene wells coated with goat anti-human IgG (5 μg/mL coat), top axis. A 1:10 dilution of phage preps, left axis, was then added to each well and bound phage was detected with anti-M13-HRP conjugate (GE Healthcare) at a 1:3000 dilution. B2.1 is a positive control phage encoding a peptide mimotope that binds wild type b12 Mab as well as the three mutant forms of the b12 Mab.

Figure 15:
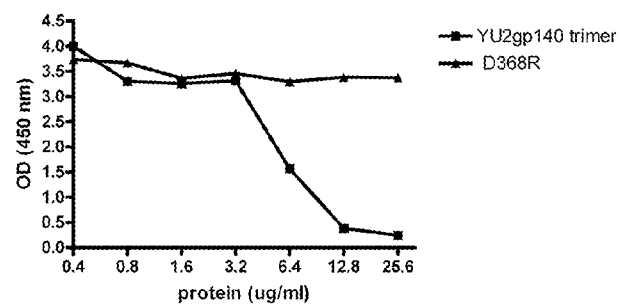

FIG. 15 show results which demonstrate that binding of purified b12 FN epitope surrogates to the b12 Mab is competitively inhibited by HIV-1 Env. Shown are the graphical results of an experiment in which biotinylated b12 3-5 FN protein (1 μg/mL) was bound to streptavidin plates. b12 Mab (1 μg/ml) was pre-incubated with varying amounts of wild type HIV-1 Env gp140 oligomers or mutant gp140 oligomers (D368R; this lacks the ability to bind to b12) and then added to the wells. Bound b12 Mab was detected with anti-human IgG-HRP conjugate at a 1:5000 dilution. The analysis shows that the wild-type gp140 trimer, but not the D368R mutant trimer, competitively inhibits binding of the b12 Mab to the b12 3-5 FN protein.

Figure 16:
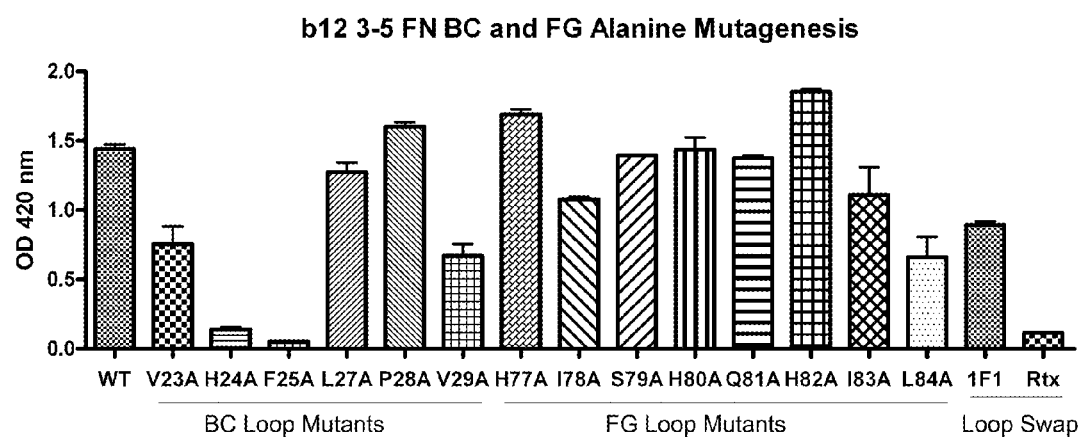

FIG. 16 shows graphical results of systematic alanine mutation of the BC and FG loop sequences. In particular, contribution of BC and FG loop residues to b12 Mab binding by the b12 3-5 FN epitope surrogate is shown. Protein FNs (1 μg/mL), as indicated, wild type b12 3-5 FN protein and mutated derivative thereof, were captured on streptavidin coated ELISA plates in triplicate, top axis. b12 Mab was added at a concentration of 10 ng/mL and detected by goat anti-human IgG-HRP conjugate at a 1:2000 dilution. Wild-type b12 3-5 FN protein sequence is BC loop=VHFALPV (SEQ ID NO:13) and FG loop=HISHQHIL (SEQ ID NO:14). A library of single alanine mutants for each of the amino acids in both the BC and FG loop were created. Additionally, the FG loop of wild-type b12 3-5 FN was replaced with FG loops from irrelevant FNs: 1F1 (FG loop=YWRTTPFM (SEQ ID NO:141)) or Rtx (FG loop=VWEWDQPQ (SEQ ID NO:139)). Key residues were determined by a reduction in binding affinity greater than 5×.

FIGS. 17A-B are graphical results showing epitope surrogates, 2F5 FN protein and 4E10 FN protein, competitively inhibit the binding of their corresponding antibodies to their target epitopes in the HIV-1 Env. FIG. 17A shows results of an experiment in which 2F5 peptide conjugated to BSA (5 μg/mL; BSA-Cys-NEQELLELDKWASLWSGGRGG-Lys (biotin)-NH2 (SEQ ID NO:142)) was immobilized on polystyrene plates in triplicate. 2F5 Mab (50 ng/mL) was pre-incubated with half log dilutions of 2F5 FN protein or 1F1 FN protein before addition to the coated plate. After extensive washing, Mab bound to the 2F5 peptide was detected with goat anti-human IgG-HRP conjugate at a 1:2000 dilution. FIG. 17B shows results from an experiment in which 4E10 peptide conjugated to BSA (5 μg/mL; BSA-Cys-SLWN-WFDITNWLWRRK(biotin)-NH2 (SEQ ID NO:143)) was immobilized on polystyrene plates in triplicate. 4E10 Mab (15.8 ng/mL) was pre-incubated with half log dilutions of 4E10 5-2 FN protein, 4E10 5-5 FN protein, or 1F1 FN protein before addition to the coated plate. After extensive washing, Mab bound to the 4E10 peptide was detected with goat anti-human IgG-HRP conjugate at a 1:2000 dilution.

FIG. 18 shows the identification of 4E10-FN and HIV gp140 reactive B cells by flow cytometry. Total PBMC from an HIV patient (HIV026), which has substantial serum antibody reactivity to the 4E10-FN and PBMC from a healthy control (HC1965) were stained with 7AAD, anti-CD3, anti-CD19, anti-CD20, anti-IgD, anti-IgM, anti-CD27 in addition to control Pacific Blue-conjugated 1F1-FN, AlexaFluor647-conjugated YU2 gp140, and biotinylated 4E10-FN coupled with SA-Alexa488 (top). Control samples stained with all reagents except 1F1-FN, YU2 gp140, and 4E10-FN were also prepared (No Ag Control, bottom). Samples were analyzed by flow cytometry. Plots are gated on 1F1-FN negative memory B cells (7AAD-CD3-CD19+CD20+IgD-IgM-CD27+).

Figure 19:
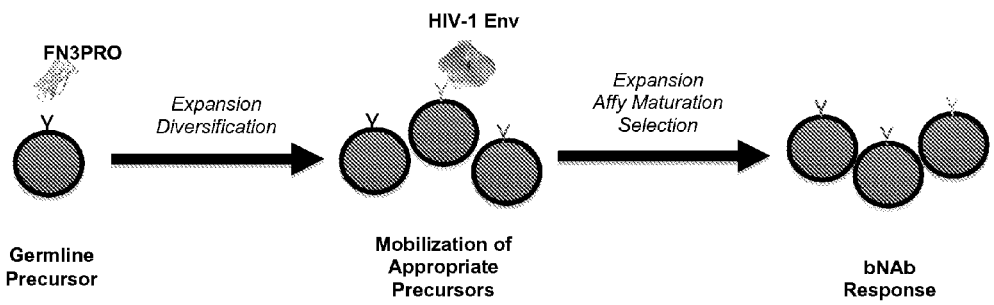

FIG. 19 is a schematic illustration of using an anti-idiotypic scaffold of the present invention to promote expansion and maturation of specified B cell progenitor cells, with the ability to give rise to mature cells capable of producing broadly neutralizing antibodies against a pathogen of interest (in this case, HIV-1).

Figure 20:
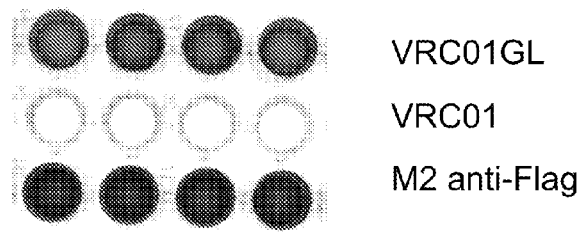

FIG. 20 shows of an anti-idiotypic (Id) FNfn10 directed against the predicted VRC01 "germline" antibody. An anti-Id FN scaffold of the present invention was selected against the VRC01 "germline" antibody, and then probed in quadruplicate wells for reactivity against mature VRC01 antibody (VRC01) versus its "germline revertant" (VRC01GL). Since the FN is tagged with the Flag epitope, reactivity with an anti-Flag antibody was included as a control.

Figure 21:
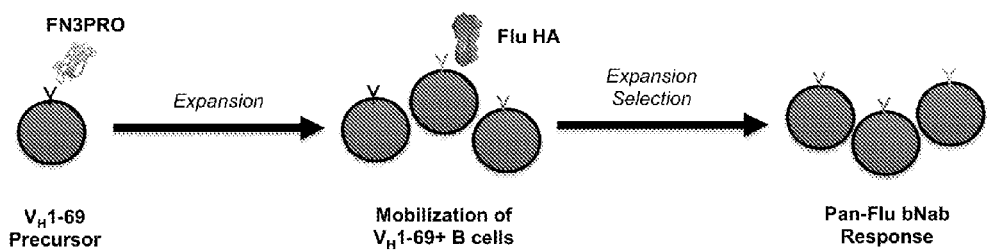

FIG. 21 is a schematic illustration of using an anti-idiotypic scaffold of the present invention to promote expansion and maturation of B cells expressing the VH1-69 immunoglobulin gene heavy chain V-region, with the goal of generating a pan-influenza vaccine.

DETAILED DESCRIPTION OF THE INVENTION

The polypeptides of the present invention are characterized by specificity for binding to a neutralizing monoclonal antibody and/or inducing a neutralizing immune response against a virus or bacteria. These polypeptides are based on a structurally-defined scaffold having a plurality of discontinuous loops that can be modified to elicit the desired activity. These polypeptides are in some instances referred to as "mimotopes," "peptide mimotopes," "antigenic mimics," "monobodies," or the like. By definition, these scaffolds are anti-idiotypic in nature.

Scaffolds for formation of a polypeptide according to the present invention should be highly soluble and stable. It should also be small enough for structural analysis, yet large enough to accommodate multiple binding domains so as to achieve tight binding and/or high specificity for its target.

The anti-idiotypic polypeptide scaffold of the invention includes two or more peptide sequences that mimic a discontinuous epitope of a pathogen that is recognized by a broadly neutralizing antibody.

An exemplary scaffold for formation of a polypeptide according to the present invention is the fibronectin type III domain (Fn3). Fibronectin is a large protein which plays essential roles in the formation of extracellular matrix and cell-cell interactions; it consists of many repeats of three types (types I, II, and III) of small domains (Baron et al., "Protein Modules," *Trends Biochem. Sci.* 16:13-17 (1991), which is hereby incorporated by reference in its entirety). Fn3 itself is the paradigm of a large subfamily (Fn3 family or s-type Ig family) of the immunoglobulin superfamily. The Fn3 family includes cell adhesion molecules, cell surface hormone and cytokine receptors, chaperonins, and carbohydrate-binding domains (for reviews, see Bork & Doolittle, "Proposed Acquisition of an Animal Protein Domain by Bacteria," *Proc. Natl. Acad. Sci. USA* 89:8990-8994 (1992); Jones, "The Immunoglobulin Superfamily," *Curr. Opinion Structural Biol.* 3:846-852 (1993); Bork et al., "The Immunoglobulin Fold. Structural Classification, Sequence Patterns and Common Core," *J. Mol. Biol.* 242:309-320 (1994); Campbell & Spitzfaden, "Building Proteins With Fibronectin Type III Modules," *Structure* 2:233-337 (1994); Harpez & Chothia, "Many of the Immunoglobulin Superfamily Domains in Cell Adhesion Molecules and Surface Receptors Belong to a New Structural Set Which is Close to That Containing Variable Domains," *J. Mol. Biol.* 238:528-539 (1994), which are hereby incorporated by reference in their entirety).

Crystallographic studies have revealed that the structure of the DNA binding domains of the transcription factor NF-kB is also closely related to the Fn3 fold (Ghosh et al., "Structure of NF-κB p50 Homodimer Bound to a κB Site," *Nature* 373:303-310 (1995); Müller et al., "Structure of the NHκ-B p50 Homodimer Bound to DNA," *Nature* 373:311-317 (1995), which are hereby incorporated by reference in their entirety). These proteins are all involved in specific molecular recognition, and in most cases ligand-binding sites are formed by surface loops, suggesting that the Fn3 scaffold is an excellent framework for building specific binding proteins. The 3D structure of Fn3 has been determined by NMR (Main et al., "The Three-Dimensional Structure of the Tenth Type III Module of Fibronectin: An Insight into RGD-Mediated Interactions," *Cell* 71:671-678 (1992), which is hereby incorporated by reference in its entirety) and by X-ray crystallography (Leahy et al., "Structure of a Fibronectin Type III Domain From Tenascin Phased by MAD Analysis of the Selenomethionlyl Protein," *Science* 258:987-991 (1992); Dickinson et al., "Crystal Structure of the Tenth Type III Cell Adhesion Module of Human Fibronectin," *J. Mol. Biol.* 236:1079-1092 (1994), which are hereby incorporated by reference in their entirety).

The tenth type III module of fibronectin has a fold similar to that of immunoglobulin domains, with seven β strands forming two antiparallel β sheets, which pack against each other (FIG. 1A; Main et al., "The Three-Dimensional Structure of the Tenth Type III Module of Fibronectin: An Insight into RGD-Mediated Interactions," *Cell* 71:671-678 (1992), which is hereby incorporated by reference in its entirety). One β sheet contains residues Glu-9-Thr-14 (A), Ser-17-Trp-22 (B), and Thr-56-Ser-60 (E) (see FIGS. 1A, 1C, and 1D). The majority of the conserved residues contribute to the hydrophobic core, with the invariant hydrophobic residues Trp-22 and Tyr-68 lying toward the N-terminal and C-terminal ends of the core, respectively. The β strands are much less flexible and appear to provide a rigid framework upon which functional, flexible loops can be built. The topology is similar to that of immunoglobulin C domains. As a result, this molecule has been proven to be a powerful and versatile molecular scaffold for the generation of binding proteins, termed "monobodies," with affinities in the nanomolar range (Koide et al., "Monobodies: Antibody Mimics Based on the Scaffold of the Fibronectin Type III Domain," *Methods Mol Biol.* 352:95-109 (2007); Richards et al., "Engineered Fibronectin Type III Domain with a RGDWXE Sequence Binds with Enhanced Affinity and Specificity to Human $\alpha_v\beta_3$ Integrin," *J Mol Biol.* 326(5):1475-88 (2003), which are hereby incorporated by reference in their entirety). The β-strand domain sequences A, B, C, D, E, F, and G of the tenth type III module of fibronectin is conserved among mammals generally (see FIG. 1D).

Advantages of this approach, as compared to unsuccessful earlier attempts to derive antigenic mimics of the discontinuous gp120 epitope recognized by the b12 Mab (Zwick et al., "Identification and Characterization of a Peptide that Specifically Binds the Human, Broadly Neutralizing Anti-human Immunodeficiency Virus Type 1 Antibody b12," *J. Virol.* 75(14):6692-9 (2001); Dorgham et al., "Immunogenicity of HIV Type 1 gp120 CD4 Binding Site Phage Mimotopes," *AIDS Res Hum Retroviruses* 21(1):82-92 (2005); Saphire et al., "Structure of a High-affinity "Mimotope" Peptide Bound to HIV-1-Neutralizing Antibody b12 Explains its Inability to Elicit gp120 Cross-reactive Antibodies," *J. Mol. Biol.* 369(3): 696-709 (2007); Zwick et al., "Molecular Features of the Broadly Neutralizing Immunoglobulin G1 b12 Required for Recognition of Human Immunodeficiency Virus Type 1 gp120," *J. Virol.* 77(10):5863-76 (2003), which are hereby incorporated by reference in their entirety), are as follows: (A) The FNfn10 molecular scaffold can be diversified in multiple discontinuous, but interacting, surface loop domains (Koide et al., "Monobodies: Antibody Mimics Based on the Scaffold of the Fibronectin Type III Domain," *Methods Mol. Biol.* 352:95-109 (2007); Koide et al., "The Fibronectin Type III Domain as a Scaffold for Novel Binding Proteins," *J. Mol. Biol.* 284(4):1141-51 (1998), which are hereby incorporated by reference in their entirety), unlike the conventional phage display peptide libraries that were used in previous Mab b12 studies (which were diversified only in a single continuous peptide domain); (B) the FNfn10 scaffold is very stable and easy to produce in large quantities suitable for immunization; and (C) the FNfn10 scaffold is based on a highly conserved self-protein (fibronectin). As a result, host immune responses directed against mutated derivatives of this scaffold are expected to focus on the displayed mimotopes (polypeptides) rather than the protein framework. This is expected to enhance the magnitude of the immune response elicited by the displayed HIV-1 Env antigen mimics. In addition, the FNfn10 and FNfn10-derived proteins can be readily produced in high quantities from *E. coli* host cells, and have been safely applied to human subjects, as evidenced by the recent entry of the FNfn10-derived protein, CT-322, into Phase II trials for the treatment of glioblastoma multiforme (Bloom et al., "FN3: A New Protein Scaffold Reaches the Clinic," *Drug Discovery Today* 14(19-20): 949-955 (2009), which is hereby incorporated by reference in its entirety).

According to one embodiment, the polypeptide of the present invention is a fibronectin type III (Fn3)-derived polypeptide monobody. Fn3 monobodies include at least two Fn3 β-strand domain sequences with a loop region sequence linked between adjacent β-strand domain sequences and optionally, an N-terminal tail of at least about 2 amino acids, a C-terminal tail of at least about 2 amino acids, or both. The at least one loop region sequence, the N-terminal tail, or the C-terminal tail, or combinations thereof mimic a neutralizing epitope of a virus or bacterium. To mimic the neutralizing epitope, either the loop region sequence, the N-terminal tail, the C-terminal tail, or a combination thereof varies by deletion, insertion, or replacement of at least two amino acids from a corresponding loop region, N-terminal tail, or C-terminal tail in a wild-type or mutant Fn3 scaffold.

According to another embodiment, the polypeptide comprises β-strand domain sequences A, B, C, D, E, F, and G of a wild-type mammalian Fn3 domain of fibronectin with loop region sequences AB, BC, CD, DE, EF, and FG linked between adjacent β-strand domain sequences. The polypeptide also optionally includes an N-terminal tail of at least about 2 amino acids, a C-terminal tail of at least about 2 amino acids, or both. At least one loop region sequence of the polypeptide comprises a modified amino acid sequence which varies by deletion, insertion, or replacement of at least two amino acids from a corresponding loop region in the wild-type mammalian Fn3 domain of fibronectin, and the polypeptide either (i) binds specifically to a neutralizing monoclonal antibody reactive to a virus or bacteria, (ii) induces a neutralizing immune response against the virus or bacteria, (iii) binds to unmutated genomic antibody genes capable of directly neutralizing the infectivity of a virus or bacteria, or (iv) binds to unmutated genomic antibody genes capable of giving rise to broadly neutralizing antibodies through somatic hypermutation.

The wild-type Fn3 domain of fibronectin can be a wild-type tenth Fn3 domain of a mammal, preferably from a human, bovine, chimpanzee, rhesus monkey, dog, equine, murine, or platypus fibronectin. As is illustrated in FIG. 1D, the wild-type tenth Fn3 domain is highly conserved among mammals.

One preferred wild-type Fn3 scaffold is the tenth Fn3 domain of human fibronectin (FNfn10), which has an amino acid sequence of (SEQ ID NO:2) as follows:

```
VSDVPRDLEV VAATPTSLLI SWDAPAVTVR YYRITYGETG

GNSPVQEFTV PGSKSTATIS GLKPGVDYTI TVYAVTGRGD

SPASSKPISI NYRT
```

One preferred mutant Fn3 scaffold is the tenth Fn3 domain of human fibronectin which has a modified Asp7, which is replaced by a non-negatively charged amino acid residue (i.e., Asn, Lys, etc.) (SEQ ID NO:51) as shown below:

```
VSDVPRXLEV VAATPTSLLI SWDAPAVTVR YYRITYGETG

GNSPVQEFTV PGSKSTATIS GLKPGVDYTI TVYAVTGRGD

SPASSKPISI NYRT
```

As reported in Koide et al., "Stabilization of a Fibronectin Type III Domain by the Removal of Unfavorable Electrostatic Interactions on the Protein Surface," *Biochemistry* 40(34): 10326-33 (2001) (which is hereby incorporated by reference in its entirety) both of these mutations have the effect of promoting greater stability of the mutant FNfn10 at neutral pH as compared to the wild-type FNfn10.

Another preferred Fn3 scaffold is the mature FNfn10 protein (after proteolytic removal of the N-terminal MQ residues), shown in FIG. 1C.

As noted above, both the mutant and wild-type FNfn10 are characterized by the same structure, namely seven β-strand domain sequences (designated A through G) and six loop regions (AB loop, BC loop, CD loop, DE loop, EF loop, and FG loop) which connect the seven β-strand domain sequences. As shown in FIG. 1A, the BC loop, DE loop, and FG loop are all located at the same end of the polypeptide.

Combinatorial libraries have been constructed by diversifying short surface exposed loops of the protein (BC, DE and FG; FIG. 1A). This approach has permitted the isolation of high affinity binding proteins, as described in previous work (Richards et al., "Engineered Fibronectin Type III Domain with a RGDWXE Sequence Binds with Enhanced Affinity and Specificity to Human $α_vβ_3$ Integrin," *J Mol Biol.* 326(5): 1475-88 (2003), which is hereby incorporated by reference in its entirety).

As noted above, several scaffolds of the present invention are based on the structure of a fibronectin module of type III (FnIII), a domain found in mammalian blood and structural proteins. Thus, the wild-type Fn3 domain of fibronectin according to the present invention may be replaced, in whole or in part, with corresponding sequences of similar proteins. The FnIII domain occurs often in the proteins sequenced to date, including fibronectins, tenascin, intracellular cytoskeletal proteins, cytokine receptors and prokaryotic enzymes (Bork et al., "Proposed Acquisition of an Animal Domain by Bacteria," *Proc. Natl. Acad. Sci. USA* 89:8990-94 (1992); Boder et al., "Yeast Surface Display for Screening Combinatorial Polypeptide Libraries," *Nat. Biotech.* 15:553-557 (1997); Meinke et al., "Cellulose-Binding Polypeptides from Cellulomonas fimi: Endoglucanase D (CenD), a Family A Beta-1,4-Glucanase," *J. Bacteria* 175:1910-18 (1993); Watanabe et al., "Gene Cloning of Chitinase A1 From *Bacil-lus Circulans* WL-12 Revealed its Evolutionary Relationship to *Serratia Chintinaseand* to the Type III Homology Units of Fibronectin," *J. Biol. Chem.* 265:15659-15665 (1990), which are hereby incorporated by reference in their entirety).

In one embodiment, the scaffold is the third Fn3 domain of human tenascin C (also known as the "Tn3" domain). U.S. Patent Application Publication Nos. 2010/0216708 and 2010/0298541, which are hereby incorporated by reference in their entirety. In one embodiment, the third FN3 domain from human Tenascin includes the amino acid sequence of SEQ ID NO:144:

```
DAPSQIEVKDVTDTTALITWFKPLAEIDGIELTYGIKDVPGDRTTIDL

TEDENQYSIGNLKPDTEYEVSLISRRGDMSSNPAKETFTT
``` or the consensus sequence of SEQ ID NO:169:

```
LPAPKNLVVSEVTEDSLRLSWTAPDAAFDSFLIQYQESEKVGEAINLT

VPGSERSYDLTGLKPGTEYTVSIYGVKGGHRSNPLSAEFTT
```

In yet another embodiment, the scaffold is a domain III polypeptide from a flaviviral envelope protein (e.g., the domain III from dengue virus envelope) (U.S. Patent Application Publication No. 2006/0115837 to Fremont et al., which is hereby incorporated by reference in its entirety), or combinations of replacement sequences from any such protein.

Regardless of which scaffold is used in preparing the polypeptides according to the present invention, the polypeptide can be modified by chemical PEGylation. In some embodiments, the polypeptide comprises polyethylene glycol (PEG). One or more PEG molecules may be attached at different positions on the protein, and such attachment may be achieved by reaction with amines, thiols or other suitable reactive groups. The amine moiety may be, for example, a primary amine found at the N-terminus of a polypeptide or an amine group present in an amino acid, such as lysine or arginine. In some embodiments, the PEG moiety is attached at a position on the polypeptide selected from the group consisting of: a) the N-terminus; b) between the N-terminus and the most N-terminal beta strand or beta-like strand; c) a loop positioned on a face of the polypeptide opposite the target-binding site; d) between the C-terminus and the most C-terminal beta strand or beta-like strand; and e) at the C-terminus.

Pegylation may be achieved by site-directed pegylation, wherein a suitable reactive group is introduced into the protein to create a site where pegylation preferentially occurs. In some embodiments, the protein is modified to introduce a cysteine residue at a desired position, permitting site directed pegylation on the cysteine. In some embodiments, the polypeptide comprises a Cys-containing linker, as described in U.S. Patent Application Publication No. 2009/0299040, which is hereby incorporated by reference in its entirety, which permits site directed pegylation. PEG may vary widely in molecular weight and may be branched or linear.

The virus whose epitopes can be mimicked using the claimed invention can be any type of virus. Exemplary viruses include, without limitations, Calicivirus, Chikungunya virus, Cytomegalovirus, Dengue virus, Eastern Equine Encephalitis virus, Ebola virus, Epstein-Barr virus, Hantaan virus, Hepatitis A virus, Hepatitis B virus, Hepatitis C virus, Hepatitis D virus, Hepatitis E virus, Herpes simplex virus, Human Immunodeficiency virus (HIV-1), Human Papillomavirus, Influenza virus, Japanese encephalitis virus, Junin virus, Lassa virus, Marburg virus, Measles virus, Metapneumovirus, Nipah virus, Newcastle disease virus, Norwalk virus, Parainfluenza virus, Poliovirus, Rabies virus, Respiratory Syncytial virus, Rift Valley Fever virus, Rotavirus, Rubella virus, Sendai virus, Severe Acute Respiratory Syndrome (SARS Co-V), Tick-borne Encephalitis virus, Varicella zoster virus, Venezuelan Equine Encephalitis virus, Yellow Fever virus, Western Equine Encephalitis virus, and West Nile virus.

The bacteria whose epitopes can be mimicked using the claimed invention can be any type of bacterium. Exemplary bacteria according to the embodiments the present invention may include, without limitation, *Bacillus anthracis, Bordetella pertussis* B, *Borrelia burgdorferi, Chlamydia trachomatis, Clostridium difficile, Clostridium tetani, Candida albicans, Corynebacterium diphtheriae, Cryptococcus neoformans, Entamoeba histolytica, Escherichia coli, Francisella tularensis, Haemophilus influenzae* (nontypeable), *Helicobacter pylori, Histoplasma capsulatum, Moraxella catarrhalis, Mycobacterium leprae, Mycobacterium tuberculosis, Neisseria gonorrheae, Neisseria meningitides, Pseudomonas aeruginosa, Staphylococcus aureus, Methicillin*-resistant *Staphylococcus aureus, Streptococcus agalactiae, Streptococcus pneumoniae, Streptococcus pyogenes,* and *Yersinia pestis.*

According to one particular embodiment, the polypeptide exhibits increased activity in binding to a neutralizing monoclonal antibody. Examples include, without limitation, those selected from the group consisting of HIV Mab b12, HIV F105 Mab, HIV PG9 Mab, HIV PG16 Mab, HIV 2G12 Mab, HIV 2F5 Mab, HIV 4E10 Mab, HIV VRC01 Mab, HIV Z13 Mab, HIV 447-52D Mab, Dengue 7D Mab, Dengue 1F1 Mab, Influenza CR6261 Mab, Influenza F10 Mab, Influenza D8 Mab, Rotavirus 4F8 Mab, *Neisseria meningitidis* Seam-3 Mab, 7D Dengue Mab, and HPV 1 Mab.

HIV b12 Mab recognizes a discontinuous epitope within the CD4 binding site of the HIV-1 envelope (Burton et al., "A Large Array of Human Monoclonal Antibodies to Type 1 Human Immunodeficiency Virus From Combinatorial Libraries of Asymptomatic Seropositive Individuals," *Proc Natl Acad Sci USA* 88:10134-7 (1991) and Burton et al., "Efficient Neutralization of Primary Isolates of HIV-1 by A Recombinant Human Monoclonal Antibody," *Science* 266: 1024-7 (1994), which are hereby incorporated by reference in their entirety). HIV F105 recognizes the CD4 binding site of gp120 (Posner et al., "Neutralization of HIV-1 by F105, A Human Monoclonal Antibody to the CD4 Binding Site of gp120," *J Acquir Immune Defic Syndr* 6:7-14 (1993) and Posner et al., "An IgG Human Monoclonal Antibody That Reacts With HIV-1/GP120, Inhibits Virus Binding to Cells, and Neutralizes Infection," *J Immunol* 146:4325-32 (1991), which are hereby incorporated by reference in their entirety). HIV PG9 Mab and HIV PG16 Mab recognize conformational epitopes on Env trimers (Walker et al., "Broad and Potent Neutralizing Antibodies From an African Donor Reveal A New HIV-1 Vaccine Target," *Science* 326:285-9 (2009). HIV 2G12 Mab recognizes epitopes derived from the glycan (carbohydrate) shield of the envelope (Hessell et al., "Broadly Neutralizing Human Anti-HIV Antibody 2G12 Is Effective in Protection Against Mucosal SHIV Challenge Even at Low Serum Neutralizing Titers," *PLoS Pathog* 5:e1000433 (2009); Sanders et al., "The Mannose-Dependent Epitope for Neutralizing Antibody 2G12 on Human Immunodeficiency Virus Type 1 Glycoprotein gp120," *J Virol* 76:7293-305 (2002); Trkola et al., "Cross-Clade Neutralization of Primary Isolates of Human Immunodeficiency Virus Type 1 by Human Monoclonal Antibodies and Tetrameric CD4-IgG," *J Virol.* 69:6609-17 (1995); and Trkola et al., "Human Monoclonal Antibody 2G12 Defines A Distinctive Neutralization Epitope on the gp120 Glycoprotein of Human Immunodeficiency Virus Type 1," *J Virol* 70:1100-8 (1996), which are hereby incorporated by reference in their entirety). HIV 2F5 Mab and HIV 4E10 Mab recognize the membrane-proximal envelope region (MPER) of gp41 (Montero et al., "The Membrane-Proximal External Region of the Human Immunodeficiency Virus Type 1 Envelope: Dominant Site of Antibody Neutralization and Target for Vaccine Design," *Microbiol Mol Biol Rev* 72:54-84, table of contents (2008); Muster et al., "A Conserved Neutralizing Epitope on gp41 of Human Immunodeficiency Virus Type 1," *J Virol* 67:6642-7 (1993) and Stiegler et al., "A Potent Cross-Clade Neutralizing Human Monoclonal Antibody Against A Novel Epitope on gp41 of Human Immunodeficiency Virus Type 1," *AIDS Res Hum Retroviruses* 17:1757-65 (2001), which are hereby incorporated by reference in their entirety). HIV Z13 Mab also recognizes the membrane-proximal envelope region (MPER) of gp41 (Nelson et al., "An Affinity-Enhanced Neutralizing Antibody against the Membrane-Proximal External Region of Human Immunodeficiency Virus Type 1 gp41 Recognizes an Epitope between Those of 2F5 and 4E10," *J. Virology* 81(8):4033-4043 (2007), which is hereby incorporated by reference in its entirety). HIV VRC01 Mab contacts gp120 mainly through immunoglobulin V-gene regions (Zhou et al., "Structural Basis for Broad and Potent Neutralization of HIV-1 by Antibody VRC01," *Science* 329(5993): 811-817 (2010), which is hereby incorporated by reference in its entirety). The HIV 447-52D Mab recognizes the V3 determinant of gp120 (Conley et al., "Neutralization of Primary Human Immunodeficiency Virus Type 1 Isolates by the Broadly Reactive Anti-V3 Monoclonal Antibody, 447-52D," *J. Virology* 68(11):6994-7000 (1994), which is hereby incorporated by reference in its entirety).

It is important to note that recent data show that even modest plasma concentrations of neutralizing antibodies can be sufficient to protect against mucosal SHIV challenge (Scheid et al., "Broad Diversity of Neutralizing Antibodies Isolated From Memory B Cells in HIV-infected Individuals," *Nature* 458(7238):636-40 (2009) and Li et al., "Analysis of Neutralization Specificities in Polyclonal Sera Derived from Human Immunodeficiency Virus Type 1-infected Individuals," *J Virol.* 83(2):1045-59 (2009), which are hereby incorporated by reference in their entirety).

A number of different loop modifications can be generated and screened for specific binding activity against HIV Mab b12. These include, but are not limited to, the following:

In one embodiment, the modified amino acid sequence of the at least one loop region sequence comprises VHFALPA (SEQ ID NO:11), YLSDVPDL (SEQ ID NO:12), VHFALPV (SEQ ID NO:13), HISHQHIL (SEQ ID NO:14), VHFAYPT (SEQ ID NO:15), DFPSAPPP (SEQ ID NO:16), VPFAFPT (SEQ ID NO:22), TNHYMVI (SEQ ID NO:23), TNHYMV (SEQ ID NO:24), VHFAWTV (SEQ ID NO:25), NWGDTHQH (SEQ ID NO:26), VHWALPV (SEQ ID NO:27), WWSGQWMP (SEQ ID NO:28), VHFAYPA (SEQ ID NO:29), DITMGYMY (SEQ ID NO:30), MDHTWLP (SEQ ID NO:31), QWDQNVWP (SEQ ID NO:32), WDWHTYC (SEQ ID NO:33), or CVWWDYQE (SEQ ID NO:34).

In another embodiment, the at least one loop region is the BC loop region. In one particular embodiment, the BC loop region includes a modified amino acid sequence that comprises VHFALPA (SEQ ID NO:11), VHFALPV (SEQ ID NO:13), VHFAYPT (SEQ ID NO:15), VPFAFPT (SEQ ID NO:22), VHFAWTV (SEQ ID NO:25), VHWALPV (SEQ ID NO:27), VHFAYPA (SEQ ID NO:29), MDHTWLP (SEQ ID NO:31), or WDWHTYC (SEQ ID NO:33).

In another embodiment, the at least one loop region is the FG loop region. In one particular embodiment, the FG loop region includes a modified amino acid sequence that comprises YLSDVPDL (SEQ ID NO:12), HISHQHIL (SEQ ID NO:14), DFPSAPPP (SEQ ID NO:16), TNHYMVI (SEQ ID NO:23), TNHYMV (SEQ ID NO:24), NWGDTHQH (SEQ ID NO:26), WWSGQWMP (SEQ ID NO:28), DITMGYMY (SEQ ID NO:30), QWDQNVWP (SEQ ID NO:32), or CVWWDYQE (SEQ ID NO:34).

In yet another embodiment, the at least one loop region is a combination of the BC loop region sequence and the FG loop region sequence. In one particular embodiment, the modified BC and FG loop region sequences comprise, respectively, VHFALPA (SEQ ID NO:11) and YLSDVPDL (SEQ ID NO:12); VHFALPV (SEQ ID NO:13) and HISHQHIL (SEQ ID NO:14); VHFAYPT (SEQ ID NO:15) and DFPSAPPP (SEQ ID NO:16); VPFAFPT (SEQ ID NO:22) and TNHYMVI (SEQ ID NO:23); VHFALPV (SEQ ID NO:13) and TNHYMV (SEQ ID NO:24); VHFAWTV (SEQ ID NO:25) and NWGDTHQH (SEQ ID NO:26); VHWALPV (SEQ ID NO:27) and WWSGQWMP (SEQ ID NO:28); VHFAYPA (SEQ ID NO:29) and DITMGYMY (SEQ ID NO:30); MDHTWLP (SEQ ID NO:31) and QWDQNVWP (SEQ ID NO:32); or WDWHTYC (SEQ ID NO:33) and CVWWDYQE (SEQ ID NO:34).

A number of different loop modifications can be generated and screened for specific binding activity against HIV 4E10 Mab. These include, but are not limited to, the following:

In one embodiment, the modified amino acid sequence of the at least one loop region sequence comprises TEWPEQY (SEQ ID NO:52), RWDPFTH (SEQ ID NO:53), DAHSFTA (SEQ ID NO:54), DAPAVTV (SEQ ID NO:55), SPLTFPA (SEQ ID NO:56), RHLFEYAE (SEQ ID NO:57), QNWFNQTS (SEQ ID NO:58), WNWFEQTN (SEQ ID NO:59), HNFFAQSA (SEQ ID NO:60), VLTHNFNN (SEQ ID NO:61), or FNFFLQTA (SEQ ID NO:62).

In another embodiment, the at least one loop region is the BC loop region. In one particular embodiment, the BC loop region includes a modified amino acid sequence that comprises TEWPEQY (SEQ ID NO:52), RWDPFTH (SEQ ID NO:53), DAHSFTA (SEQ ID NO:54), DAPAVTV (SEQ ID NO:55), or SPLTFPA (SEQ ID NO:56).

In another embodiment, the at least one loop region is the FG loop region. In one particular embodiment, the FG loop region includes a modified amino acid sequence that comprises RHLFEYAE (SEQ ID NO:57), QNWFNQTS (SEQ ID NO:58), WNWFEQTN (SEQ ID NO:59), HNFFAQSA (SEQ ID NO:60), VLTHNFNN (SEQ ID NO:61), or FNFFLQTA (SEQ ID NO:62).

In yet another embodiment, the at least one loop region is a combination of the BC loop region sequence and the FG loop region sequence. In one particular embodiment, the modified BC and FG loop region sequences comprise, respectively, TEWPEQY (SEQ ID NO:52) and RHLFEYAE (SEQ ID NO:57), RWDPFTH (SEQ ID NO:53) and QNWFNQTS (SEQ ID NO:58), DAHSFTA (SEQ ID NO:54) and WNWFEQTN (SEQ ID NO:59), DAPAVTV (SEQ ID NO:55) and HNFFAQSA (SEQ ID NO:60), DAPAVTV (SEQ ID NO:55) and VLTHNFNN (SEQ ID NO:61), or SPLTFPA (SEQ ID NO:56) and FNFFLQTA (SEQ ID NO:62).

A number of different loop modifications can be generated and screened for specific binding activity against HIV 2F5 Mab. These include, but are not limited to, the following:

In one embodiment, the modified amino acid sequence of the at least one loop region sequence comprises MWDKWSY (SEQ ID NO:63), PYDKWAY (SEQ ID NO:64), WWIGEFPV (SEQ ID NO:65), or RWYWVPHY (SEQ ID NO:66).

In another embodiment, the at least one loop region is the BC loop region. In one particular embodiment, the BC loop region includes a modified amino acid sequence that comprises MWDKWSY (SEQ ID NO:63) or PYDKWAY (SEQ ID NO:64).

In another embodiment, the at least one loop region is the FG loop region. In one particular embodiment, the FG loop region includes a modified amino acid sequence that comprises WWIGEFPV (SEQ ID NO:65) or RWYWVPHY (SEQ ID NO:66).

In yet another embodiment, the at least one loop region is a combination of the BC loop region sequence and the FG loop region sequence. In one particular embodiment, the modified BC and FG loop region sequences comprise, respectively, MWDKWSY (SEQ ID NO:63) and WWIGEFPV (SEQ ID NO:65) or PYDKWAY (SEQ ID NO:64) and RWYWVPHY (SEQ ID NO:66).

A number of different loop modifications can be generated and screened for specific binding activity against HIV Z13 Mab. These include, but are not limited to, the following:

In one embodiment, the modified amino acid sequence of the at least one loop region sequence comprises QPTFMPE (SEQ ID NO:67), EWQVDAE (SEQ ID NO:68), MEYSWQY (SEQ ID NO:69), ERWAMWY (SEQ ID NO:70), AHAWLPE (SEQ ID NO:71), QEASWLS (SEQ ID NO:72), YDEWFWT (SEQ ID NO:73), RRFWPPF (SEQ ID NO:74), SSTEWFV (SEQ ID NO:75), MIPWMVPG (SEQ ID NO:76), DWWWDTIE (SEQ ID NO:77), PWNWVDLT (SEQ ID NO:78), HPWIKWYW (SEQ ID NO:79), WHPWFQYE (SEQ ID NO:80), WVPEQFDQ (SEQ ID NO:81), DPWLMPPA (SEQ ID NO:82), TATKSFWW (SEQ ID NO:83), or DIPKQWGK (SEQ ID NO:84).

In another embodiment, the at least one loop region is the BC loop region. In one particular embodiment, the BC loop region includes a modified amino acid sequence that comprises QPTFMPE (SEQ ID NO:67), EWQVDAE (SEQ ID NO:68), MEYSWQY (SEQ ID NO:69), ERWAMWY (SEQ ID NO:70), AHAWLPE (SEQ ID NO:71), QEASWLS (SEQ ID NO:72), YDEWFWT (SEQ ID NO:73), RRFWPPF (SEQ ID NO:74), or SSTEWFV (SEQ ID NO:75).

In another embodiment, the at least one loop region is the FG loop region. In one particular embodiment, the FG loop region includes a modified amino acid sequence that comprises MIPWMVPG (SEQ ID NO:76), DWWWDTIE (SEQ ID NO:77), PWNWVDLT (SEQ ID NO:78), HPWIKWYW (SEQ ID NO:79), WHPWFQYE (SEQ ID NO:80), WVPEQFDQ (SEQ ID NO:81), DPWLMPPA (SEQ ID NO:82), TATKSFWW (SEQ ID NO:83), or DIPKQWGK (SEQ ID NO:84).

In yet another embodiment, the at least one loop region is a combination of the BC loop region sequence and the FG loop region sequence. In one particular embodiment, the modified BC and FG loop region sequences comprise, respectively, QPTFMPE (SEQ ID NO:67) and MIPWMVPG (SEQ ID NO:76), EWQVDAE (SEQ ID NO:68) and DWWWDTIE (SEQ ID NO:77), MEYSWQY (SEQ ID NO:69) and PWNWVDLT (SEQ ID NO:78), ERWAMWY (SEQ ID NO:70) and HPWIKWYW (SEQ ID NO:79), AHAWLPE (SEQ ID NO:71) and WHPWFQYE (SEQ ID NO:80), QEASWLS (SEQ ID NO:72) and WVPEQFDQ (SEQ ID NO:81), YDEWFWT (SEQ ID NO:73) and DPWLMPPA (SEQ ID NO:82), RRFWPPF (SEQ ID NO:74) and TATKSFWW (SEQ ID NO:83), or SSTEWFV (SEQ ID NO:75) and DIPKQWGK (SEQ ID NO:84).

A number of different loop modifications can be generated and screened for specific binding activity against HIV 447-52D Mab. These include, but are not limited to, the following:

In one embodiment, the modified amino acid sequence of the at least one loop region sequence comprises TVHAVPT (SEQ ID NO:85), SANFPSV (SEQ ID NO:86), ANAPVAT (SEQ ID NO:87), SKSTFHV (SEQ ID NO:88), LAPLSVV (SEQ ID NO:89), QFQYPVV (SEQ ID NO:90), APPLNVV (SEQ ID NO:91), APSLPVV (SEQ ID NO:92), FPSSLPV (SEQ ID NO:93), STSPLPT (SEQ ID NO:94), PPVMSPV (SEQ ID NO:95), LPPPHPL (SEQ ID NO:96), YVTLHPV (SEQ ID NO:97), TLPMLPT (SEQ ID NO:98), NWRWVMED (SEQ ID NO:99), PATQHPV (SEQ ID NO:100), LYPLDQSS (SEQ ID NO:101), DLHFYVVS (SEQ ID NO:102), LYPMQASL (SEQ ID NO:103), TSYYKKFP (SEQ ID NO:104), LYPYPVAS (SEQ ID NO:105), STYPLLIF (SEQ ID NO:106), LYPKPEPH (SEQ ID NO:107), LYPFPTQD (SEQ ID NO:108), LYNPQYMY (SEQ ID NO:109), LYPSHLSS (SEQ ID NO:110), LYPPAKVH (SEQ ID NO:111), LYPYPPIS (SEQ ID NO:112), LYPYPTHL (SEQ ID NO:113), LYPYPYEY (SEQ ID NO:114), SIHMGPRG (SEQ ID NO:115), or LYPLPPLL (SEQ ID NO:116).

In another embodiment, the at least one loop region is the BC loop region. In one particular embodiment, the BC loop region includes a modified amino acid sequence that comprises TVHAVPT (SEQ ID NO:85), SANFPSV (SEQ ID NO:86), ANAPVAT (SEQ ID NO:87), SKSTFHV (SEQ ID NO:88), LAPLSVV (SEQ ID NO:89), QFQYPVV (SEQ ID NO:90), APPLNVV (SEQ ID NO:91), APSLPVV (SEQ ID NO:92), FPSSLPV (SEQ ID NO:93), STSPLPT (SEQ ID NO:94), PPVMSPV (SEQ ID NO:95), LPPPHPL (SEQ ID NO:96), YVTLHPV (SEQ ID NO:97), TLPMLPT (SEQ ID NO:98), NWRWVMED (SEQ ID NO:99), PATQHPV (SEQ ID NO:100).

In another embodiment, the at least one loop region is the FG loop region. In one particular embodiment, the FG loop region includes a modified amino acid sequence that comprises LYPLDQSS (SEQ ID NO:101), DLHFYVVS (SEQ ID NO:102), LYPMQASL (SEQ ID NO:103), TSYYKKFP (SEQ ID NO:104), LYPYPVAS (SEQ ID NO:105), STYPLLIF (SEQ ID NO:106), LYPKPEPH (SEQ ID NO:107), LYPFPTQD (SEQ ID NO:108), LYNPQYMY (SEQ ID NO:109), LYPSHLSS (SEQ ID NO:110), LYPPAKVH (SEQ ID NO:111), LYPYPPIS (SEQ ID NO:112), LYPYPTHL (SEQ ID NO:113), LYPYPYEY (SEQ ID NO:114), SIHMGPRG (SEQ ID NO:115), or LYPLPPLL (SEQ ID NO:116).

In yet another embodiment, the at least one loop region is a combination of the BC loop region sequence and the FG loop region sequence. In one particular embodiment, the modified BC and FG loop region sequences comprise, respectively, TVHAVPT (SEQ ID NO:85) and LYPLDQSS (SEQ ID NO:101), SANFPSV (SEQ ID NO:86) and DLHFYVVS (SEQ ID NO:102), ANAPVAT (SEQ ID NO:87) and LYPMQASL (SEQ ID NO:103), SKSTFHV (SEQ ID NO:88) and TSYYKKFP (SEQ ID NO:104), LAPLSVV (SEQ ID NO:89) and LYPYPVAS (SEQ ID NO:105), QFQYPVV (SEQ ID NO:90) and STYPLLIF (SEQ ID NO:106), APPLNVV (SEQ ID NO:91) and LYPKPEPH (SEQ ID NO:107), APSLPVV (SEQ ID NO:92) and LYPFPTQD (SEQ ID NO:108), FPSSLPV (SEQ ID NO:93) and LYNPQYMY (SEQ ID NO:109), STSPLPT (SEQ ID NO:94) and LYPSHLSS (SEQ ID NO:110), PPVMSPV (SEQ ID NO:95) and LYPPAKVH (SEQ ID NO:111), LPPPHPL (SEQ ID NO:96) and LYPYPPIS (SEQ ID NO:112), YVTLHPV (SEQ ID NO:97) and LYPYPTHL (SEQ ID NO:113), TLPMLPT (SEQ ID NO:98) and LYPYPYEY (SEQ ID NO:114), NWRWVMED (SEQ ID NO:99) and SIHMGPRG (SEQ ID NO:115), or PATQHPV (SEQ ID NO:100) and LYPLPPLL (SEQ ID NO:116).

A number of different loop modifications can be generated and screened for specific binding activity against HIV VRC01 Mab. These include, but are not limited to, the following:

In one embodiment, the modified amino acid sequence of the at least one loop region sequence comprises SPPTFPM (SEQ ID NO:145), SLLDFPIV (SEQ ID NO:146), YVNAQVVF (SEQ ID NO:147), ATEELHVVSQ (SEQ ID NO:148), LPHAPMA (SEQ ID NO:149), PFYSFPHM (SEQ ID NO:150), MPFVFTP (SEQ ID NO:151), SYVPFADV (SEQ ID NO:152), LHHSPSA (SEQ ID NO:153), LTLLPNYV (SEQ ID NO:154), HISFPYT (SEQ ID NO:155), SLFYPVPS (SEQ ID NO:156), ATSLSTL (SEQ ID NO:157), FPNYSYPL (SEQ ID NO:158), ASSLPSL (SEQ ID NO:159), or FAPQLHTL (SEQ ID NO:160).

In another embodiment, the at least one loop region is the BC loop region. In one particular embodiment, the BC loop region includes a modified amino acid sequence that comprises SPPTFPM (SEQ ID NO:145), YVNAQVVF (SEQ ID NO:147), LPHAPMA (SEQ ID NO:149), MPFVFTP (SEQ ID NO:151), LHHSPSA (SEQ ID NO:153), HISFPYT (SEQ ID NO:155), ATSLSTL (SEQ ID NO:157), ASSLPSL (SEQ ID NO:159).

In another embodiment, the at least one loop region is the FG loop region. In one particular embodiment, the FG loop region includes a modified amino acid sequence that comprises SLLDFPIV (SEQ ID NO:146), ATEELHVVSQ (SEQ ID NO:148), PFYSFPHM (SEQ ID NO:150), SYVPFADV (SEQ ID NO:152), LTLLPNYV (SEQ ID NO:154), SLFYPVPS (SEQ ID NO:156), FPNYSYPL (SEQ ID NO:158), FAPQLHTL (SEQ ID NO:160).

In yet another embodiment, the at least one loop region is a combination of the BC loop region sequence and the FG loop region sequence. In one particular embodiment, the modified BC and FG loop region sequences comprise, respectively, SPPTFPM (SEQ ID NO:145) and SLLDFPIV (SEQ ID NO:146), YVNAQVVF (SEQ ID NO:147) and ATEELHVVSQ (SEQ ID NO:148), LPHAPMA (SEQ ID NO:149) and PFYSFPHM (SEQ ID NO:150), MPFVFTP (SEQ ID NO:151) and SYVPFADV (SEQ ID NO:152), LHHSPSA (SEQ ID NO:153) and LTLLPNYV (SEQ ID NO:154), HISFPYT (SEQ ID NO:155) and SLFYPVPS (SEQ ID NO:156), ATSLSTL (SEQ ID NO:157) and FPNYSYPL (SEQ ID NO:158), ASSLPSL (SEQ ID NO:159) and FAPQLHTL (SEQ ID NO:160).

The genomic precursors of somatically hypermutated broadly neutralizing antibodies may be selectively targeted by polypeptides of the present invention containing engineering loop sequences. In one embodiment of this approach, a number of different loop modifications can be generated and screened for specific binding activity against the predicted genomic precursor of the HIV-1 VRC01 Mab (Zhou et al., "Structural Basis for Broad and Potent Neutralization of HIV-1 by Antibody VRC01," *Science* 329(5993):811-7 (2010), which is hereby incorporated by reference in its entirety). In this case, selected FN molecules may contain modified BC and FG loop region sequences that include LQSALFA (SEQ ID NO:161) and PYFPAEFP (SEQ ID NO:162).

Influenza CR6261 Mab, F10 Mab, and D8 Mab recognize the "fusion" pocket of influenza HA (Ekiert et al., "Antibody Recognition of A Highly Conserved Influenza Virus Epitope," *Science* 324:246-51 (2009) and Sui et al., "Structural and Functional Bases for Broad-Spectrum Neutralization of Avian and Human Influenza A Viruses," *Nat Struct Mol Biol* 16:265-73 (2009), which are hereby incorporated by reference in their entirety). Influenza 1-69 Mab (or VH1-69-derived Mabs) recognizes the HA stalk of the influenza virus. Wrammert et al., "Broadly Cross-Reactive Antibodies Dominate the Human B Cell Response Against 2009 Pandemic H1N1 Influenza Virus Infection," *J. Exp. Med.* 208(1):181-193 (2011), which is hereby incorporated by reference in its entirety.

Influenza Mabs F10, D8 and other VH1-69 using antibodies may be modified to contain an arbitrary light chain, because binding to the HA antigen is mediated solely by the heavy chain of the Mab. In one embodiment, the heavy chain from Mab D8 can be paired with an arbitrary light chain. In this case, selected FN molecules may contain modified BC and FG loop region sequences that include VFWDQWT (SEQ ID NO:163) and WMQWWEFQ (SEQ ID NO:164). In another embodiment, the heavy chain from Mab F10 can be paired with an arbitrary light chain (such as the Vk chain from the b12 Mab directed against HIV-1).

A number of different loop modifications can be generated and screened for specific binding activity against influenza F10 Mab. These include, but are not limited to, the following:

In one embodiment, the modified amino acid sequence of the at least one loop region sequence comprises QQPEDAAD (SEQ ID NO:165), KSSEFYP (SEQ ID NO:166), LPAPMELKSP (SEQ ID NO:167), SFSSLFVS (SEQ ID NO:168).

In another embodiment, the at least one loop region is the BC loop region. In one particular embodiment, the BC loop region includes a modified amino acid sequence that comprises QQPEDAAD (SEQ ID NO:165) or KSSEFYP (SEQ ID NO:166).

In another embodiment, the at least one loop region is the FG loop region. In one particular embodiment, the FG loop region includes a modified amino acid sequence that comprises LPAPMELKSP (SEQ ID NO:167) or SFSSLFVS (SEQ ID NO:168).

In yet another embodiment, the at least one loop region is a combination of the BC loop region sequence and the FG loop region sequence. In one particular embodiment, the modified BC and FG loop region sequences comprise, respectively, QQPEDAAD (SEQ ID NO:165) and LPAPMELKSP (SEQ ID NO:167) or KSSEFYP (SEQ ID NO:166) and SFSSLFVS (SEQ ID NO:168).

The CDRs of other neutralizing antibodies can also be modified. The CDRs of Influenza neutralizing Mabs include, without limitation, VH1-69 CDR1=GTFSSY (SEQ ID NO:37) and CDR2=IIPIFGT (SEQ ID NO:38), F10 CDR1=VTFSSF (SEQ ID NO:39) and CDR2=ISPMFGT (SEQ ID NO:40), D8 CDR1=GTFSAY (SEQ ID NO:41) and CDR2=IIGMFGT (SEQ ID NO:42), A66 CDR1=GPFSMT (SEQ ID NO:43) and CDR2=ISPIFRT (SEQ ID NO:44), G17 CDR1=VTFSSY (SEQ ID NO:45) and CDR2=IIGVFGV (SEQ ID NO:46), D7 CDR1=GIFNTN (SEQ ID NO:47) and CDR2=VIPLFRT (SEQ ID NO:48), and CR6261 CDR1=GPFRSY (SEQ ID NO:49) and CDR2=IIPIFGT (SEQ ID NO:50).

Dengue 7D Mab is a strongly neutralizing and recognizes the dengue virus envelope glycoprotein (DENV) from all 4 serotypes of the virus (types 1-4). Dengue 1F1 Mab is a strongly neutralizing and recognizes domain III (DIII) of the dengue virus envelope glycoprotein (DENY); reacts only with DENV-2 and not with DENVs from other serotypes of the virus (types 1, 3, 4) (Megret et al., "Use of Recombinant Fusion Proteins and Monoclonal Antibodies to Define Linear and Discontinuous Antigenic Sites on the Dengue Virus Envelope Glycoprotein," *Virology* 187:480-91 (1992); Sukupolvi-Petty et al., "Type- and Subcomplex-Specific Neutralizing Antibodies Against Domain III of Dengue Virus Type 2 Envelope Protein Recognize Adjacent Epitopes," *J Virol* 81:12816-26 (2007), which are hereby incorporated by reference in their entirety).

A number of different loop modifications can be generated and screened for specific binding activity against anti-DENY Mab 7D. These include, but are not limited to the following:

In one embodiment, the modified amino acid sequence of the at least one loop region sequence comprises DAHSFTV (SEQ ID NO:117), PLYGFGFM (SEQ ID NO:118), AGRTVPQ (SEQ ID NO:119), WDWMWPNM (SEQ ID NO:120), DAHSFTV (SEQ ID NO:117), PLSPWGFQ (SEQ ID NO:121), PGDTWAS (SEQ ID NO:122), DIGAFAIP (SEQ ID NO:123), VWTNVNK (SEQ ID NO:124), WWWLWPEG (SEQ ID NO:125), YRVVHGV (SEQ ID NO:126), FFWSWPKE (SEQ ID NO:127), QPDRWI (SEQ ID NO:128), or DPWHMMFQ (SEQ ID NO:129).

In another embodiment, the at least one loop region is the BC loop region. In one particular embodiment, the BC loop region includes a modified amino acid sequence that comprises DAHSFTV (SEQ ID NO:117), AGRTVPQ (SEQ ID NO:119), DAHSFTV (SEQ ID NO:117), PGDTWAS (SEQ ID NO:122), VWTNVNK (SEQ ID NO:124), YRVVHGV (SEQ ID NO:126), or QPDRWI (SEQ ID NO:128).

In another embodiment, the at least one loop region is the FG loop region. In one particular embodiment, the FG loop region includes a modified amino acid sequence that comprises PLYGFGFM (SEQ ID NO:118), WDWMWPNM (SEQ ID NO:120), PLSPWGFQ (SEQ ID NO:121), DIGAFAIP (SEQ ID NO:123), WWWLWPEG (SEQ ID NO:125), FFWSWPKE (SEQ ID NO:127), or DPWHMMFQ (SEQ ID NO:129).

In yet another embodiment, the at least one loop region is a combination of the BC loop region sequence and the FG loop region sequence. In one particular embodiment, the modified BC and FG loop region sequences comprise, respectively, DAHSFTV (SEQ ID NO:117) and PLYGFGFM (SEQ ID NO:118); AGRTVPQ (SEQ ID NO:119) and WDWMWPNM (SEQ ID NO:120); DAHSFTV (SEQ ID NO:117) and PLSPWGFQ (SEQ ID NO:121); PGDTWAS (SEQ ID NO:122) and DIGAFAIP (SEQ ID NO:123); VWTNVNK (SEQ ID NO:124) and WWWLWPEG (SEQ ID NO:125); YRVVHGV (SEQ ID NO:126) and FFWSWPKE (SEQ ID NO:127); or QPDRWI (SEQ ID NO:128) and DPWHMMFQ (SEQ ID NO:129).

Rotavirus 4F8 Mab binds to the Rotavirus outer-layer protein VP7 (Shaw et al., "Antigenic Mapping of the Surface Proteins of Rhesus Rotavirus," J. Virol. 155(2):434-51 (1986); Aoki et al., "Structure of Rotavirus Outer-Layer Protein VP7 Bound with a Neutralizing Fab," *Science* 324: 1444-1447 (2009), which are hereby incorporated by reference in their entirety). Polypeptide scaffolds that bind to this Mab can be identified using the same procedures used to screen for HIV b12, Influenza F10, and Dengue 7D.

HPV RG-1 Mab is broadly neutralizing and reactive to L2 (Gambhira et al., "A Protective and Broadly Cross-Neutralizing Epitope of Human Papillomavirus L2," *J. Virol.* 81(24): 13927-13931 (2007), which is hereby incorporated by reference in its entirety). Polypeptide scaffolds that bind to this Mab can be identified using the same procedures used to screen for HIV b12, Influenza F10, and Dengue 7D.

*Neisseria meningitidis* Seam-3 Mab is reactive to meningococcal B polysaccharide (Baninati et al., "Protective Immunization Against Group B Meningococci Using Anti-Idiotypic Mimics of the Capsular Polysaccharide," *J. Immu-*

*nol.* 172:2461-2468 (2004) and Granoff et al., "Bactericidal Monoclonal Antibodies That Define Unique Meningococcal B Polysaccharide Epitopes That Do Not Cross-React with Human Polysialic Acid," *J. Immunol.* 160:5028-5036 (1998), which are hereby incorporated by reference in their entirety). Polypeptide scaffolds that bind to this Mab can be identified using the same procedures used to screen for HIV b12, Influenza F10, and Dengue 7D.

The polypeptides of the present invention can be prepared by recombinant techniques, thereby affording the deletion, insertion, or replacement of at least two amino acids from a corresponding loop region, N-terminal tail, or C-terminal tail in a wild-type or mutant Fn3, Tn3, or dIII scaffold. Deletions can be a deletion of at least two amino acid residues up to substantially all but one amino acid residue appearing in a particular loop region or tail. Insertions can be an insertion of at least two amino acid residues up to about 25 amino acid residues, preferably at least two up to about 15 amino acid residues. Replacements can be replacements of at least two up to substantially all amino acid residues appearing in a particular loop region or tail. The polypeptides of the present invention preferably possess an amino acid sequence which is at least 50% homologous to a β-strand domain of the FNfn10, Tn3, or dIII, as described above.

The deletions, insertions, and replacements (relative to wild-type or previously known mutant) on the scaffolds can be achieved using recombinant techniques beginning with a known nucleotide sequence. For example, a synthetic gene for the tenth Fn3 of human fibronectin was designed which includes convenient restriction sites for ease of mutagenesis and uses specific codons for high-level protein expression (Gribskov et al., "The Codon Preference Plot: Graphic Analysis of Protein Coding Sequences and Prediction of Gene Expression," *Nuc. Acids. Res.* 12:539-549 (1984), which is hereby incorporated by reference in its entirety). This gene is substantially identical to the gene disclosed in U.S. Pat. No. 6,673,901 to Koide, which is hereby incorporated by reference in its entirety.

The gene was assembled by Koide et al. as follows: first the gene sequence was divided into five parts with boundaries at designed restriction sites; for each part, a pair of oligonucleotides that code opposite strands and have complementary overlaps of about 15 bases was synthesized; the two oligonucleotides were annealed and single strand regions were filled in using the Klenow fragment of DNA polymerase; the double-stranded oligonucleotide was cloned into the pET3a vector (Novagen) using restriction enzyme sites at the termini of the fragment and its sequence was confirmed by an Applied Biosystems DNA sequencer using the dideoxy termination protocol provided by the manufacturer; and these steps were repeated for each of the five parts to obtain the whole gene. Although this approach takes more time to assemble a gene than the one-step polymerase chain reaction (PCR) method (Sandhu et al., "Dual Asymmetric PCR: One-Step Construction of Synthetic Genes," *BioTech.* 12:14-16 (1992), which is hereby incorporated by reference in its entirety), no mutations occurred in the gene. Mutations would likely have been introduced by the low fidelity replication by Taq polymerase and would have required time-consuming gene-editing. Recombinant DNA manipulations were performed according to Sambrook & Russell, Molecular Cloning: A Laboratory Manual (2d ed. 1989), which is hereby incorporated by reference in its entirety, unless otherwise stated. To avoid the introduction of mutations during one-step PCR, high fidelity/low error polymerases can be employed as is known in the art.

Desired mutations can be introduced to the scaffold gene using either cassette mutagenesis, oligonucleotide site-directed mutagenesis techniques (Deng & Nickoloff, "Site-Directed Mutagenesis of Virtually any Plasmid by Eliminating a Unique Site," *Anal. Biochem.* 200:81-88 (1992), which is hereby incorporated by reference in its entirety), or Kunkel mutagenesis (Kunkel et al., "Rapid and Efficient Site-Specific Mutagenesis Without Phenotypic Selection," *Proc. Natl. Acad. Sci. USA* 82:488-492 (1985); Kunkel et al., "Rapid and Efficient Site-Specific Mutagenesis Without Phenotypic Selection," *Methods Enzymol.* 154:367-382 (1987), which are hereby incorporated by reference in their entirety).

Both cassette mutagenesis and site-directed mutagenesis can be used to prepare specifically desired nucleotide coding sequences. Cassette mutagenesis can be performed using the same protocol for gene construction described above and the double-stranded DNA fragment coding a new sequence can be cloned into a suitable expression vector. Many mutations can be made by combining a newly synthesized strand (coding mutations) and an oligonucleotide used for the gene synthesis. Regardless of the approach utilized to introduce mutations into the nucleotide sequence encoding a polypeptide according to the present invention, sequencing can be performed to confirm that the designed mutations (and no other mutations) were introduced by mutagenesis reactions.

In contrast, Kunkel mutagenesis can be utilized to randomly produce a plurality of mutated polypeptide coding sequences which can be used to prepare a combinatorial library of polypeptides for screening. Basically, targeted loop regions (or C-terminal or N-terminal tail regions) can be randomized using the NNK codon (N denoting a mixture of A, T, G, C, and K denoting a mixture of G and T) (Kunkel et al., "Rapid and Efficient Site-Specific Mutagenesis Without Phenotypic Selection," *Methods Enzymol.* 154:367-382 (1987), which is hereby incorporated by reference in its entirety).

Another aspect of the present invention is a nucleic acid molecule encoding a polypeptide of the present invention. In one embodiment the nucleic acid is DNA. Still a further aspect of the present invention is a DNA construct comprising a DNA molecule that encodes a polypeptide of the present invention, a promoter-effective DNA molecule operably coupled 5' of the DNA molecule, and a transcription termination DNA molecule operably coupled 3' of the DNA molecule. Still a further aspect of the present invention is an expression vector into which is inserted the DNA construct of the present invention.

Regardless of the approach used to prepare the nucleic acid molecules encoding the polypeptide according to the present invention, the nucleic acid can be incorporated into host cells using conventional recombinant DNA technology. Generally, this involves inserting the DNA molecule into an expression system to which the DNA molecule is heterologous (i.e., not normally present). The heterologous DNA molecule is inserted into the expression system or vector in sense orientation and correct reading frame. The vector contains the necessary elements (promoters, suppressers, operators, transcription termination sequences, etc.) for the transcription and translation of the inserted protein-coding sequences. A recombinant gene or DNA construct can be prepared prior to its insertion into an expression vector. For example, using conventional recombinant DNA techniques, a promoter-effective DNA molecule can be operably coupled 5' of a DNA molecule encoding the polypeptide and a transcription termination (i.e., polyadenylation sequence) can be operably coupled 3' thereof.

In accordance with this aspect of the invention, the polynucleotides of the present invention are inserted into an expression system or vector to which the molecule is heterologous. The heterologous nucleic acid molecule is inserted into the expression system or vector in proper sense (5'→3') orientation relative to the promoter and any other 5' regulatory molecules, and correct reading frame. The preparation of the nucleic acid constructs can be carried out using standard cloning methods well known in the art as described by SAMBROOK & RUSSELL, MOLECULAR CLONING: A LABORATORY MANUAL (Cold Springs Laboratory Press, 2001), which is hereby incorporated by reference in its entirety. U.S. Pat. No. 4,237,224 to Cohen and Boyer, which is hereby incorporated by reference in its entirety, also describes the production of expression systems in the form of recombinant plasmids using restriction enzyme cleavage and ligation with DNA ligase.

Suitable expression vectors include those which contain replicon and control sequences that are derived from species compatible with the host cell. For example, if E. coli is used as a host cell, plasmids such as pUC19, pUC18 or pBR322 may be used. When using insect host cells, appropriate transfer vectors compatible with insect host cells include, pVL1392, pVL1393, pAcGP67 and pAcSecG2T, which incorporate a secretory signal fused to the desired protein, and pAcGHLT and pAcHLT, which contain GST and 6×His tags (BD Biosciences, Franklin Lakes, N.J.). Viral vectors suitable for use in carrying out this aspect of the invention include, adenoviral vectors, adeno-associated viral vectors, vaccinia viral vectors, nodaviral vectors, and retroviral vectors. Other suitable expression vectors are described in SAMBROOK AND RUSSELL, MOLECULAR CLONING: A LABORATORY MANUAL (Cold Springs Laboratory Press, 2001), which is hereby incorporated by reference in its entirety. Many known techniques and protocols for manipulation of nucleic acids, for example in preparation of nucleic acid constructs, mutagenesis, sequencing, introduction of DNA into cells and gene expression, and analysis of proteins, are described in detail in CURRENT PROTOCOLS IN MOLECULAR BIOLOGY (Fred M. Ausubel et al. eds., 2003), which is hereby incorporated by reference in its entirety.

Different genetic signals and processing events control many levels of gene expression (e.g., DNA transcription and messenger RNA ("mRNA") translation) and subsequently the amount of scaffold polypeptides and fusion proteins that are produced and expressed by the host cell. Transcription of DNA is dependent upon the presence of a promoter, which is a DNA sequence that directs the binding of RNA polymerase, and thereby promotes mRNA synthesis. Promoters vary in their "strength" (i.e., their ability to promote transcription). For the purposes of expressing a cloned gene, it is desirable to use strong promoters to obtain a high level of transcription and, hence, expression. Depending upon the host system utilized, any one of a number of suitable promoters may be used. For instance, when using E. coli, its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other E. coli promoters produced by recombinant DNA or other synthetic DNA techniques may be used to provide for transcription of the inserted gene. When using insect cells, suitable baculovirus promoters include late promoters, such as 39K protein promoter or basic protein promoter, and very late promoters, such as the p10 and polyhedron promoters. In some cases it may be desirable to use transfer vectors containing multiple baculoviral promoters. Common promoters suitable for directing expression in mammalian cells include, without limitation, SV40, MMTV, metallothionein-1, adenovirus E1a, CMV, immediate early, immunoglobulin heavy chain promoter and enhancer, and RSV-LTR. The promoters can be constitutive or, alternatively, tissue-specific or inducible. In addition, in some circumstances inducible (TetOn) promoters can be used.

Translation of mRNA in prokaryotes depends upon the presence of the proper prokaryotic signals, which differ from those of eukaryotes. Efficient translation of mRNA in prokaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and promote binding of mRNA to ribosomes by duplexing with the rRNA to allow correct positioning of the ribosome. For a review on maximizing gene expression, see Roberts and Lauer, "Maximizing Gene Expression on a Plasmid Using Recombination In Vitro," Methods in Enzymology, 68:473-82 (1979), which is hereby incorporated by reference in its entirety.

Yet another aspect of the present invention is a host cell transformed with the DNA construct of the present invention. The host cell can be a prokaryote or a eukaryote.

Host cells suitable for expressing the polypeptides of the present invention include any one of the more commonly available gram negative bacteria. Suitable microorganisms include Pseudomonas aeruginosa, Escherichia coli, Salmonella gastroenteritis (typhimirium), S. typhi, S. enteriditis, Shigella flexneri, S. sonnie, S. dysenteriae, Neisseria gonorrhoeae, N. meningitides, Haemophilus influenzae, H. pleuropneumoniae, Pasteurella haemolytica, P. multilocida, Legionella pneumophila, Treponema pallidum, T. denticola, T. orales, Borrelia burgdorferi, Borrelia spp., Leptospira interrogans, Klebsiella pneumoniae, Proteus vulgaris, P. morganii, P. mirabilis, Rickettsia prowazeki, R. typhi, R. richettsii, Porphyromonas (Bacteriodes) gingivalis, Chlamydia psittaci, C. pneumoniae, C. trachomatis, Campylobacter jejuni, C. intermedis, C. fetus, Helicobacter pylori, Francisella tularenisis, Vibrio cholerae, Vibrio parahaemolyticus, Bordetella pertussis, Burkholderie pseudomallei, Brucella abortus, B. susi, B. melitensis, B. canis, Spirillum minus, Pseudomonas mallei, Aeromonas hydrophila, A. salmonicida, and Yersinia pestis.

In addition to bacteria cells, animal cells, in particular mammalian and insect cells, yeast cells, fungal cells, plant cells, or algal cells are also suitable host cells for transfection/transformation of the recombinant expression vector carrying an isolated polynucleotide molecule of the present invention. Mammalian cell lines commonly used in the art include Chinese hamster ovary cells, HeLa cells, baby hamster kidney cells, COS cells, and many others. Suitable insect cell lines include those susceptible to baculoviral infection, including Sf9 and Sf21 cells.

Methods for transforming/transfecting host cells with expression vectors are well-known in the art and depend on the host system selected, as described in SAMBROOK & RUSSELL, MOLECULAR CLONING: A LABORATORY MANUAL (Cold Springs Laboratory Press, 2001), which is hereby incorporated by reference in its entirety. For bacterial cells, suitable techniques include calcium chloride transformation, electroporation, and transfection using bacteriophage For eukaryotic cells, suitable techniques include calcium phosphate transfection, DEAE-Dextran, electroporation, liposome-mediated transfection, and transduction using retrovirus or any other viral vector. For insect cells, the transfer vector containing the polynucleotide construct of the present invention is co-transfected with baculovirus DNA, such as AcNPV, to facilitate the production of a recombinant virus resulting from homologous recombination between the scaffold-encoding polynucleotide construct in the transfer vector and baculovirus DNA. Subsequent recombinant viral infection of Sf cells results in a high rate of recombinant protein production. Regardless of the expression system and host cell used to facilitate protein production, the expressed polypeptides and fusion proteins of the present invention can be readily purified using standard purification methods known in the art and described in PHILIP L. R. BONNER, PROTEIN PURIFICATION (Routledge 2007), which is hereby incorporated by reference in its entirety.

In at least several of the various uses of the polypeptides of the present invention, discussed infra, it is often desirable for the polypeptides to be produced in substantially purified form, particularly when their administration to a patient is contemplated. Purification can be carried out according to previously reported procedures, which involve metal affinity chromatography for polypeptides containing a poly-histidine tag (see Koide et al., "The Fibronectin Type III Domain as a Scaffold for Novel Binding Proteins," *J. Mol. Biol.* 284(4): 1141-51 (1998), which is hereby incorporated by reference in its entirety).

Another aspect of the present invention is directed to a fusion protein including any one of the isolated polypeptides of the present invention described supra linked by an in-frame fusion to an adjuvant polypeptide.

By way of example, and without limitation, suitable fusion proteins of the present invention include an adjuvant polypeptide fused in-frame to any one of the polypeptides of the present invention. The adjuvant polypeptide can be any peptide adjuvant known in art including, but not limited to, flagellin, human papillomavirus (HPV) L1 or L2 proteins, herpes simplex glycoprotein D (gD), complement C4 binding protein, toll-like receptor-4 (TLR4) ligand, and IL-1β.

The fusion polypeptide or protein of the present invention can be generated using standard techniques known in the art. For example, the fusion polypeptide can be prepared by translation of an in-frame fusion of the polynucleotide sequences of the present invention and the adjuvant, i.e., a hybrid gene. The hybrid gene encoding the fusion polypeptide is inserted into an expression vector which is used to transform or transfect a host cell. Alternatively, the polynucleotide sequence encoding the polypeptide of the present invention is inserted into an expression vector in which the polynucleotide encoding the adjuvant is already present. The peptide adjuvant of the fusion protein can be fused to the N-, or preferably, to the C-terminal end of the polypeptide of the present invention.

Fusions between the polypeptides of the present invention and the protein adjuvant may be such that the amino acid sequence of the polypeptide of the present invention is directly contiguous with the amino acid sequence of the adjuvant. Alternatively, the polypeptide portion may be coupled to the adjuvant by way of a short linker sequence. Suitable linker sequences include glycine rich linkers (e.g., $GGGS_{2-3}$), serine-rich linkers (e.g., $GS_N$), or other flexible immunoglobulin linkers as disclosed in U.S. Pat. No. 5,516,637 to Huang et al, which is hereby incorporated by reference in its entirety.

Another aspect of the present invention is directed to an immunogenic conjugate including any one of the polypeptides of the present invention conjugated to an immunogenic carrier molecule.

Suitable immunogenic conjugates of the present invention include, but are not limited to, an immunogenic carrier molecule covalently or non-covalently bonded to any one of the polypeptides of the present invention. Any suitable immunogenic carrier molecule can be used. Exemplary immunogenic carrier molecules include, but are in no way limited to, bovine serum albumin, chicken egg ovalbumin, keyhole limpet hemocyanin, tetanus toxoid, diphtheria toxoid, thyroglobulin, a pneumococcal capsular polysaccharide, CRM 197, and a meningococcal outer membrane protein.

Yet another aspect of the present invention relates to a composition comprising a pharmaceutically acceptable carrier and a polypeptide or conjugate according to the present invention.

A further aspect of the present invention relates to a vaccine comprising a pharmaceutically acceptable carrier and either a polypeptide according to the present invention, a DNA molecule according to the present invention, an expression vector according to the present invention, or a combination thereof.

Pharmaceutical compositions suitable for injectable use (e.g., intravenous, intra-arterial, intramuscular, etc.) may include sterile aqueous solutions or dispersions and sterile powders for the extemporaneous preparation of sterile injectable solutions or dispersions. In all cases, the form should be sterile and should be fluid to the extent that easy syringability exists. It should be stable under the conditions of manufacture and storage and should be preserved against the contaminating action of microorganisms, such as bacteria and fungi. Suitable adjuvants, carriers and/or excipients, include, but are not limited to sterile liquids, such as water and oils, with or without the addition of a surfactant and other pharmaceutically and physiologically acceptable carriers. Illustrative oils are those of petroleum, animal, vegetable, or synthetic origin, for example, peanut oil, soybean oil, or mineral oil. In general, water, saline, aqueous dextrose and related sugar solutions, and glycols, such as propylene glycol or polyethylene glycol, are preferred liquid carriers, particularly for injectable solutions.

Oral dosage formulations can include standard carriers such as pharmaceutical grades of mannitol, lactose, starch, magnesium stearate, sodium saccharine, cellulose, magnesium carbonate, etc. Suitable carriers include lubricants and inert fillers such as lactose, sucrose, or cornstarch. In another embodiment, these compounds are tableted with conventional tablet bases such as lactose, sucrose, or cornstarch in combination with binders like acacia, gum gragacanth, cornstarch, or gelatin; disintegrating agents such as cornstarch, potato starch, or alginic acid; a lubricant like stearic acid or magnesium stearate; sweetening agents such as sucrose, lactose, or saccharine; and flavoring agents such as peppermint oil, oil of wintergreen, or artificial flavorings. Generally, the ingredients are supplied either separately or mixed together in unit dosage form, for example, as a dry lyophilized powder or water free concentrate in a hermetically sealed container such as an ampule or sachette indicating the quantity of active agent.

For oral therapeutic administration, these active compounds may be incorporated with excipients and used in the form of tablets, capsules, elixirs, suspensions, syrups, and the like. Such compositions and preparations should contain at least 0.1% of active compound. The percentage of the compound in these compositions may, of course, be varied and may conveniently be between about 2% to about 60% of the weight of the unit. The amount of active compound in such therapeutically useful compositions is such that a suitable dosage will be obtained. Preferred compositions according to the present invention are prepared so that an oral dosage unit contains between about 1 and 250 mg of active compound.

These active compounds may also be administered parenterally. Solutions or suspensions of these active compounds can be prepared in water suitably mixed with a surfactant, such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols such as, propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils. Formulations suitable for transdermal delivery can also be prepared in accordance with the teachings of Lawson et al., "Use of Nanocarriers for Transdermal Vaccine Delivery," *Clin Pharmacol Ther* 82(6):641-3 (2007), which is hereby incorporated by reference in its entirety.

The compounds of the present invention may also be administered directly to the airways in the form of an aerosol. For use as aerosols, the compounds of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer. Formulations suitable for intranasal nebulization or bronchial aerosolization delivery are also known and can be used in the present invention (see Lu & Hickey, "Pulmonary Vaccine Delivery," *Exp Rev Vaccines* 6(2):213-226 (2007) and Alpar et al., "Biodegradable Mucoadhesive Particulates for Nasal and Pulmonary Antigen and DNA Delivery," *Adv Drug Deliv Rev* 57(3):411-30 (2005), which are hereby incorporated by reference in their entirety.

The pharmaceutical compositions of the present invention can also include an effective amount of a separate adjuvant. Suitable adjuvants for use in the present invention include, without limitation, aluminum hydroxide, aluminum phosphate, aluminum potassium sulfate, beryllium sulfate, silica, kaolin, carbon, water-in-oil emulsions, oil-in-water emulsions, muramyl dipeptide, bacterial endotoxin, lipid, Quil A, and/or non-infective *Bordetella pertussis*.

The choice of an adjuvant depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, alum, MPL or Incomplete Freund's adjuvant (Chang et al., *Advanced Drug Delivery Reviews* 32:173-186 (1998), which is hereby incorporated by reference in its entirety) alone or optionally all combinations thereof are suitable for human administration.

The present invention also relates to a method of imparting resistance to a viral or bacterial pathogen comprising administration of a vaccine according to the present invention to a mammal under conditions effective to induce a protective immune response against the virus or bacteria.

The compositions of the present invention can be administered orally, parenterally, for example, subcutaneously, intravenously, intramuscularly, intraperitoneally, by intranasal instillation, or by application to mucous membranes, such as, that of the nose, throat, and bronchial tubes. They may be administered alone or with suitable pharmaceutical carriers, and can be in solid or liquid form such as, tablets, capsules, powders, solutions, suspensions, or emulsions. Acceptable pharmaceutical carriers include solutions, suspensions, emulsions, excipients, powders, or stabilizers. The carrier should be suitable for the desired mode of delivery, discussed infra.

A further aspect of the present invention relates to a method of treating a viral or bacterial infection comprising administering to a patient an antibody or fragment thereof according to the present invention, or a pharmaceutical composition according to the present invention, under conditions to neutralize the virus or bacteria, and thereby treat the viral or bacterial infection.

Another aspect of the present invention relates to a method for inducing a neutralizing antibody response in a subject. The method comprises the steps of providing a subject in need of a neutralizing antibody response and administering a vaccine according to the present invention in a manner effective to induce a neutralizing antibody response in the subject.

It is contemplated that the individual to be treated in accordance with the present invention can be any mammal, but preferably a human. Veterinary uses are also contemplated. While the individual can be any mammal that is known to be susceptible to a viral or bacterial infection; the polypeptides of the present invention or the pharmaceutical composition containing the same is preferably derived from a genotype that is specific to the host mammal to be immunized in accordance with the present invention. For example, for inducing an immune response in humans it is preferable that the polypeptide is derived from a human viral or bacterial strain, or at least a strain that is capable of infecting humans. Moreover, the pharmaceutical composition can be multi-valent, containing antigen directed to different viral or bacterial strains, which collectively provide a more protective immune response.

As noted supra, the pharmaceutical composition can be administered by any means suitable for producing the desired immune response. The composition can be delivered repeatedly over a course of time, i.e., according to a prime/boost regiment, that achieves optimal enhancement of the immune response, which is discussed further infra.

According to one embodiment, the polypeptide of the present invention binds to unmutated genomic antibody genes capable of directly neutralizing the infectivity of a virus or bacteria or binds to unmutated genomic antibody genes capable of giving rise to broadly neutralizing antibodies through somatic hypermutation.

Exemplary genomic antibody genes include, without limitation, those relating to the neutralizing antibodies described herein. In one embodiment, the polypeptide binds to VH1-69 gene of antibodies directed against the influenza virus HA stalk region. See Wrammert et al., "Broadly Cross-Reactive Antibodies Dominate the Human B Cell Response Against 2009 Pandemic H1N1 Influenza Virus Infection," *J. Exp. Med.* 208(1):181-193 (2011); Kwong and Wilson, "HIV-1 and Influenza Antibodies: Seeing Antigens in New Ways," *Nature Immunol.* 10(6):573-578 (2009); Ekiert et al., "Antibody Recognition of a Highly Conserved Influenza Virus Epitope," *Science* 324(5924):246-251 (2009); Sui et al., "Structural and Functional Bases for Broad-Spectrum Neutralization of Avian and Human Influenza A Viruses," *Nat. Struct. Mol. Biol.* 16(3):265-273 (2009), which are hereby incorporated by reference in their entirety. In yet another embodiment, the polypeptide binds to IGHV3-30*18, IGKV3-11*01, and/or related structures that will be known to those of skill in the art, which are genes relating to human cytomegalovirus ("HCMV")-specific neutralizing antibodies. See Thomson et al., "Germline V-genes Sculpt the Binding Site of a Family of Antibodies Neutralizing Human Cytomegalovirus," 27(19):2592-2602 (2008); McLean et al., "Recognition of Human Cytomegalovirus by Human Primary Immunoglobulins Identifies an Innate Foundation to an Adaptive Immune Response," *J. Immunol.* 174:4768-4778 (2005), which are hereby incorporated by reference in their entirety. Yet another example includes germline genes relating to HIV-1 VRC01 Mab. See Zhou et al., "Structural Basis for Broad and Potent Neutralization of HIV-1 by Antibody VRC01," *Science* 329(5993):811-817 (2010), which is hereby incorporated by reference in its entirety. However, it will be understood that this embodiment may be practiced according to the present invention with any unmutated genomic antibody genes capable of directly neutralizing the infectivity of a virus or bacteria or capable of giving rise to broadly neutralizing antibodies through somatic hypermutation.

According to one embodiment, illustrated in FIGS. 19 and 21, the polypeptide of the present invention (designated FN3PRO) binds to the germline progenitors of a neutralizing monoclonal antibody reactive to a virus or a bacteria. This is effective to mobilize or elicit neutralizing monoclonal antibody progenitor cells that have the capacity to give rise to somatically mutated, affinity matured, virus or bacteria-specific broadly neutralizing antibodies. Subsequent to this administration, a conventional immunogen or antigen (i.e., subunit vaccine, virus-like particle, or inactivated or live, attenuated virus) is used to stimulate maturation to elicit an immune response to the particular virus or bacteria. In FIG. 19, by way of example, an HIV-1 Env particle can be used to induce affinity maturation of the B cell response. In FIG. 21, by way of example, an influenza HA particle can be used to induce affinity maturation of the B cell response.

The germline progenitors can either be contacted ex vivo or contacted in vivo, i.e., by administration of the polypeptide to an individual.

For example, the present disclosure provides methods for inducing differentiation of memory B cells and plasma cells from B cell progenitors and mature B cells, in quantities suitable for isolation of memory B cells and plasma cells. A population of cells including B cell progenitors and/or mature, antigen specific IgD expressing B cells are contacted with a composition including the polypeptide according to the present invention. Following exposure to an effective amount of a polypeptide according to the present invention, B cell progenitors and mature B cells preferentially differentiate into memory B cells and plasma cells.

For example, a population of bone marrow derived cells or peripheral blood cells including a wide variety of cell types including B cell progenitors and mature B cells can be exposed to a composition that includes a polypeptide according to the present invention, thereby inducing differentiation of B cell progenitors and mature B cells into memory B cells and/or plasma cells. Optionally, B cell progenitors and/or mature B cells can be isolated prior to treating them with a polypeptide according to the present invention. The methods described herein are applicable to B cells derived from a variety of species, particularly mammals, including humans.

As disclosed herein, a polypeptide according to the present invention preferentially promotes differentiation of B cells into mature subsets with desirable functional attributes. Thus, a polypeptide according to the present invention is of use to enhance an immune response in a subject, including a human subject, to a bacterial or viral pathogen. Although these methods have widespread applicability to enhance the efficacy of an immune response in a subject, these methods can also be employed more particularly to ameliorate immunodeficiencies, especially a deficiency characterized by reduction in number or function of memory B cells and/or plasma cells. For example, the methods described herein for enhancing an immune response can be used to treat a subject with a post-transplantation B cell deficiency.

An immune response in a subject can be enhanced by contacting a population of cells including mature B cells and/or B cell progenitors with a composition containing a polypeptide according to the present invention to induce differentiation of the mature B cells or B cell progenitors into memory B cells and/or plasma cells specific to the viral or bacterial pathogen, as noted above. The differentiated mature B cells and plasma cells are then isolated and introduced into a subject to enhance an immune response.

For example, the cells can be contacted with a polypeptide according to the present invention by administering a composition containing a polypeptide according to the present invention directly to the subject, such as a human subject. In this case, the polypeptide according to the present invention is administered in a pharmaceutically acceptable formulation, such as a formulation containing a polypeptide according to the present invention and a pharmaceutically acceptable carrier or excipient. Alternatively, the cells can be contacted with a polypeptide according to the present invention ex vivo.

In some cases, the population of cells including mature B cells and/or B cell progenitors, such as immature B cells, is isolated. For example, mature B cells and/or B cell progenitors can be isolated from peripheral blood or bone marrow. Optionally, the cells can also be contacted with an antigen, such as an antigen derived from a pathogen (e.g., a bacterial antigen, a viral antigen, or an antigen from a parasite) together with a polypeptide according to the present invention or after, for instance, as a booster.

Further, the memory B cells and plasma cells can be isolated from a subject following maturation, and these cells can be used to form hybridoma cells, as is known in the art.

The present invention is also directed to isolated antibodies raised against a polypeptide according to the present invention, or a binding fragment thereof. According to certain embodiments of the present invention, the antibody can be present in a polyclonal antiserum or a monoclonal preparation.

The isolated antibodies of the present invention may comprise an immunoglobulin heavy chain of any isotype (e.g., IgG, IgE, IgM, IgD, IgA, and IgY), class (e.g., IgG1, IgG2, IgG3, IgG4, IgA1 and IgA2) or subclass of immunoglobulin molecule. The isolated antibody can be a full length antibody, monoclonal antibody (including full length monoclonal antibody), polyclonal antibody, multispecific antibody (e.g., bispecific antibody), human, humanized or chimeric antibody, and antibody fragments, e.g., Fab fragments, F(ab') fragments, fragments produced by a Fab expression library, epitope-binding fragments of any of the above, and engineered forms of antibodies, e.g., scFv molecules, so long as they exhibit the desired neutralizing activity.

As noted above, the monoclonal antibody of the present invention can be a humanized antibody. Humanized antibodies are antibodies that contain minimal sequences from non-human (e.g., murine) antibodies within the variable regions. Such antibodies are used therapeutically to reduce antigenicity and human anti-mouse antibody responses when administered to a human subject.

An antibody can be humanized by substituting the complementarity determining region (CDR) of a human antibody with that of a non-human antibody (e.g., mouse, rat, rabbit, hamster, etc.) having the desired specificity, affinity, and capability (Jones et al., "Replacing the Complementarity-Determining Regions in a Human Antibody With Those From a Mouse," *Nature* 321:522-525 (1986); Riechmann et al., "Reshaping Human Antibodies for Therapy," *Nature* 332: 323-327 (1988); Verhoeyen et al., "Reshaping Human Antibodies: Grafting an Antilysozyme Activity," *Science* 239: 1534-1536 (1988), which are hereby incorporated by reference in their entirety). The humanized antibody can be further modified by the substitution of additional residues either in the Fv framework region and/or within the replaced non-human residues to refine and optimize antibody specificity, affinity, and/or capability.

Polyclonal antibodies can be prepared by any method known in the art. Polyclonal antibodies can be raised by immunizing an animal (e.g., a rabbit, rat, mouse, donkey, etc.) with multiple subcutaneous or intraperitoneal injections of the relevant antigen (e.g., an isolated scaffold polypeptide, fusion protein, or immunogenic conjugate) diluted in sterile saline and combined with an adjuvant (e.g., Complete or Incomplete Freund's Adjuvant) to form a stable emulsion. The polyclonal antibody is then recovered from blood or ascites of the immunized animal. Collected blood is clotted, and the serum decanted, clarified by centrifugation, and assayed for antibody titer. The polyclonal antibodies can be purified from serum or ascites according to standard methods in the art including affinity chromatography, ion-exchange chromatography, gel electrophoresis, dialysis, etc. Polyclonal antiserum can also be rendered monospecific using standard procedures (see e.g., Agaton et al., "Selective Enrichment of Monospecific Polyclonal Antibodies for Antibody-Based Proteomics Efforts," *J Chromatography A* 1043 (1):33-40 (2004), which is hereby incorporated by reference in its entirety).

Monoclonal antibodies can be prepared using hybridoma methods, such as those described by Kohler and Milstein, "Continuous Cultures of Fused Cells Secreting Antibody of Predefined Specificity," *Nature* 256:495-7 (1975), which is hereby incorporated by reference in its entirety. Using the hybridoma method, a mouse, hamster, or other appropriate host animal, is immunized to elicit the production by lymphocytes of antibodies that will specifically bind to an immunizing antigen. Alternatively, lymphocytes can be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against the scaffold, as determined by immunoprecipitation, immunoblotting, or by an in vitro binding assay such as radioimmunoassay (RIA) or enzyme-linked immunosorbent assay (ELISA) can then be propagated either in in vitro culture using standard methods (JAMES W. GODING, MONOCLONAL ANTIBODIES: PRINCIPLES AND PRACTICE (Academic Press 1986), which is hereby incorporated by reference in its entirety) or in vivo as ascites tumors in an animal. The monoclonal antibodies can then be purified from the culture medium or ascites fluid as described for polyclonal antibodies above.

Alternatively monoclonal antibodies can also be made using recombinant DNA methods as described in U.S. Pat. No. 4,816,567 to Cabilly et al, which is hereby incorporated by reference in its entirety. Polynucleotides encoding a monoclonal antibody are isolated, from mature B-cells or hybridoma cell, by RT-PCR using oligonucleotide primers that specifically amplify the genes encoding the heavy and light chains of the antibody. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries as described (McCafferty et al., "Phage Antibodies: Filamentous Phage Displaying Antibody Variable Domains," *Nature* 348:552-554 (1990); Clackson et al., "Making Antibody Fragments Using Phage Display Libraries," *Nature*, 352:624-628 (1991); and Marks et al., "By-passing Immunization. Human Antibodies from V-gene Libraries Displayed on Phage," *J Mol Biol* 222: 581-597 (1991), which are hereby incorporated by reference in their entirety).

The polynucleotide(s) encoding a monoclonal antibody can further be modified in a number of different ways using recombinant DNA technology to generate alternative antibodies. In one embodiment, the constant domains of the light and heavy chains of, for example, a mouse monoclonal antibody can be substituted for those regions of a human antibody to generate a chimeric antibody. Alternatively, the constant domains of the light and heavy chains of a mouse monoclonal antibody can be substituted for a non-immunoglobulin polypeptide to generate a fusion antibody. In other embodiments, the constant regions are truncated or removed to generate the desired antibody fragment of a monoclonal antibody. Furthermore, site-directed or high-density mutagenesis of the variable region can be used to optimize specificity and affinity of a monoclonal antibody.

The present invention also relates to a pharmaceutical composition comprising a pharmaceutically acceptable carrier and an antibody, or a binding fragment thereof, according to the present invention. The antibodies are raised against a polypeptide of the present invention, and their binding fragments are derived from those antibodies. In certain embodiments the composition comprises antibodies, or binding fragments thereof, that specifically bind and neutralize HIV-1, Influenza virus, Dengue Virus, Rotavirus, or *Neisseria meningitides*.

The polypeptide, DNA molecule, expression vector, antibody (or binding fragment thereof) of the present invention, and pharmaceutical compositions or vaccines comprising the same can be incorporated into a delivery vehicle to facilitate administration. Such delivery vehicles include, but are not limited to, biodegradable microspheres (MARK E. KEEGAN & W. MARK SALTZMAN, *Surface Modified Biodegradable Microspheres for DNA Vaccine Delivery, in* DNA VACCINES: METHODS AND PROTOCOLS 107-113 (W. Mark Saltzman et al., eds., 2006), which is hereby incorporated by reference in its entirety), microparticles (Singh et al., "Nanoparticles and Microparticles as Vaccine Delivery Systems," *Expert Rev Vaccine* 6(5):797-808 (2007), which is hereby incorporated by reference in its entirety), nanoparticles (Wendorf et al., "A Practical Approach to the Use of Nanoparticles for Vaccine Delivery," *J Pharmaceutical Sciences* 95(12):2738-50 (2006) which is hereby incorporated by reference in its entirety), liposomes (U.S. Patent Application Publication No. 2007/0082043 to Dov et al. and Hayashi et al., "A Novel Vaccine Delivery System Using Immunopotentiating Fusogenic Liposomes," *Biochem Biophys Res Comm* 261(3): 824-28 (1999), which are hereby incorporated by reference in their entirety), collagen minipellets (Lofthouse et al., "The Application of Biodegradable Collagen Minipellets as Vaccine Delivery Vehicles in Mice and Sheep," *Vaccine* 19(30):4318-27 (2001), which is hereby incorporated by reference in it entirety), and cochleates (Gould-Fogerite et al., "Targeting Immune Response Induction with Cochleate and Liposome-Based Vaccines," *Adv Drug Deliv Rev* 32(3):273-87 (1998), which is hereby incorporated by reference in its entirety).

For prophylactic treatment against viral or bacterial infection, it is intended that the composition(s) of the present invention can be administered prior to exposure of an individual to the virus or bacteria and that the resulting immune response can inhibit or reduce the severity of the viral or bacterial infection such that the virus or bacteria can be eliminated from the individual. The pharmaceutical compositions of the present invention can also be administered to an individual for therapeutic treatment. In accordance with one embodiment, it is intended that the composition(s) of the present invention can be administered to an individual who is already exposed to the virus or bacteria. The resulting enhanced immune response can reduce the duration or severity of the existing viral or bacterial infection, as well as minimize any harmful consequences of untreated viral or bacterial infections. The composition(s) can also be administered in combination other therapeutic anti-viral or anti-bacterial regimen. In asymptomatic patients, treatment can begin at any age (e.g., 10, 20, 30 years of age). Treatment typically entails multiple dosages over a period of time. Treatment can be monitored by assaying antibody, or activated T-cell or B-cell responses to the therapeutic agent over time. If the response falls, a booster dosage is indicated.

In prophylactic applications, pharmaceutical compositions containing the immunogenic peptides are administered to a patient susceptible to, or otherwise at risk of, the particular viral or bacterial infection in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, compositions containing an antibody according to the present invention are administered to a patient suspected of, or already suffering from, such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

The presence of a humoral immunological response can be determined and monitored by testing a biological sample (e.g., blood, plasma, serum, urine, saliva feces, CSF or lymph fluid) from the subject for the presence of antibodies directed to the immunogenic tau peptide. Methods for detecting antibodies in a biological sample are well known in the art, e.g., ELISA, Dot blots, SDS-PAGE gels or ELISPOT. The presence of a cell-mediated immunological response can be determined by proliferation assays ($CD4^+$ T cells) or CTL (cytotoxic T lymphocyte) assays which are readily known in the art.

Effective doses of the compositions of the present invention, for the treatment of the above described viral or bacterial infections vary depending upon many different factors, including mode of administration, target site, physiological state of the patient, other medications administered, and whether treatment is prophylactic or therapeutic. Treatment dosages need to be titrated to optimize safety and efficacy. The amount of immunogen depends on whether adjuvant is also administered, with higher dosages being required in the absence of adjuvant. The amount of an immunogen for administration sometimes varies from 1-500 µg per patient and more usually from 5-500 µg per injection for human administration. Occasionally, a higher dose of 1-2 mg per injection is used. Typically about 10, 20, 50, or 100 µg is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for each microgram of immunogen. The timing of injections can vary significantly from once a day, to once a year, to once a decade. On any given day that a dosage of immunogen is given, the dosage is greater than 1 µg/patient and usually greater than 10 µg/patient if adjuvant is also administered, and greater than 10 µg/patient and usually greater than 100 µg/patient in the absence of adjuvant. A typical regimen consists of an immunization followed by booster injections at time intervals, such as 6 week intervals. Another regimen consists of an immunization followed by booster injections 1, 2, and 12 months later. Another regimen entails an injection every two months for life. Alternatively, booster injections can be on an irregular basis as indicated by monitoring of immune response.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly, or yearly. In some methods, dosage is adjusted to achieve a plasma antibody concentration of 1-1000 µg/ml and in some methods 25-300 µg/ml. Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 μg to 10 mg, or 30-300 μg DNA per patient. Doses for infectious viral vectors vary from 10-100, or more, virions per dose.

Yet another aspect of the present invention relates to an assay for detecting reactivity between a polypeptide of the present invention and a broadly neutralizing antibody. The assay includes contacting the polypeptide with the broadly neutralizing antibody, and determining whether the broadly neutralizing antibody binds specifically to the polypeptide. This can be achieved using a labeled polypeptide or a labeled broadly neutralizing antibody.

Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, beta-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The immunoassay can be performed according to any suitable assay format. Examples of suitable assays to detect specific binding between a polypeptide of the invention and a neutralizing antibody include, but are not limited to, ELISA, radioimmunoassay, gel-diffusion precipitation reaction assay, immunodiffusion assay, agglutination assay, fluorescent immunoassay, and immunoelectrophoresis assay.

In a further aspect of the invention, a polypeptide of the invention that binds specifically to a neutralizing antibody that targets a discontinuous epitope of a pathogen can be used to screen serum for the presence of neutralizing antibodies following vaccination of an individual. The method of detecting a neutralizing antibody in serum includes contacting a labeled polypeptide of the present invention with serum from an individual; and detecting whether the polypeptide binds specifically to an antibody present in the serum, wherein said detecting is carried out using the label. Suitable labels and immunoassay formats include those identified above.

EXAMPLES

The following examples illustrate various compositions and methods of the invention. The examples are intended to illustrate, but in no way limit, the scope of the invention.

Example 1

Generation of FNfn10, Two-Loop Display Library

A FNfn10 scaffold was cloned into pAP-III6FL vector (a derivative of pAP-III6 containing a full-length gene III from bacteriophage M13) downstream of a Flag epitope sequence. The resulting plasmid was introduced into CJ236 E. coli host cells and single-stranded DNA template containing uracil was produced by infection with VCS M13 helper phage. Single-stranded phage DNA was purified and annealed to mutagenic oligonucleotides as described by Tonikian et al., "Identifying Specificity Profiles for Peptide Recognition Modules from Phage-Displayed Peptide Libraries," Nat. Protoc. 2(6):1368-86 (2007), which is hereby incorporated by reference in its entirety. The entire annealed and extended template mix was purified on a PCR clean-up resin (Sigma) and electroporated into TG1 cells (Stratagene). Ampicillin resistant transformants were suspended in LB medium, diluted to ~5×10$^7$ cells/ml and grown at 37° C. for two hours. Ten ml of the culture was infected with helper phage for two hours and then diluted into 100 ml of LB containing ampicillin and kanamycin and grown overnight at 30° C. Phage were harvested from the supernatant by precipitation with polyethylene glycol, resuspended in TBS containing 0.5% casein and 15% glycerol and frozen in aliquots at −80° C.

Beta strands A-G of the FNfn10 molecular scaffold are shown in FIG. 1A, along with the 3 discontinuous surface exposed loops that can be randomized (BC, FG and DE). This structure was generated using CN3D using the source data file MMDB IB 57520. The sequence of the mature FNfn10 protein (after proteolytic removal of the N-terminal MQ residues) is shown in FIG. 1C. The BC (Asp23-Val29) and FG (Gly77-Ser84) loops are in boldface. The DE loop is located from residues 52 thru 55.

Mutagenic oligonucleotides were used to simultaneously diversify the exposed BC loop and FG loop domains on the FNfn10 scaffold of FIG. 1C, thereby generating a library in which two discontinuous exposed loops were diversified (FIGS. 1A-B). Oligonucleotide sequences (reverse complement of the coding strand for BC1, BC2, FG1 and FG2) of the modified loops were:

```
Library 1 (KMT codon, FIG. 1B)
BC1:
                                        (SEQ ID NO: 130)
5'-CGTGATACGGTAATAACG(AKM)₇CCAGCTGATCAGGCT-3'

FG1:
                                        (SEQ ID NO: 131)
5'-AATCGAGATTGGCTTGGA(AKM)₈AGTAACAGCGTATACAGTGAT-3'

Library 2 (NHK codon; TAG suppressed to Y, FIG. 1B)
BC2:
                                        (SEQ ID NO: 132)
5'-CGTGATACGGTAATAACG(MDN)₇CCAGCTGATCAGGCT-3'

FG2:
                                        (SEQ ID NO: 133)
5'-AATCGAGATTGGCTTGGA(MDN)₈AGTAACAGCGTATACAGTGAT-3'

Library 3 (Tri, mixture of 19 codons excluding
Cys (Glen Research), FIG. 1B)
BC3:
                                        (SEQ ID NO: 134)
5'-CTGATCAGCTGG(TRI)₇CGTTATTACCGT-3'

FG3:
                                        (SEQ ID NO: 135)
5'-TACGCTGTTACT(TRI)₈TCCAAGCCAATC-3'

Library 4 (Tri-C, Tri with Cys-Cys bond between
BC-FG loops, FIG. 1B)
BC4:
                                        (SEQ ID NO: 136)
5'-CTGATCAGCTGG(TRI)₆TGTCGTTATTACCGT-3'

FG4:
                                        (SEQ ID NO: 137)
5'-TACGCTGTTACTTGC(TRI)₇TCCAAGCCAATC-3'
```

Four libraries were generated: (A) Lib1 used BC1 & FG1, and consisted of ~1×10$^7$ clones, (B) Lib2 used BC2 & FG2, and consisted of ~4×10⁷ clones. Before selection, the two libraries were mixed in a 4:1 ratio (B:A) Libraries 3 and 4 were generated using oligonucleotides containing triphospharamadite (Trimer) codon mixtures (TRI) that consisted of a mixture of 19 codons (excluding cysteine). Library 3 was derived using oligonucleotides BC3 and FG3 and consisted of ~1×10⁹ clones. Library 4 consisted of ~2×10⁸ clones using oligonucleotides BC4 and FG4, but incorporated two cysteine residues at the end of the loops to form a disulfide bridge to hold the loops together (Lipovsek et al., "Evolution of an Interloop Disulfide Bond in High-affinity Antibody Mimics Based on Fibronectin Type III Domain and Selected by Yeast Surface Display: Molecular Convergence with Single-domain Camelid and Shark Antibodies," $J$ $Mol$ $Biol$ 368(4): 1024-41 (2007), which is hereby incorporated by reference in its entirety). Both of these latter libraries utilized a modified vector that inverted the gene III expression region with respect to the M13 origin of replication due to the fact that the Trimer containing oligonucleotides are only available in the sense strand.

Example 2

Library Selection Against MAb b12

The b12 Mab was immobilized in two microtiter dish wells at 50 µg/ml in TBS and after blocking with casein; 50 µl of the combined library was added to each well (~5×10¹¹ total phage) and the plate was shaken for 2 hours at room temp. The phage were then removed and the wells were washed 7 times with TBS+0.1% Tween 20, once with water, and eluted for 15 minutes with 0.1 M glycine HCl, pH 2, containing 0.1% bovine serum albumin. The eluate was removed from the wells and neutralized with Tris base. The eluted phage were transduced into TG1 and plated overnight. The colonies were scraped from the plates and inoculated into fresh medium for production of the next round phage stock, as described above. For rounds 2 and 3 of the enrichment, a single b12-coated well was used. Individual clones from the second and third rounds of enrichment were tested by phage ELISA to confirm binding to b12 and lack of reactivity with a myeloma IgG1 protein. Positive clones were PCR amplified and sequenced.

The data show that: (i) Mab b12-binding proteins can be readily isolated using these novel FNfn10-based libraries (see FIGS. 2, 3, 7, 8 and 9) and (ii) that the proteins isolated show no homology to b12 mimotopes previously identified using conventional phage display technology (see, e.g., FIGS. 8 and 9) (Zwick et al., "Identification and Characterization of a Peptide that Specifically Binds the Human, Broadly Neutralizing Anti-human Immunodeficiency Virus Type 1 Antibody b12," $J$ $Virol$. 75(14):6692-9 (2001); Dorgham et al., "Immunogenicity of HIV Type 1 gp120 CD4 Binding Site Phage Mimotopes," $AIDS$ $Res$ $Hum$ $Retroviruses$ 21(1):82-92 (2005); Zwick et al., "Molecular Features of the Broadly Neutralizing Immunoglobulin G1 b12 Required for Recognition of Human Immunodeficiency Virus Type 1 gp120," $J$ $Virol$. 77(10):5863-76 (2003), which are hereby incorporated by reference in their entirety). Importantly, sequences of previously identified b12 Mab binding mimotope peptides (that were independently derived by two different laboratories using conventional linear peptide display libraries) contain a core FSD or WSD motif (Dorgham et al., "Immunogenicity of HIV Type 1 gp120 CD4 Binding Site Phage Mimotopes," $AIDS$ $Res$ $Hum$ $Retroviruses$ 21(1):82-92 (2005); Saphire et al., "Structure of a High-affinity "Mimotope" Peptide Bound to HIV-1-Neutralizing Antibody b12 Explains its Inability to Elicit gp120 Cross-reactive Antibodies," $J$ $Mol$ $Biol$. 369(3): 696-709 (2007), which are hereby incorporated by reference in their entirety), which is essential for binding to b12 (Saphire et al., "Structure of a High-affinity "Mimotope" Peptide Bound to HIV-1-Neutralizing Antibody b12 Explains its Inability to Elicit gp120 Cross-reactive Antibodies," $J$ $Mol$ $Biol$. 369(3):696-709 (2007), which is hereby incorporated by reference in its entirety). This FSD/WSD core peptide is not present in any of the b12-binding peptides that have been identified (see FIGS. 8 and 9).

Example 3

Analysis of FNfn10 Clones Selected for the Ability to Bind to the b12 Mab

Selected FNfn10 clones were produced as soluble recombinant proteins, and tested for their ability to bind to the b12 Mab. To do this, the FNfn10 constructs were expressed as C-terminal biotinylated proteins by removal of the gene III encoding fragment and appending a birA substrate peptide sequence to the C-terminus of the protein. Beckett et al., "A Minimal Peptide Substrate in Biotin Holoenzyme Synthetase-catalyzed Biotinylation," $Protein$ $Sci$. 8(4):921-9 (1999) and Schatz, "Use of Peptide Libraries to Map the Substrate Specificity of a Peptide-modifying Enzyme: A 13 Residue Consensus Peptide Specifies Biotinylation in $Escherichia$ $coli$," $Biotechnology$ (NY) 11(10):1138-43 (1993), which are hereby incorporated by reference in their entirety. Co-expression of the modified FNfn10 gene with the birA gene (on a compatible plasmid) resulted in production of a $His_6$-tagged Flag-FN-bio protein that was purified from whole cell lysates with magnetic beads derivatized with a Ni+2 chelate (Novagen) using a Thermo KingFisher magnetic bead processing workstation. The purified FN-bio protein was eluted from the beads with imidazole and stored at 4° C. in elution buffer until use.

Figure 2:
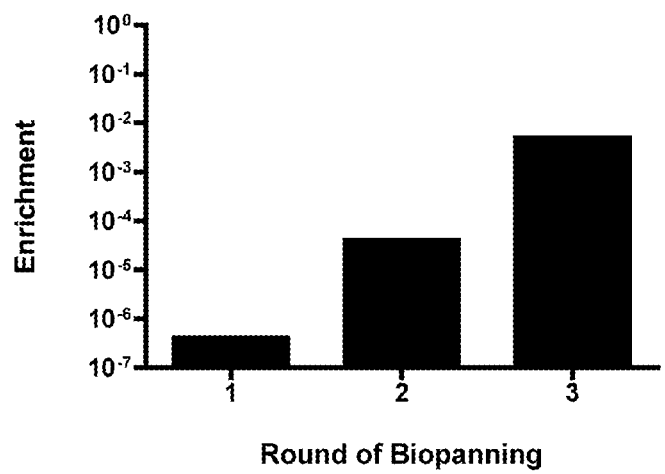
FIG. 2 is a bar graph that illustrates selection of Mab b12 binding clones from the FNfn10 two loop library. As shown, the FNfn10 two loop display library was screened in three rounds of biopanning against immobilized Mab b12. The increase in enrichment between the initial and final rounds of biopanning was >10,000 fold.
Figure 3:
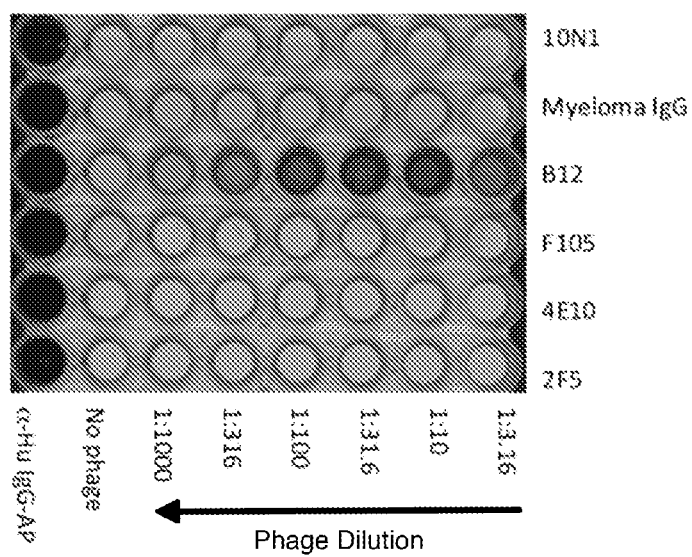
FIG. 3 illustrates the specificity of a representative Mab b12 binding clone. Mabs were coated at 5 μg/ml. Phage were PEG precipitated from 1.2 ml cultures, re-suspended in 0.3 ml in TBS+0.5% casein and 50 μl was added to the wells. After 1 hour incubation at RT, the wells were washed 10×, and diluted anti-M13-HRP conjugate was added for 1 hour. After washing, HRP substrate (TMB) was added. The results show that the phage is highly specific for b12 and does not recognize other Mabs specific for different domains on the HIV-1 envelope (F105, 4E10, 2F5) or irrelevant proteins (10N1, myeloma IgG).
Figure 4:
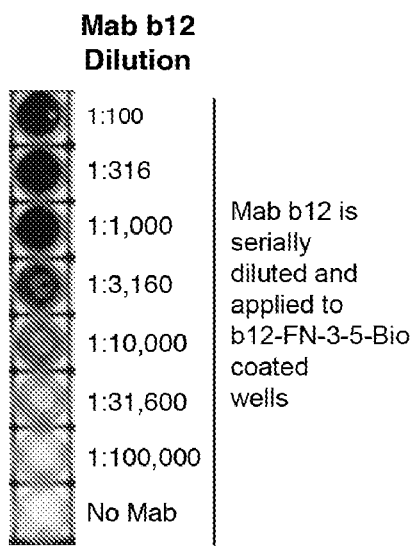
FIG. 4 shows the results of an ELISA assay, which illustrates that purified b12-FN-3-5 protein binds to Mab b12. Purified, biotinylated protein corresponding to a representative b12 Mab-binding FNfn10 clone (b12-FN-3-5) was bound to streptavidin coated wells. After extensive washing, serially diluted IgG1 b12 Mab (starting at a concentration of 10 μg/ml) was then added to the bio-b12-FN-3-5 coated wells. The plate was incubated, washed thoroughly, and bound IgG1 b12 Mab was detected using an AP conjugated anti-human IgG. The results show that the b12 Mab binds efficiently to the purified b12-FN-3-5 protein.

This purified FN-bio protein was used to perform an ELISA assay, to assess the ability of the purified protein to bind to HIV-1 gp120. This analysis was performed using purified, biotinylated protein corresponding to a representative Mab b12-binding FNfn10 clone, designated b12-FN-3-5 (BC loop=VHFALPV (SEQ ID NO:13); FG loop=HISHQHIL (SEQ ID NO:14)). Briefly, purified biotinylated b12-FN-3-5 protein was bound to streptavidin coated wells, and serially diluted IgG1 b12 Mab was added to the b12-FN-3-5 coated wells, starting at a concentration of 10 µg/ml. Bound IgG1 b12 Mab was then detected using an AP-conjugated anti-human IgG. FIG. 4 shows that the purified b12-FN-3-5 protein bound efficiently to the b12 Mab.

Figure 5:
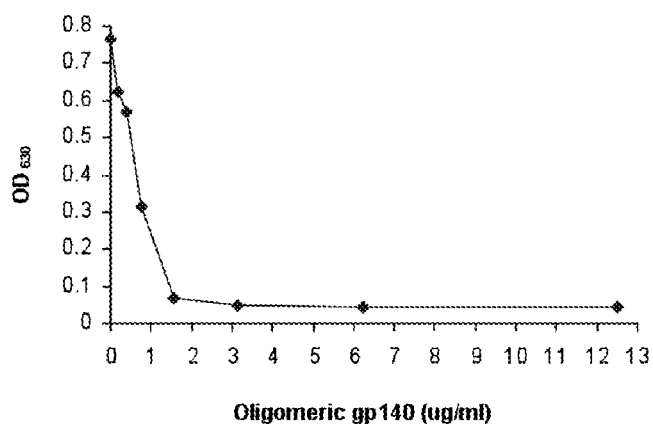

A follow-up competition ELISA was performed, using the same b12-FN-3-5 protein. To do this, the biotinylated b12-FN-3-5 protein was again pre-bound to streptavidin coated wells. After this, a fixed concentration of b12 IgG1 Mab was pre-incubated in the presence of varying amounts of oligomeric HIV-1 gp140 (YU-2) (serial two-fold dilutions, starting at 12.5 µg/ml and ending at 0.2 µg/ml; see FIG. 11 for biochemical characterization of the oligomeric gp140 used in this experiment). This material was then added to the b12-FN-3-5 coated wells, and binding of the IgG1 b12 Mab was detected using an AP conjugated anti-human IgG. FIG. 5 shows that oligomeric gp140 competitively inhibited the binding of the b12 Mab to the plate-bound b12-FN-3-5 protein. Collectively, these findings strongly underscore the uniqueness of this novel molecular scaffold and provide strong support for this approach.

Example 4

Figure 7:
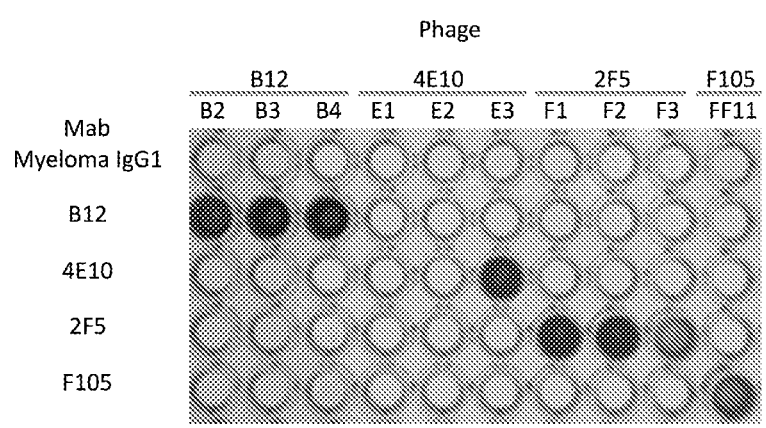
Figure 8:
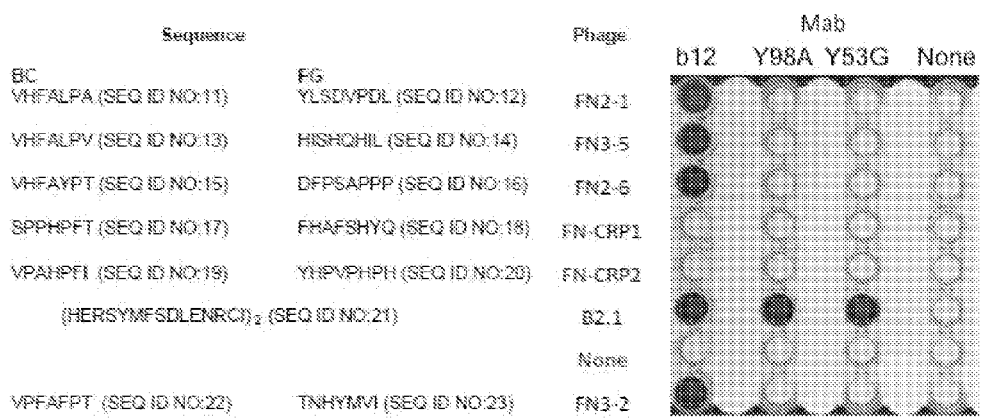

Generalizable Utility of the FNfn10 Two Loop Display Library for Identification of Other BNA Mimotopes The FNfn10 display scaffold can also be used to identify antigenic mimics of other discontinuous, virus-neutralizing epitopes within the HIV-1 Env glycoprotein. The generalizable utility of the FNfn10 scaffold is a major asset of this technology, and is supported by screening results that were obtained with the FNfn10 two loop display library (FIGS. 7 and 8). The importance of these findings is that they indicate that one will be able to extend future work to the development of antigenic mimics of other neutralizing epitopes (Scheid et al., "Broad Diversity of Neutralizing Antibodies Isolated From Memory B Cells in HIV-infected Individuals," *Nature* 458(7238):636-40 (2009); Li et al., "Analysis of Neutralization Specificities in Polyclonal Sera Derived from Human Immunodeficiency Virus Type 1-infected Individuals," *J Virol.* 83(2):1045-59 (2009); Gray et al., "Antibody Specificities Associated with Neutralization Breadth in Plasma from Human Immunodeficiency Virus Type 1 Subtype C-infected Blood Donors," *J Virol.* 83(17):8925-37 (2009); Binley et al., "Profiling the Specificity of Neutralizing Antibodies in a Large Panel of Plasmas from Patients Chronically Infected with Human Immunodeficiency Virus Type 1 Subtypes B and C," *J Virol.* 82(23):11651-68 (2008); Pantophlet, "GP120: Target for Neutralizing HIV-1 Antibodies," *Annu Rev Immunol.* 24:739-69 (2006), which are hereby incorporated by reference in their entirety), including conformational epitopes on Env trimers (Walker et al., "Broad and Potent Neutralizing Antibodies from an African Donor Reveal a New HIV-1 Vaccine Target," *Science* 326(5950:285-289 (2009), which is hereby incorporated by reference in its entirety), as well as epitopes derived from the glycan shield of the envelope (Hessell et al., "Broadly Neutralizing Human Anti-HIV Antibody 2G12 is Effective in Protection Against Mucosal SHIV Challenge Even at Low Serum neutralizing Titers," *PLOS Pathog.* 5(5):e1000433 (2009), which is hereby incorporated by reference in its entirety).

Figure 6:
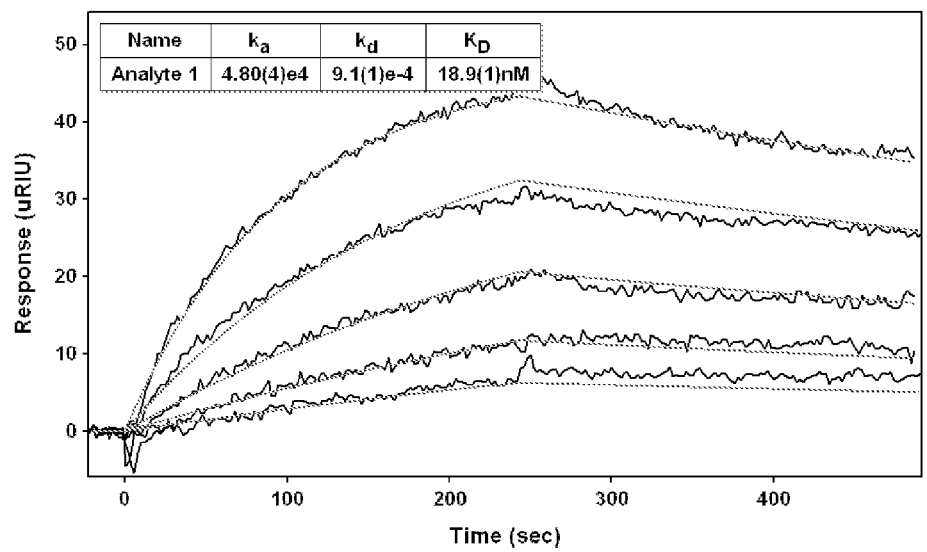

Briefly, the pilot FNfn10 two loop display library was selected against HIV-1 Env specific, virus neutralizing monoclonal antibodies directed against conformational epitopes located on the membrane-proximal envelope region (MPER) of gp41 (2F5, 4E10) or at the CD4 binding site of gp120 (F105) (Montero et al., "The Membrane-proximal External Region of the Human Immunodeficiency Virus Type 1 Envelope: Dominant Site of Antibody Neutralization and Target for Vaccine Design," *Microbiol Mol Biol Rev.* 72(1):54-84, table of contents (2008); Muster et al., "A Conserved Neutralizing Epitope on gp41 of Human Immunodeficiency Virus Type 1," *J Virol.* 67(11):6642-7 (1993); Posner et al., "Neutralization of HIV-1 by F105, a Human Monoclonal Antibody to the CD4 Binding Site of gp120," *J Acquir Immune Defic Syndr.* 6(1):7-14 (1993); Posner et al., "An IgG Human Monoclonal Antibody that Reacts with HIV-1/GP120, Inhibits Virus Binding to Cells, and Neutralizes Infection. *J Immunol.* 146(12):4325-32 (1991), which are hereby incorporated by reference in their entirety). Selection was successful against each of these Mab targets. Individual phage clones derived from this selection process were then tested for their ability to bind to the indicated immobilized HIV-1 Env specific Mabs or an irrelevant IgG1 Mab, using an ELISA assay (FIG. 7). In addition, FIG. 6 shows kinetic analysis of binding of b12 3-5 FN to b12 Mab. Monoclonal antibody b12 was coupled to the surface of a Reichert gold sensor slide and binding of dilutions of the FN were monitored by surface plasmon resonance on a Reichert SR7000DC instrument. Kinetic analysis of binding was evaluated using Scrubber2.0a (Biologic Software Pty., Australia).

It can be readily appreciated that phage clones were identified that bound specifically to each of the selecting Mabs, but not to unrelated/irrelevant Mabs (exemplified by clone E3 for the 4E10 Mab, clones F1-F3 for the 2F5 Mab and clone FF11 for the F105 Mab; the b12-binding clones are included here as controls). Additional data strongly suggest that at least some of the clones derived bind to the b12 paratope (FIGS. 8, 9 and 10A-B).

Briefly, experiments were conducted to test whether the identified b12-binding FNfn10 proteins bind Mab b12 through interactions that do not recapitulate those which drive binding to HIV-1 Env. This problem has previously been described for the well-characterized b12 peptide mimotope, B2.1 (Zwick et al., "Molecular Features of the Broadly Neutralizing Immunoglobulin G1 b12 Required for Recognition of Human Immunodeficiency Virus Type 1 gp120," *J Virol.* 77(10):5863-76 (2003), which is hereby incorporated by reference in its entirety). Peptide B2.1 (SEQ ID NO:21) was derived by selection of a conventional phage display against b12, and it contacts b12 via three contiguous critical binding residues (CBRs) that do not authentically mimic the discontinuous critical binding residues involved in the binding of b12 to HIV-1 Env (Saphire et al., "Structure of a High-affinity "Mimotope" Peptide Bound to HIV-1-Neutralizing Antibody b12 Explains its Inability to Elicit gp120 Cross-reactive Antibodies," *J Mol Biol.* 369(3):696-709 (2007), which is hereby incorporated by reference in its entirety). As a result, the B2.1 peptide is not an authentic antigenic mimic of the b12 epitope on HIV-1 Env (Zwick et al., "Molecular Features of the Broadly Neutralizing Immunoglobulin G1 b12 Required for Recognition of Human Immunodeficiency Virus Type 1 gp120," *J Virol.* 77(10):5863-76 (2003); Saphire et al., "Structure of a High-affinity "Mimotope" Peptide Bound to HIV-1-Neutralizing Antibody b12 Explains its Inability to Elicit gp120 Cross-reactive Antibodies," *J Mol Biol.* 369(3):696-709 (2007), which are hereby incorporated by reference in their entirety).

The key CBR within the B2.1 peptide is a contiguous FSD motif, which is homologous to the WSD motif that was independently identified on b12-binding linear peptides by Dorgham and colleagues (Dorgham et al., "Immunogenicity of HIV Type 1 gp120 CD4 Binding Site Phage Mimotopes," *AIDS Res Hum Retroviruses* 21(1):82-92 (2005), which is hereby incorporated by reference in its entirety). Notably, this motif is absent in all of the b12-binding FN clones that have been identified to date, indicating that these clones contact b12 through a mechanism that is distinct from that identified for the B2.1 peptide (Zwick et al., "Identification and Characterization of a Peptide that Specifically Binds the Human, Broadly Neutralizing Anti-human Immunodeficiency Virus Type 1 Antibody b12," *J Virol.* 75(14):6692-9 (2001), which is hereby incorporated by reference in its entirety), and its independently derived, WSD-containing analogs (Dorgham et al., "Immunogenicity of HIV Type 1 gp120 CD4 Binding Site Phage Mimotopes," *AIDS Res Hum Retroviruses* 21(1):82-92 (2005), which is hereby incorporated by reference in its entirety).

It has now been directly tested whether the identified b12-binding FN clones can bind to mutant derivatives of Fab b12 that contain mutations at key residues, known to interfere with the ability of Fab b12 to bind to HIV-1 gp120 (e.g., W100A, Y98A, Y53G), but not to the previously described b12 peptide mimotope, B2.1 (Zwick et al., "Molecular Features of the Broadly Neutralizing Immunoglobulin G1 b12 Required for Recognition of Human Immunodeficiency Virus Type 1 gp120," *J Virol.* 77(10):5863-76 (2003), which is hereby incorporated by reference in its entirety). FIG. 8 shows that an initial set of b12-binding FN clones all bound to wild-type b12, but not to the Y98A or Y53G mutant antibodies. In contrast, the B2.1 phage (kindly provided by Jamie Scott) bound to all 3 antibodies, as previously described (Zwick et al., "Identification and Characterization of a Peptide that Specifically Binds the Human, Broadly Neutralizing Anti-human Immunodeficiency Virus Type 1 Antibody b12," *J Virol.* 75(14):6692-9 (2001); Saphire et al., "Structure of a High-affinity "Mimotope" Peptide Bound to HIV-1-Neutralizing Antibody b12 Explains its Inability to Elicit gp120 Cross-reactive Antibodies," *J Mol Biol.* 369(3):696-709 (2007); Zwick et al., "Molecular Features of the Broadly Neutralizing Immunoglobulin G1 b12 Required for Recognition of Human Immunodeficiency Virus Type 1 gp120," *J Virol.* 77(10):5863-76 (2003), which are hereby incorporated by reference in their entirety). These data demonstrate that the b12-binding FN clones engage the b12 antibody via similar contact residues to HIV-1 Env, and do not share the binding properties of the previously described b12-binding B2.1 peptide.

Figure 9:
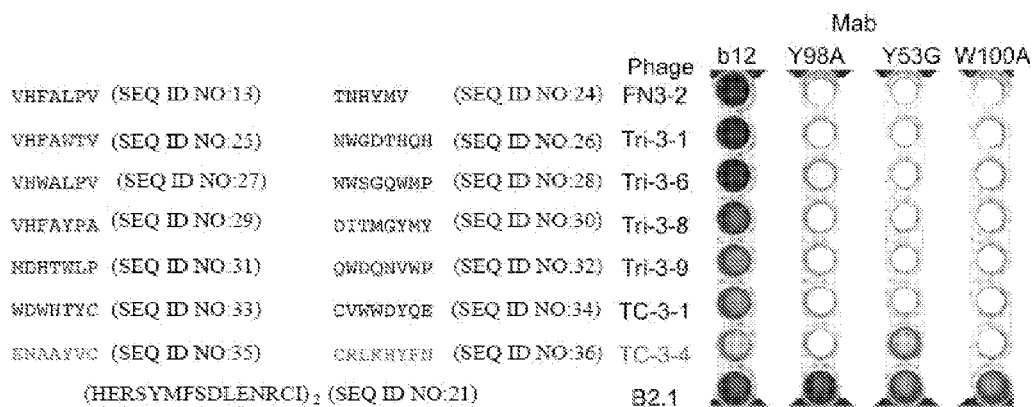

Analysis of additional b12-binding clones from other peptide libraries shows that these clones bound to wild-type b12, but not to the Y98A, Y53G or W100A mutant antibodies (FIG. 9). Only one clone, TC-3-4, bound weakly to the Y53G mutant—suggesting that it is does not contact the b12 antibody via the same residues that are used to bind to the HIV-1 Env glycoprotein.

Figure 10A:
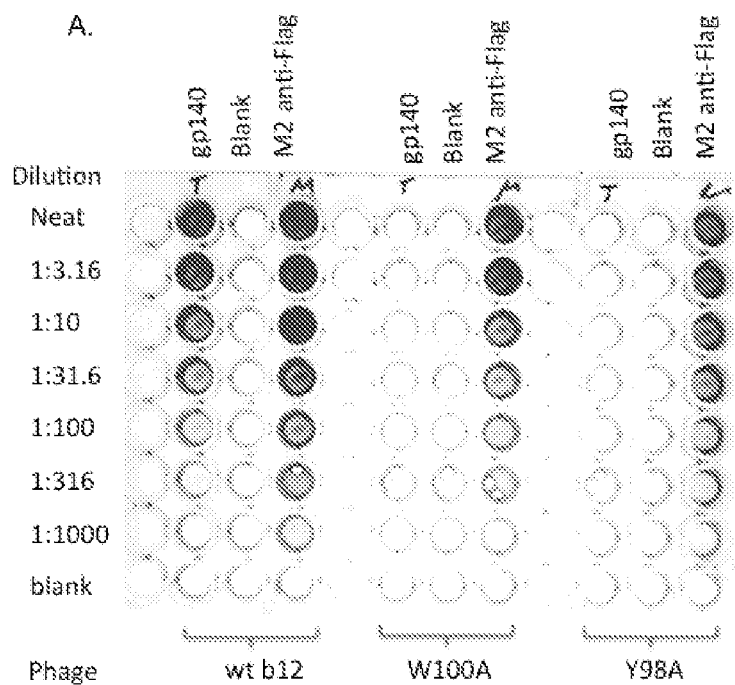
Figure 10B:
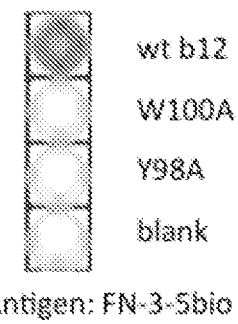

To confirm this interpretation, a control experiment was performed in which phage clones were constructed that displayed wild-type b12 scFv or one of two point mutant scFvs (Y98A, W100A) on their surface, and then the binding specificity of these phages were tested. This analysis confirmed that, as expected, only wt b12 was able to bind to oligomeric HIV-1 gp140 (FIG. 10A) (Zwick et al., "Molecular Features of the Broadly Neutralizing Immunoglobulin G1 b12 Required for Recognition of Human Immunodeficiency Virus Type 1 gp120," *J Virol.* 77(10):5863-76 (2003), which is hereby incorporated by reference in its entirety); in addition, this experiment also confirmed that only wt b12 scFv (and not the W100A or Y98A mutant scFvs) was able to bind to the b12-FN-3-5 protein (FIG. 10B).

Example 5

Production of Oligomeric HIV-1 Env Proteins

For competition ELISAs and for immunization studies, fibritin-stabilized HIV $Env_{gp140}$ oligomers derived from the neutralization-resistant YU2 primary R5 HIV-1 isolate was produced (Grundner et al., "Analysis of the Neutralizing Antibody Response Elicited in Rabbits by Repeated Inoculation with Trimeric HIV-1 Envelope Glycoproteins," *Virology* 331 (1):33-46 (2005); Grundner et al., "Factors Limiting the Immunogenicity of HIV-1 gp120 Envelope Glycoproteins," *Virology* 330(1):233-48 (2004); Yang et al., "Highly Stable Trimers Formed by Human Immunodeficiency Virus Type 1 Envelope Glycoproteins Fused with the Trimeric Motif of T4 Bacteriophage Fibritin," *J Virol.* 76(9):4634-42 (2002); Yang et al., "Improved Elicitation of Neutralizing Antibodies Against Primary Human Immunodeficiency Viruses by Soluble Stabilized Envelope Glycoprotein Trimers," *J Virol.* 75(3):1165-71 (2001); Yang et al., "Characterization of Stable, Soluble Trimers Containing Complete Ectodomains of Human Immunodeficiency Virus Type 1 Envelope Glycoproteins," *J Virol.* 74(12):5716-25 (2000); Yang et al., "Modifications that Stabilize Human Immunodeficiency Virus Envelope Glycoprotein Trimers in Solution," *J Virol.* 74(10): 4746-54 (2000), which are hereby incorporated by reference in their entirety).

Figures 11, 12:
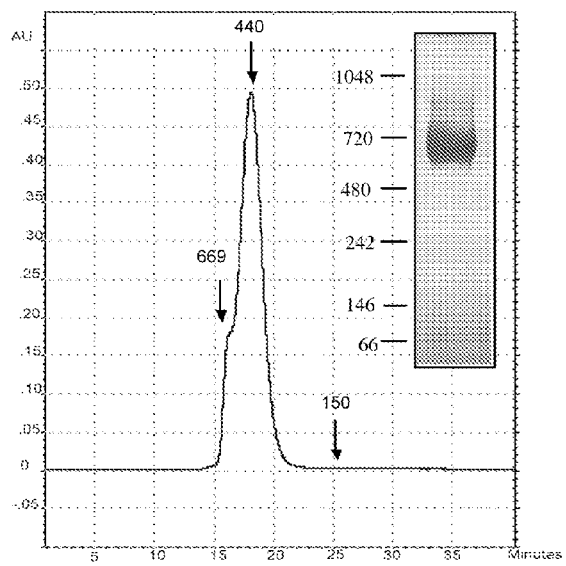

Purified YU2gp140 protein produced by transient transfection of 293 FreeStyle cells was run on gel filtration (Superdex 200; Amersham), and a fully resolved peak corresponding to approximately 440 kDa, consistent with a trimer, was observed (FIG. 11). A small portion of aggregates or dimer of trimers was observed, which is consistent with previous reports (Pancera et al., "Soluble Mimetics of Human Immunodeficiency Virus Type 1 Viral Spikes Produced by Replacement of the Native Trimerization Domain with a Heterologous Trimerization Motif: Characterization and Ligand Binding Analysis," *J Virol.* 79(15):9954-69 (2005), which is hereby incorporated by reference in its entirety). The purified trimer was analyzed on native gel migrating as a single band with an apparent molecular mass of ~600 kDa as compared to molecular weight calibration proteins (FIG. 11, inset panel). However, the apparent molecular mass on the native gel is likely an overestimate since non-globular proteins, like gp120, do not migrate as do the globular molecular weight calibration standards in the native gel. Overall, the analyses by gel filtration chromatography and native gel confirm the trimeric nature of the purified YU2gp140 protein. These data also highlight the lack of monomeric gp140 in the oligomers (see FIG. 11, inset panel). This is important with respect to the proposed competition ELISA experiments.

Screening of the pilot FNfn10 two loop display library against Mab b12 will be completed, using methods that are outlined in Examples 1-6. All b12-reactive clones will be "negatively" screened against at least two unrelated human IgG1 Mabs, to ensure specificity for b12 (see Examples 1-6). As shown in Example 7 below, the b12-specific scaffold FN 3-5 was screened against gp140 trimer for binding activity. Other b12-reactive clones can be similarly screened against gp140.

Example 6

Identification of Mimics of the Broadly Neutralizing "Fusion Pocket" Epitope in the IAV Hemagglutinin Identification of mimics of the discontinuous, broadly neutralizing "fusion pocket" epitope in HA was accomplished by in vitro screening of diversified discontinuous protein libraries, constructed using a unique display scaffold, and presented on the surface of bacteriophage. The libraries were screened against the well-characterized human monoclonal antibodies F10 and D8 (FIG. 12), which are known to bind to this epitope, as are other antibodies whose CDR1 and CDR2 region sequences are shown in FIG. 12. Hits were confirmed by a secondary screen against other antibodies known to also possess reactivity to this epitope (FIG. 12).

For screening purposes, influenza Mabs F10, D8 and other VH1-69 using antibodies may be modified to contain an arbitrary light chain, because binding to the HA antigen is mediated solely by the heavy chain of the Mab. Therefore, heavy chain from Mab D8 was paired with an arbitrary light chain, and then this antibody was used as a target for screening with randomized FN libraries. In this case, selected FN molecules contained modified BC and FG loop region sequences as follows: VFWDQWT (SEQ ID NO:163) (BC) and WMQWWEFQ (SEQ ID NO:164) (FG).

The heavy chain from Mab F10 was also paired with an arbitrary light chain (in this case the VK chain from the HIV-1 b12 Mab), and then this antibody was used as a target for screening with randomized FN libraries. In this case, selected FN molecules contained modified BC and FG loop region sequences as follows: QQPEDAAD (SEQ ID NO:165) and LPAPMELKSP (SEQ ID NO:167); KSSEFYP (SEQ ID NO:166) and SFSSLFVS (SEQ ID NO:168) (in each pair, the BC loop sequence is given first, followed by the FG loop sequence).

Materials and Methods for Example 7

Generation of b12 Mab Mutants

Monoclonal antibodies were generated by cloning synthetic fragments encoding the variable regions of b12 and three single amino acid mutants (Y98A, Y53G, and W100A in VH) into expression vectors gamma1-HC, kappa-LC and lamdba-LC for mammalian cell expression (Tiller et al., "Efficient Generation of Monoclonal Antibodies from Single Human B cells by Single Cell RT-PCR and Expression Vector Cloning," *J. Immunol. Methods* 329(1-2):112-24 (2008), which is hereby incorporated by reference in its entirety). Vectors were transiently transfected into HEK293 cells and the expressed proteins were purified on protein G magnetic beads.

Alanine Scanning Mutagenesis

Preparations of single alanine mutations at indicated positions of the b12 epitope surrogate BC and FG loops were grown BL21 (birA) cells, induced with IPTG and in the presence of 50 μM biotin, and biotinylated protein was purified by Thermo Kingfisher Purification machine. Purified FN was utilized in antibody ELISA analysis. Alanine mutations were introduced in a manner similar to the procedures described in Example 1 except that specific codons were mutated to encode an alanine residue prior to expression of the constructs.

Phage ELISA

Phage were prepared by PEG precipitation from 1.2 ml cultures, re-suspended in 0.3 ml in TBS+0.5% casein and 50 μL was added to the wells. After 1 hour of incubation at room temperature, the wells were washed 10 times and a 1:2000 dilution of anti-M13-HRP and conjugate was added for a 1 hour incubation. After washing, HRP substrate (TMB) was added. The wells were allowed to develop and the reactions were stopped by addition of 100 μL of sulfuric acid to each well after an image was acquired. At this point, the optical density was read at 420 nm.

Antibody ELISA

Purified FN epitope surrogates at 1 μg/mL were captured by streptavidin coated wells overnight. After washing with TBS, the wells were blocked with BlockerTM for two hours at RT. After washing with TBS, serial half-log dilutions of selected Mab were added to each well and incubated for an hour at RT. Addition of secondary goat-anti-human-HRP antibody followed by HRP substrate (TMB) was used for the development of the assay. The reactions were stopped by addition of 50 μL of sulfuric acid and the optical density was read at 420 nm.

b12 Competition ELISA

Purified, biotinylated protein corresponding to a representative b12 Mab-binding FNfn10 clone (b12 3-5 FN) was bound to streptavidin coated wells (Pierce), and washed with PBS+0.05% Tween (PBS-T). Serial 2-fold dilutions of oligomeric YU2gp140 or YU2gp140 D368R mutant, from 0.4 to 25 μg/ml, were preincubated with a fixed amount of IgG1 b12 Mab (1 μg/ml) at 37° C. for 30 min, before being added to b12 3-5 FN coated wells for 2 hours at RT. After washes with PBS-T, a secondary anti-human-IgG-HRP antibody was added at 1:5000 dilution for 1 hr at RT. Following five washes, the ELISAs were developed with 100 μl of TMB substrate. The reactions were stopped by adding 100 μl sulfuric acid to each well and the optical density at 450 nm was read. Each condition was repeated in duplicate.

2F5 and 4E10 Competition ELISA

2F5/4E10 peptide conjugated to BSA was coated at 5 μg/mL overnight onto polystyrene plates. A serial half log titration of the respective Mab was added sequentially to each well and developed as described in the Antibody ELISA section. A titration curve was created to determine the optimal concentration of Mab for the competition ELISA.

2F5/4E10 peptide conjugated to BSA was coated overnight at 5 μg/mL on polystyrene plates. After washing five times with TBS, the plates were blocked with Blocker TM for two hours at RT. 2F5 Mab (50 ng/mL) or 4E10 Mab (15.8 ng/mL) was pre-incubated with half log dilutions of 2F5 FN protein or 1F1 FN protein, or 4E10 5-2 FN, 4E10 5-5 FN, or 1F1 FN before addition to the coated plates. After extensive washing with TBS, Mab bound to the 2F5/4E10 peptide was detected with goat anti-human IgG-HRP conjugate at a 1:2000 dilution. HRP substrate (TMB) was used for the development of the assay and the reactions were stopped by addition of 50 μL of sulfuric acid to each well after an image was acquired. At this point, the optical density was read at 420 nm.

Example 7

Additional Epitope Surrogates Derived from a Fibronectin Scaffold-Generation of Antigen Mimics The library was generated using the procedures of Example 1, and libraries were screened for selection against HIV Mabs (b12, 447-52D, Z13, 4E10, 2F5, and VRC01) using the procedures of Example 2. Production and purification of selected FNfn10 clones was carried out as described in Example 3.

In particular, two distinct libraries of randomized BC and FG loops displayed on the FNfn10 scaffold were generated, as summarized in FIG. 1B. The libraries were selected against target monoclonal antibodies (Mab) with broadly neutralizing activity against HIV-1. Selection against Mab was completed in three iterative cycles to increase the representation of specific binders without drastically decreasing the heterogeneity of the population. Positive colonies obtained after three round of selection were then chosen for sequencing (Table 1).

TABLE 1

FNfn10 Scaffolds that Bind Specifically to Mabs

| MAb | BC Loop Sequence | FG Loop Sequence |
|---|---|---|
| b12 | VHFALPV (SEQ ID NO: 13) | TNHYMV (SEQ ID NO: 24) |
| | VHFALPV (SEQ ID NO: 13) | HISHQHIL (SEQ ID NO: 14) |
| | VHFAWTV (SEQ ID NO: 25) | NWGDTHQH (SEQ ID NO: 26) |
| | VHWALPV (SEQ ID NO: 27) | WWSGQWMP (SEQ ID NO: 28) |

TABLE 1-continued

FNfn10 Scaffolds that Bind Specifically to Mabs

| MAb | BC Loop Sequence | FG Loop Sequence |
|---|---|---|
| | VHFAYPA (SEQ ID NO: 29) | DITMGYMY (SEQ ID NO: 30) |
| | MDHTWLP (SEQ ID NO: 31) | QWDQNVWP (SEQ ID NO: 32) |
| Rtx | PKLGVNK (SEQ ID NO: 138) | VWEWDQPQ (SEQ ID NO: 139) |
| 1F1 | MHQMPWV (SEQ ID NO: 140) | YWRTTPFM (SEQ ID NO: 141) |
| 4E10 | TEWPEQY (SEQ ID NO: 52) | RHLFEYAE (SEQ ID NO: 57) |
| | RWDPFTH (SEQ ID NO: 53) | QNWFNQTS (SEQ ID NO: 58) |
| | DAHSFTA (SEQ ID NO: 54) | WNWFEQTN (SEQ ID NO: 59) |
| | DAPAVTV (SEQ ID NO: 55) | HNFFAQSA (SEQ ID NO: 60) |
| | DAPAVTV (SEQ ID NO: 55) | VLTHNFNN (SEQ ID NO: 61) |
| | SPLTFPA (SEQ ID NO: 56) | FNFFLQTA (SEQ ID NO: 62) |
| 2F5 | MWDKWSY (SEQ ID NO: 63) | WWIGEFPV (SEQ ID NO: 65) |
| | PYDKWAY (SEQ ID NO: 64) | RWYWVPHY (SEQ ID NO: 66) |
| Z13 | QPTFMPE (SEQ ID NO: 67) | MIPWMVPG (SEQ ID NO: 76) |
| | EWQVDAE (SEQ ID NO: 68) | DWWWDTIE (SEQ ID NO: 77) |
| | MEYSWQY (SEQ ID NO: 69) | PWNWVDLT (SEQ ID NO: 78) |
| | ERWAMWY (SEQ ID NO: 70) | HPWIKWYW (SEQ ID NO: 79) |
| | AHAWLPE (SEQ ID NO: 71) | WHPWFQYE (SEQ ID NO: 80) |
| | QEASWLS (SEQ ID NO: 72) | WVPEQFDQ (SEQ ID NO: 81) |
| | YDEWFWT (SEQ ID NO: 73) | DPWLMPPA (SEQ ID NO: 82) |
| | RRFWPPF (SEQ ID NO: 74) | TATKSFWW (SEQ ID NO: 83) |
| | SSTEWFV (SEQ ID NO: 75) | DIPKQWGK (SEQ ID NO: 84) |
| 447-52D | TVHAVPT (SEQ ID NO: 85) | LYPLDQSS (SEQ ID NO: 101) |
| | SANFPSV (SEQ ID NO: 86) | DLHFYVVS (SEQ ID NO: 102) |
| | ANAPVAT (SEQ ID NO: 87) | LYPMQASL (SEQ ID NO: 103) |
| | SKSTFHV (SEQ ID NO: 88) | TSYYKKFP (SEQ ID NO: 104) |
| | LAPLSVV (SEQ ID NO: 89) | LYPYPVAS (SEQ ID NO: 105) |
| | QFQYPVV (SEQ ID NO: 90) | STYPLLIF (SEQ ID NO: 106) |
| | APPLNVV (SEQ ID NO: 91) | LYPKPEPH (SEQ ID NO: 107) |
| | APSLPVV (SEQ ID NO: 92) | LYPFPTQD (SEQ ID NO: 108) |
| | FPSSLPV (SEQ ID NO: 93) | LYNPQYMY (SEQ ID NO: 109) |
| | STSPLPT (SEQ ID NO: 94) | LYPSHLSS (SEQ ID NO: 110) |
| | PPVMSPV (SEQ ID NO: 95) | LYPPAKVH (SEQ ID NO: 111) |
| | LPPPHPL (SEQ ID NO: 96) | LYPYPPIS (SEQ ID NO: 112) |
| | YVTLHPV (SEQ ID NO: 97) | LYPYPTHL (SEQ ID NO: 113) |
| | TLPMLPT (SEQ ID NO: 98) | LYPYPYEY (SEQ ID NO: 114) |
| | NWRWVMED (SEQ ID NO: 99) | SIHMGPRG (SEQ ID NO: 115) |
| | PATQHPV (SEQ ID NO: 100) | LYPLPPLL (SEQ ID NO: 116) |
| VRC01 | SPPTFPM (SEQ ID NO: 145) | SLLDFPIV (SEQ ID NO: 146) |
| | YVNAQVVF (SEQ ID NO: 147) | ATEELHVSQ (SEQ ID NO: 148) |
| | LPHAPMA (SEQ ID NO: 149) | PFYSFPHM (SEQ ID NO: 150) |
| | MPFVFTP (SEQ ID NO: 151) | SYVPFADV (SEQ ID NO: 152) |
| | LHHSPSA (SEQ ID NO: 153) | LTLLPNYV (SEQ ID NO: 154) |
| | HISFPYT (SEQ ID NO: 155) | SLFYPVPS (SEQ ID NO: 156) |
| | ATSLSTL (SEQ ID NO: 157) | FPNYSYPL (SEQ ID NO: 158) |
| | ASSLPSL (SEQ ID NO: 159) | FAPQLHTL (SEQ ID NO: 160) |

The clones generated against the b12 Mab are mimics of a conformational epitope and so did not demonstrate homology to Env. The b12 clones, when compared within their subset, showed a conserved consensus (VHFALPV (SEQ ID NO:13)) sequence within the BC loop but not within the FG loop, regardless of being derived from the NHK or Trimer libraries. The remaining clones generated against target antibodies (2F5, 4E10, 447-52D, Z13) are mimics of linear epitopes. In these cases, a number of clones were isolated that had significant predicted amino acid homology to the native epitopes recognized by the target Mab; these regions of homology were located within either the BC loop (2F5) or the FG loop (4E10, 447-52D, Z13).

Figure 13:
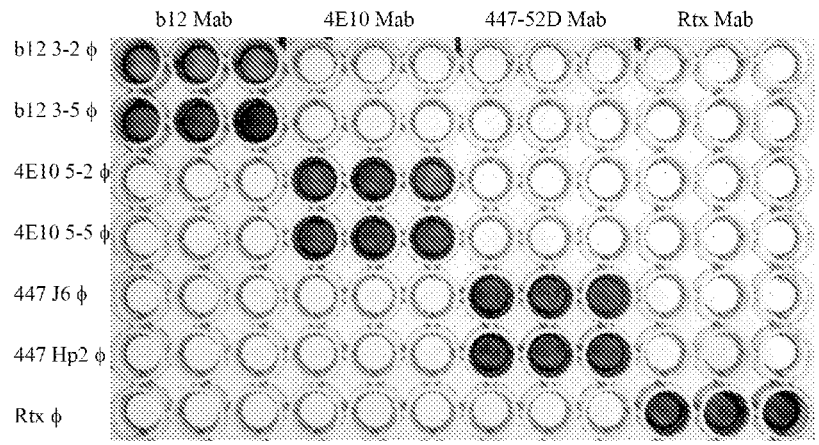

A subset of the selected phage were next tested for their reactivity with a panel of Mabs, including three Env-reactive Mabs (b12, 4E10, and 447-52D) and one irrelevant Mab (Rituxan, Rtx). Included in this analysis were three phage clones, each that had been selected using the Env-reactive Mabs, and one clone selected with rituxan. As shown in FIG. 13, each phage construct reacted only with its cognate Mab and had no reactivity with the Rtx antibody.

As noted above, b12 is a well-characterized Mab which recognizes the CD4 binding site of HIV-1 Env. Previous studies have defined the binding interface between the b12 Mab and Env and show that the b12 Mab residues Y53, Y98, and W100 are essential for binding to HIV-1 gp140. Zwick et al., "Identification and Characterization of a Peptide That Specifically Binds the Human, Broadly Neutralizing Anti-Human Immunodeficiency Virus Type 1 Antibody b12," *J. Virol.* 75(14):6692-6699 (2001), which is hereby incorporated by reference in its entirety. The reactivity of the b12-reactive phage clones with wild-type b12 Mab and with Y53G, Y98A, and W100A mutants of b12 was therefore examined Several of these clones are also shown in FIGS. 8, 9, and 10A-B. As a control for these experiments, the B2.1 phage clone was again used. This phage clone was selected from a conventional peptide display library (Saphire et al., "Structure of a High-Affinity "Mimotope" Peptide Bound to HIV-1-Neutralizing Antibody b12 Explains Its Inability to Elicit gp120 Cross-Reactive Antibodies," *J. Mol. Biol.* 369 (3):696-709 (2007), which is hereby incorporated by reference in its entirety) and binds to the b12 Mab in a manner distinct from HIV-1 gp140. Thus, B2.1 binds to Y53G, Y98A, and W100A mutants of the b12 Mab, even though none of these antibody mutants binds HIV-1 Env. Saphire et al., "Structure of a High-Affinity "Mimotope" Peptide Bound to HIV-1-Neutralizing Antibody b12 Explains Its Inability to Elicit gp120 Cross-Reactive Antibodies," *J. Mol. Biol.* 369 (3):696-709 (2007), which is hereby incorporated by reference in its entirety.

Figure 14:
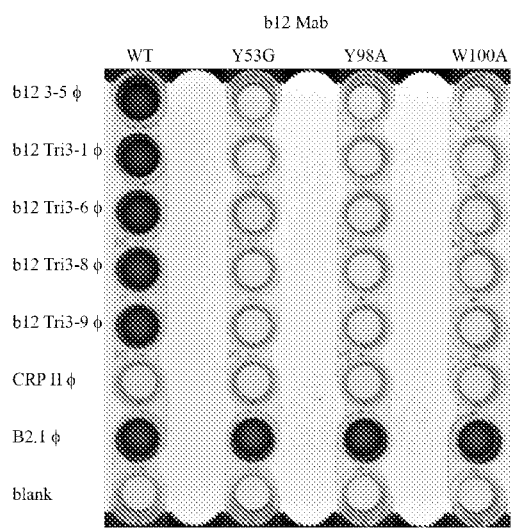

As shown in FIG. 14, 100% of the b12-specific phage clones reacted with wild-type b12 Mab, but failed to react with the Y53G, Y98A, W100A b12 mutants all of which also fail to bind to HIV-1 Env, but retain the ability to bind B2.1. An irrelevant phage clone, CRP II, which is not reactive to b12 Mab or its mutants was included as a negative control.

Soluble recombinant protein corresponding to a selected subset of the phage clones was next produced. FN encoding sequences were excised from phage clones of interest, subcloned into a prokaryotic expression vector, and proteins were expressed in *E. coli* BL21 host cells with terminal His, biotin, and FLAG tags. Proteins were then purified using metal affinity chromatography to bind the protein His tag. Samples of the purified b12 3-5 FN epitope surrogate were then analyzed by SDS-PAGE and visualized by Coomassie Blue staining. A single protein species of the expected molecular weight (15-17 kDa) was detected. Subsequently, the ability of this protein to bind the b12 Mab was tested. The b12 3-5 FN protein bound efficiently to immobilized b12 Mab as did the HIV-1 gp140, the positive control for the assay.

Next, the ability of HIV-1 gp140 to competitively inhibit binding of the b12 Mab to immobilized b12 FN 3-5 protein was examined. An HIV-1 gp140 mutant that is unable to bind to the b12 Mab was used as a control (D368R). The results show that wild-type gp140, but not the D368R mutant, competitively inhibit binding of the b12 Mab to the b12 3-5 protein epitope surrogate (FIG. 15).

To identify key residues involved in antibody binding by the b12 3-5 FN epitope surrogate, systematic alanine mutation of the BC and FG loop sequences was performed. The antibody binding efficiency of the mutants was measured by quantitative ELISA. Residues at which an alanine substitution reduced binding by >5× compared to the un-mutated protein were defined as key residues. FIG. 16 shows that the BC mutants H24A and F25A play a critical role in binding to the b12 Mab. It can also be seen that there is a small decrease in binding efficiency due to mutations in the FG loop at I78A, I83A, and L84A, but no single residue was found to be critical for binding. However, complete exchange of the FG loop for FG loop sequences from two irrelevant controls (1F1 and Rtx), demonstrated that some FG loop sequences were incompatible with b12 Mab binding. This is exemplified by the b12/Rtx FN mutant which almost completely failed to bind to the b12 Mab (see FIG. 16). Several alanine substitutions generated enhanced binding efficiency, including P28A in the BC loop as well as H77A and H28A in the FG loop. Combined alanine substitutions at these sites of b12 FN3-5 is therefore contemplated.

FN epitope surrogates of known linear antibody epitopes were also characterized. 2F5 and 4E10 epitope surrogates that showed partial homology with the native epitope were chosen for this analysis along with a clone (4E10 5-2 FN) that did not show homology to the 4E10 epitope. The ability of these FN epitope surrogates, as well as an irrelevant FN (1F1) to bind to the 2F5 and 4E10 Mabs was assayed using a competition ELISA. FIG. 17A shows that the 2F5 17 FN was able to competitively inhibit the binding of the 2F5 Mab to its cognate peptide epitope (CNEQELLELDKWASLWSGGRGGL (SEQ ID NO:142)). Similar results were also obtained with both 4E10 FNs (see FIG. 17B) including the FN with no amino acid homology to the 4E10 peptide epitope (CSLWN-WFDITNWLWRRK (SEQ ID NO:143)). FIG. 17 shows the results that epitope surrogates, 2F5 FN protein and 4E10 FN protein, competitively inhibit the binding of their corresponding antibodies to their target epitopes in the HIV-1 Env.

Example 8

Analysis of Patient Sera by Flow Cytometry for Identification of Reactive B Cells Peripheral blood was obtained from study subjects (HIV026 and HC1965) under a protocol approved by the Research Subjects Review Board at the University of Rochester Medical Center. HIV026 is an HIV-infected subject whose serum was previously determined to have substantial HIV broadly neutralizing activity using a TZM.b1 assay. Montefiori, D. C., "Evaluating Neutralizing Antibodies Against HIV, SIV, And SHIV In Luciferase Reporter Gene Assays," *Curr. Protoc. Immunol.* Chapter 12: Unit 12.11 (2005), which is hereby incorporated by reference in its entirety. Peripheral blood mononuclear cells ("PBMC") were isolated within 2 h after blood was drawn by Ficoll-Hypaque (Mediatech) density gradient centrifugation and then resuspended in Fetal Bovine Serum (FBS) with 10% DMSO and stored in liquid nitrogen.

Cells were thawed in a 37° C. waterbath, washed twice with RPMI-1640 culture medium containing 10% fetal bovine serum (FBS) (R10) and resuspended at 2-10 million cells/ml in the same medium (R10), containing 10 ng/ml IL-2 (Peprotech, Rocky Hill, N.J.). Cells were cultured overnight in 96 well round-bottom tissue culture plates at 37° C. and 5% CO2. Cells were harvested and treated with DNase I (20 ug/ml, Worthington Biochemical, Lakewood, N.H.) at 37° C. for 30 minutes and then washed twice in cold staining buffer (PBS pH 7.2 containing 0.5% BSA and 2 mM EDTA) and stained with anti-CD19-PE-Cy7 (BD Biosciences, San Diego, Calif.), anti-CD20-APC-Cy7 (BD), anti-IgD-PE (BD), anti-IgM-PerCP-Cy5.5 (BD), anti-CD27-Qdot605 (Invitrogen, Carlsbad, Calif.), anti-CD3-PE-Cy5 (BD), oligomeric YU2 gp140-AlexaFluor647 (UR), 1F1-FN-Pacific Blue (UR), and biotinylated 4E10 5-5 FN complexed with streptavidin-AlexaFluor488 (UR) for 60 min on ice. Antigen staining control samples were prepared by staining with all reagents, except YU2gp140, 1F1-FN, and 4E10 5-5 FN. Cells were washed twice with staining buffer, 7-AAD (Southern Biotech, Birmingham, Ala.) was added to discriminate dead cells, and samples analyzed using a FACSAria II (BD Biosciences). Approximately 1 million to 50 million total events were recorded to FCS files per sample. Further analysis of FCS files was performed using FlowJo software (TreeStar, Ashland, Oreg.).

To see if the FN epitope surrogates are able to be used for detection assays to determine if human sera contains HIV-1 specific Mabs, the specificity of an HIV-1 infected patient's peripheral blood mononuclear cells (PBMC) was tested against the 4E10 FN (FIG. 18). FIG. 18 shows the identification of 4E10-FN and HIV gp140 reactive B cells by flow cytometry. These results demonstrate that FN epitope surrogates are able to be used for detection assays to determine if sera contains Mabs.

This method of generating epitope surrogates not only creates mimics of the native antigen, but also creates FNs that structurally complement the antibody binding site by nature of the interactions between the discontinuous exposed BC and FG loops.

Example 9

Vaccine Strategy to Produce Broadly HIV Neutralizing Antibodies (Mab) Through Mobilization of Specified Progenitor Cells Using FNfn10 Proteins This immunization scheme (FIG. 19) seeks to solve a key problem: the unusually high degree of affinity maturation that characterizes most Mabs (Pancera et al., "Crystal Structure of PG16 and Chimeric Dissection With Somatically Related PG9: Structure-Function Analysis of Two Quaternary-Specific Antibodies That Effectively Neutralize HIV-1," *J. Virol.* 84(16):8098-110 (2010); Zhou et al., "Structural Basis for Broad and Potent Neutralization of HIV-1 by Antibody VRC01," *Science* 329(5993):811-7 (2010); Xiao et al., "Germline-Like Predecessors of Broadly Neutralizing Antibodies Lack Measurable Binding to HIV-1 Envelope Glycoproteins: Implications for Evasion of Immune Responses and Design of Vaccine Immunogens," *Biochem. Biophys. Res. Commun.* 390(3):404-9 (2009); Wu et al., "Rational Design of Envelope Identifies Broadly Neutralizing Human Monoclonal Antibodies to HIV-1," *Science* 329(5993):856-61 (2010); Kunert et al., "Molecular Characterization of Five Neutralizing Anti-HIV Type 1 Antibodies: Identification of Nonconventional D Segments in the Human Monoclonal Antibodies 2G12 and 2F5," *AIDS Res. Hum. Retroviruses* 14(13):1115-28 (1998), which are hereby incorporated by reference in their entireties), and the fact that the germline progenitors of many Mabs have either very low or undetectable affinity for HIV-1 Env Pancera et al., "Crystal Structure of PG16 and Chimeric Dissection With Somatically Related PG9: Structure-Function Analysis of Two Quaternary-Specific Antibodies That Effectively Neutralize HIV-1," *J. Virol.* 84(16):8098-110 (2010) and Xiao et al., "Germline-Like Predecessors of Broadly Neutralizing Antibodies Lack Measurable Binding to HIV-1 Envelope Glycoproteins: Implications for Evasion of Immune Responses and Design of Vaccine Immunogens," *Biochem. Biophys. Res. Commun.* 390(3):404-9 (2009), which are hereby incorporated by reference in their entireties. The lack of germline reactivity against Mab epitopes may explain why it has proven so difficult to elicit Mabs through immunization, and why broadly neutralizing antibodies are uncommon in HIV-1 infected subjects. Li et al., "Analysis of Neutralization Specificities in Polyclonal Sera Derived From Human Immunodeficiency Virus Type 1-Infected Individuals," *J. Virol.* 83(2):1045-59 (2009); Dhillon et al., "Dissecting the Neutralizing Antibody Specificities of Broadly Neutralizing Sera From Human Immunodeficiency Virus Type 1-Infected Donors," *J. Virol.* 81(12):6548-62 (2007); Doria-Rose et al., "Breadth of Human Immunodeficiency Virus-Specific Neutralizing Activity in Sera: Clustering Analysis and Association With Clinical Variables," *J. Virol.* 84(3):1631-6 (2010); Binley et al., "Profiling the Specificity of Neutralizing Antibodies in a Large Panel of Plasmas From Patients Chronically Infected With Human Immunodeficiency Virus Type 1 Subtypes B and C," *J. Virol.* 82(23):11651-68 (2008); Doria-Rose et al., "Frequency and Phenotype of Human Immunodeficiency Virus Envelope-Specific B Cells From Patients With Broadly Cross-Neutralizing Antibodies," *J. Virol.* 83(1):188-99 (2009); Sather et al., "Factors Associated With the Development of Cross-Reactive Neutralizing Antibodies During Human Immunodeficiency Virus Type 1 Infection," *J. Virol.* 83(2):757-69 (2009); and Simek et al., "Human Immunodeficiency Virus Type 1 Elite Neutralizers: Individuals With Broad and Potent Neutralizing Activity Identified by Using a High-Throughput Neutralization Assay Together With an Analytical Selection Algorithm," *J. Virol.* 83(14):7337-48 (2009), which are hereby incorporated by reference in their entireties.

The purpose of this immunization scheme is to use FNfn10-derived anti-idiotype reagents to selectively amplify specific B cell populations that represent the source of broadly-neutralizing antibodies (Mab) directed against HIV-1 (or other pathogens of interest). The strategy takes advantage of the fact that specific pairs of genomic VH and VK genes are predicted to represent the progenitors of somatically hypermutated, broadly neutralizing antibodies. It is proposed that anti-idiotypic (Id) FNfn10 proteins capable of binding efficiently to naïve or memory B cells that represent potential progenitors of Mab-producing cells can be used to elicit a broadly neutralizing antibody response to HIV-1. These anti-Ids may be used as vaccine immunogens either alone, or in combination with antigenic mimics, or with more conventional Env immunogens. The humoral response in this immunization scheme may be further enhanced using appropriate immunologic adjuvants such as a suitable Toll-like receptor ligand (e.g., TLR9). It may also be enhanced by displaying FNfn10-derived anti-Ids or antigenic mimics in an oligomeric or multimeric manner that enhances their immunogenicity and/or their ability to trigger the activation and proliferation of target B cells (e.g., by displaying them on a virus-like particle or equivalent scaffold, by tetramerizing them using avidin-biotin chemistry, or through other methods known to those skilled in the art).

Poor germline reactivity against HIV-1 Mab epitopes is thought to represent a major block to the elicitation of Mab responses following immunization. A potential solution to this problem is to use "intermediate" antigenic structures to mobilize these germline specificities and/or to target the germline specificities directly, thereby initiating their affinity maturation. Subsequent immunization with HIV-1 Env (or subdomains thereof), or with antigen mimics, would then be expected to select for clones that can now bind to Mab epitopes. The FNfn10 display described in the preceding Examples can be used to select for FNfn10 clones that efficiently bind to the germline progenitors of these same antibodies. Pancera et al., "Crystal Structure of PG16 and Chimeric Dissection With Somatically Related PG9: Structure-Function Analysis of Two Quaternary-Specific Antibodies That Effectively Neutralize HIV-1," *J. Virol.* 84(16):8098-110 (2010); Zhou et al., "Structural Basis for Broad and Potent Neutralization of HIV-1 by Antibody VRC01," *Science* 329(5993):811-7 (2010); Xiao et al., "Germline-Like Predecessors of Broadly Neutralizing Antibodies Lack Measurable Binding to HIV-1 Envelope Glycoproteins: Implications for Evasion of Immune Responses and Design of Vaccine Immunogens," *Biochem. Biophys. Res. Commun.* 390 (3):404-9 (2009); and Kunert et al., "Molecular Characterization of Five Neutralizing Anti-HIV Type 1 Antibodies: Identification of Nonconventional D Segments in the Human Monoclonal Antibodies 2G12 and 2F5," *AIDS Res. Hum. Retroviruses* 14(13):1115-28 (1998), which are hereby incorporated by reference in their entireties.

As shown in FIG. 20, FNfn10 anti-idiotypes (anti-Ids) can be readily generated against genomic/germline progenitors of HIV-1 Mabs. FIG. 20 shows a FNfn10 anti-Id that was selected against the predicted VRC01 germline antibody. The VRC01 Mab is a human monoclonal antibody directed against the CD4 binding site (CD4bs) of HIV-1 Env, which neutralizes more than 90% of circulating virus isolates (Wu et al., "Rational Design of Envelope Identifies Broadly Neutralizing Human Monoclonal Antibodies to HIV-1," *Science* 329 (5993):856-61 (2010), which is hereby incorporated by reference in its entirety). The antibody contacts Env mainly through immunoglobulin (Ig) V-gene regions that have undergone substantial affinity maturation, relative to their genomic precursors (Zhou et al., "Structural Basis for Broad and Potent Neutralization of HIV-1 by Antibody VRC01," *Science* 329(5993):811-7 (2010), which is hereby incorporated by reference in its entirety). Thus, the VH gene region has 41 residue alterations from germline and the VK gene region has 25 such changes. When these VH and VK regions of VRC01 were replaced with the sequences of their closest genomic precursors, and expressed as intact Igs, it was found that the germline revertants failed to bind detectably to HIV-1 Env or to neutralize virus infectivity. Moreover, antibody binding affinity and neutralization activity were found to be significantly correlated with the number of affinity matured residues compared to the germline precursor. The VRC01 antibody and its germline revertant were expressed using published sequences (Wu et al., "Rational Design of Envelope Identifies Broadly Neutralizing Human Monoclonal Antibodies to HIV-1," *Science* 329(5993):856-61 (2010); Zhou et al., "Structural Basis for Broad and Potent Neutralization of HIV-1 by Antibody VRC01" *Science* 329(5993):811-7 (2010), which are hereby incorporated by reference in their entirety), and then used to select for FN anti-idiotypes directed against both the mature VRC01 antibody and its "germline revertant". Shown in FIG. 20 is an example of an anti-Id FN directed against the VRC01 "germline" antibody. In this example, an anti-Id FN was selected against the VRC01 "germline" antibody, and then phage particles displaying this FN were probed in quadruplicate wells for reactivity against mature VRC01 antibody (VRC01) versus its "germline revertant" (VRC01GL). As this Figure shows, this anti-Id FN reacts with the VRC01 "germline" antibody (VRC01GL) but not the mature antibody (VRC01). Since the FN is tagged with the Flag epitope, reactivity with an anti-Flag antibody was included as a control. The sequences of the engineered loops for this FN construct were: LQSALFA (BC) (SEQ ID NO:161) and PYFPAEFP (FG) (SEQ ID NO:162).

Example 10

Vaccine Strategy to Produce a Pan-Influenza Vaccine Through Mobilization of $V_H$1-69 Positive B Cells Using FNfn10 Proteins Monoclonal antibodies with broadly-neutralizing (BN) activity against influenza viruses have recently been identified, and shown to react against a conserved conformational epitope (the so-called "fusion pocket") located in the stalk of the hemagglutinin (HA) ectodomain, thereby preventing membrane fusion. Broadly neutralizing antibodies directed against the HA stalk domain are protective against divergent H5N1 and H1N1 viruses, suggesting that a pandemic influenza vaccine may be feasible.

Human BN monoclonal antibodies (Mabs) that recognize the HA stalk domain have a strikingly restricted immunoglobulin (Ig) V-chain usage pattern, and are characterized in most cases by the use of the VH1-69 gene (Ekiert et al., "Antibody Recognition of a Highly Conserved Influenza Virus Epitope," *Science* 324(5924):246-51 (2009); Sui et al., "Structural and Functional Bases for Broad-Spectrum Neutralization of Avian and Human Influenza A Viruses," *Nat Struct Mol Biol.* 16(3):265-73 (2009); Wrammert et al., "Broadly Cross-reactive Antibodies Dominate the Human B Cell Response Against 2009 Pandemic H1N1 Influenza Virus Infection," *J Exp Med.* 208(1):181-93 (2011), which are hereby incorporated by reference in their entirety). Crystal structures of two of these stalk domain-reactive human Mabs (CR6261 and F10) show that they use only the heavy chain for interaction, and that most of antigen contact residues derive from the unmutated germline sequences (vide infra). Thus, these VH1-69 antibodies are unusual in that they appear to represent a potentially effective germline response with little requirement or affinity maturation (Kwong et al., "HIV-1 and Influenza Antibodies: Seeing Antigens in New Ways," *Nat Immunol.* 10(6):573-8 (2009), which is hereby incorporated by reference in its entirety). This may reflect, in part, the fact that VH1-69 is unique among all human heavy chain genes in possessing a hydrophobic, second complementarity-determining region (CDR2), which is capable of accessing the fusion pocket epitope.

It is therefore proposed that an effective pan-influenza vaccine can be produced by using an immunization strategy that efficiently mobilizes B cells expressing the VH1-69 genomic immunoglobulin gene heavy chain V-region allele. This scheme is illustrated in FIG. 21. The strategy will produce anti-idiotypes (Ids) that bind efficiently to the VH1-69 Ig heavy chain, and then these will be used to mobilize VH1-69 positive B cells; a subsequent immunologic boost with a conventional or modified influenza HA protein, or with one or more suitable antigenic mimics, will then be used to select for VH1-69 positive cells capable of binding efficiently to the fusion pocket epitope and neutralizing a broad range of influenza virus strains, including potential pandemic viruses.

The humoral response in this immunization scheme may be further enhanced using appropriate immunologic adjuvants such as a suitable Toll-like receptor ligand (e.g., TLR9). It may also be enhanced by displaying FNfn10-derived anti-Ids or antigenic mimics in an oligomeric or multimeric manner that enhances their immunogenicity and/or their ability to trigger the activation and proliferation of target B cells (e.g., by displaying them on a virus-like particle or equivalent scaffold, by tetramerizing them using avidin-biotin chemistry, or through other methods known to those skilled in the art).

This approach is preferable to using antibody-based anti-Ids because (i) conventional antibodies have the potential to trigger depletion of their target cells, through Fc-dependent mechanisms such as antibody-dependent cell-mediated cytotoxicity (ADCC) (Clark et al., "How Does B Cell Depletion Therapy Work, and How Can it be Improved?," *Ann Rheum Dis.* 64 Suppl 4:iv77-80 (2005), which is hereby incorporated by reference in its entirety) and (ii) the in vivo half-like of FNfn10 proteins is only about 24 hours, permitting one to use them to briefly perturb B cell populations, unlike conventional antibodies.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A modified polypeptide comprising:
   β-strand domain sequences A, B, C, D, E, F, and G of a wild-type mammalian Fn3 domain of fibronectin with loop region sequences AB, BC, CD, DE, EF, and FG linked between adjacent β-strand domain sequences; and
   optionally, an N-terminal tail of at least 2 amino acids, a C-terminal tail of at least 2 amino acids, or both;
   wherein at least one loop region sequence is selected from the BC and/or FG loop regions and comprises a modified amino acid sequence which varies from the wild-type sequence by deletion, insertion, or replacement of at least two amino acids from a different loop region in the wild-type mammalian Fn3 domain of fibronectin, resulting in a recombinant, modified Fn3 domain, wherein the modified amino acid sequence of the at least one recombinant, modified BC and/or FG loop region sequence comprises SEQ ID NO:11, SEQ ID NO:12, SEQ ID NO:13, SEQ ID NO:14, SEQ ID NO:15, SEQ ID NO:16, SEQ ID NO:22, SEQ ID NO:23, SEQ ID NO:24, SEQ ID NO:25, SEQ ID NO:26, SEQ ID NO:27, SEQ ID NO:28, SEQ ID NO:29, SEQ ID NO:30, SEQ ID NO:31, SEQ ID NO:32, SEQ ID NO:33, SEQ ID NO:34, SEQ ID NO:145, SEQ ID NO:146, SEQ ID NO:147, SEQ ID NO:148, SEQ ID NO:149, SEQ ID NO:150, SEQ ID NO:151, SEQ ID NO:152, SEQ ID NO:153, SEQ ID NO:154, SEQ ID NO:155, SEQ ID NO:156, SEQ ID NO:157, SEQ ID NO:158, SEQ ID NO:159, SEQ ID NO:160, SEQ ID NO:161, SEQ ID NO:162, SEQ ID NO:163, SEQ ID NO:164, SEQ ID NO:165, SEQ ID NO:166, SEQ ID NO:167, SEQ ID NO:168, SEQ ID NO:117, SEQ ID NO:118, SEQ ID NO:119, SEQ ID NO:120, SEQ ID NO:121, SEQ ID NO:122, SEQ ID NO:123, SEQ ID NO:124, SEQ ID NO:125, SEQ ID NO:126, SEQ ID NO:127, SEQ ID NO:128, or SEQ ID NO:129.

2. The modified polypeptide according to claim 1, wherein the modified polypeptide binds specifically to a neutralizing monoclonal antibody (Mab) selected from the group consisting of: HIV Mab b12, HIV F105 Mab, HIV PG9 Mab, HIV PG16 Mab, HIV 2G12 Mab, HIV 2F5 Mab, HIV 4E10 Mab, HIV VRC01 Mab, Dengue 1 F1 Mab, Influenza CR6261 Mab, Influenza F10 Mab, Influenza D8 Mab, and combinations thereof.

3. The modified polypeptide according to claim 1, wherein the modified polypeptide is capable of inducing an immune response against a viral pathogen, wherein the viral pathogen is selected from the group consisting of HIV, dengue virus, and/or influenza virus.

4. The modified polypeptide according to claim 1, wherein said at least one recombinant, modified loop region sequence is a BC loop region sequence, wherein the modified amino acid sequence comprises SEQ ID NO:11, SEQ ID NO:13, SEQ ID NO:15, SEQ ID NO:22, SEQ ID NO:25, SEQ ID NO:27, SEQ ID NO:29, SEQ ID NO:31, SEQ ID NO:33, SEQ ID NO:145, SEQ ID NO:147, SEQ ID NO:149, SEQ ID NO:151, SEQ ID NO:153, SEQ ID NO:155, SEQ ID NO:157, SEQ ID NO:159, SEQ ID NO:161, SEQ ID NO:163, SEQ ID NO:165, SEQ ID NO:166, SEQ ID NO:117, SEQ ID NO:119, SEQ ID NO:122, SEQ ID NO:124, SEQ ID NO:126, or SEQ ID NO:128.

5. The modified polypeptide according to claim 1, wherein said at least one recombinant, modified loop region sequence is a FG loop region sequence, wherein the modified amino acid sequence comprises SEQ ID NO:12, SEQ ID NO:14, SEQ ID NO:16, SEQ ID NO:23, SEQ ID NO:24, SEQ ID NO:26, SEQ ID NO:28, SEQ ID NO:30, SEQ ID NO:32, SEQ ID NO:34, SEQ ID NO:146, SEQ ID NO:148, SEQ ID NO:150, SEQ ID NO:152, SEQ ID NO:154, SEQ ID NO:156, SEQ ID NO:158, SEQ ID NO:160, SEQ ID NO:162, SEQ ID NO:164, SEQ ID NO:167, SEQ ID NO:168, SEQ ID NO:118, SEQ ID NO:120, SEQ ID NO:121, SEQ ID NO:123, SEQ ID NO:125, SEQ ID NO:127, or SEQ ID NO:129.

6. The modified polypeptide according to claim 1, wherein the at least one recombinant, modified loop region sequence is a combination of the BC loop region sequence and the FG loop region sequence, wherein the modified BC and FG loop region sequences comprise, respectively, SEQ ID NO:11 and SEQ ID NO:12; SEQ ID NO:13 and SEQ ID NO:14; SEQ ID NO:15 and SEQ ID NO:16; SEQ ID NO:22 and SEQ ID NO:23; SEQ ID NO:13 and SEQ ID NO:24; SEQ ID NO:25 and SEQ ID NO:26; SEQ ID NO:27 and SEQ ID NO:28; SEQ ID NO:29 and SEQ ID NO:30; SEQ ID NO:31 and SEQ ID NO:32; SEQ ID NO:33 and SEQ ID NO:34; SEQ ID NO:145 and SEQ ID NO:146; SEQ ID NO:147 and SEQ ID NO:148; SEQ ID NO:149 and SEQ ID NO:150; SEQ ID NO:151 and SEQ ID NO:152; SEQ ID NO:153 and SEQ ID NO:154; SEQ ID NO:155 and SEQ ID NO:156; SEQ ID NO:157 and SEQ ID NO:158; SEQ ID NO:159 and SEQ ID NO:160; SEQ ID NO:161 and SEQ ID NO:162; SEQ ID NO:163 and SEQ ID NO:164; SEQ ID NO:165 and SEQ ID NO:167; SEQ ID NO:166 and SEQ ID NO:168; SEQ ID NO:117 and SEQ ID NO:118; SEQ ID NO:119 and SEQ ID NO:120; SEQ ID NO:117 and SEQ ID NO:121; SEQ ID NO:122 and SEQ ID NO:123; SEQ ID NO:124 and SEQ ID NO:125; SEQ ID NO:126 and SEQ ID NO:127; or SEQ ID NO:128 and SEQ ID NO:129.

7. The modified polypeptide according to claim 1, wherein the wild-type Fn3 domain of fibronectin is a wild-type tenth Fn3 domain of fibronectin.

8. An isolated nucleic acid molecule encoding the modified polypeptide of claim 1.

9. The isolated nucleic acid molecule according to claim 8, wherein the isolated nucleic acid is DNA.

10. A DNA construct comprising the DNA molecule of claim 9, further comprising a promoter operably coupled to the 5' of the DNA molecule and a transcription termination DNA molecule operably coupled to the 3' of the DNA molecule.

11. An expression vector comprising the DNA construct of claim 10.

12. An isolated host cell transformed with a DNA construct according to claim 10.

13. A composition comprising a pharmaceutically acceptable carrier and the modified polypeptide according to claim 1.

14. An immunogenic composition comprising a pharmaceutically acceptable carrier and either the modified polypeptide according to claim 1, a DNA molecule encoding the modified polypeptide, or a combination thereof.

15. A method of administering an immunogenic composition according to claim 14 to a mammal under conditions effective to induce an immune response against the modified polypeptide.

16. An isolated antibody or binding fragment thereof specific for the modified polypeptide according to claim 1.

17. A method for detecting a neutralizing antibody in serum comprising:
providing the modified polypeptide of claim 1 conjugated to a label;
contacting the labeled, modified polypeptide with serum from an individual; and
detecting whether the labeled, modified polypeptide binds to an antibody present in the serum, wherein said detecting is carried out using the label.

* * * * *

SEQUENCE LISTING

```
<160> NUMBER OF SEQ ID NOS: 169

<210> SEQ ID NO 1
<211> LENGTH: 99
<212> TYPE: PRT
<213> ORGANISM: Human

<400> SEQUENCE: 1

Val Ser Asp Val Pro Arg Asp Leu Glu Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr Gly Lys
                85                  90                  95

Lys Gly Lys

<210> SEQ ID NO 2
<211> LENGTH: 94
<212> TYPE: PRT
<213> ORGANISM: Human

<400> SEQUENCE: 2

Val Ser Asp Val Pro Arg Asp Leu Glu Val Ala Ala Thr Pro Thr
 1               5                  10                  15

Ser Leu Leu Ile Ser Trp Asp Ala Pro Ala Val Thr Val Arg Tyr Tyr
                20                  25                  30

Arg Ile Thr Tyr Gly Glu Thr Gly Gly Asn Ser Pro Val Gln Glu Phe
            35                  40                  45

Thr Val Pro Gly Ser Lys Ser Thr Ala Thr Ile Ser Gly Leu Lys Pro
        50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 3
<211> LENGTH: 94
<212> TYPE: PRT
<213> ORGANISM: Macaca mulatta

<400> SEQUENCE: 3

Val Ser Asp Val Pro Arg Asp Leu Glu Val Ala Ala Thr Pro Thr
 1               5                  10                  15
```

Ser Leu Leu Ile Ser Trp Asp Ala Pro Ala Val Thr Val Arg Tyr Tyr
             20                  25                  30

Arg Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 4
<211> LENGTH: 94
<212> TYPE: PRT
<213> ORGANISM: Pan troglodytes

<400> SEQUENCE: 4

Val Ser Asp Val Pro Arg Asp Leu Glu Val Val Ala Ala Thr Pro Thr
1               5                   10                  15

Ser Leu Leu Ile Ser Trp Asp Ala Pro Ala Val Thr Val Arg Tyr Tyr
             20                  25                  30

Arg Ile Thr Tyr Gly Glu Thr Gly Gly Asn Ser Pro Val Gln Glu Phe
             35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 5
<211> LENGTH: 94
<212> TYPE: PRT
<213> ORGANISM: Bos taurus

<400> SEQUENCE: 5

Val Ser Asp Val Pro Arg Asp Leu Glu Val Ile Ala Ala Thr Pro Thr
1               5                   10                  15

Ser Leu Leu Ile Ser Trp Asp Ala Pro Ala Val Thr Val Arg Tyr Tyr
             20                  25                  30

Arg Ile Thr Tyr Gly Glu Thr Gly Gly Ser Ser Pro Val Gln Glu Phe
             35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Val Ser Ile Asn Tyr Arg Thr
                85                  90

<210> SEQ ID NO 6
<211> LENGTH: 94
<212> TYPE: PRT
<213> ORGANISM: Canis familiaris

<400> SEQUENCE: 6

Val Ser Asp Val Pro Arg Asp Leu Glu Val Ile Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Ala Asp Tyr Thr Ile Thr Val Tyr Ala Val Thr Gly Arg Gly Asp
65                  70                  75                  80

Ser Pro Ala Ser Ser Lys Pro Val Ser Ile Asp Tyr Arg Thr
                85                  90

<210> SEQ ID NO 7
<211> LENGTH: 94
<212> TYPE: PRT
<213> ORGANISM: Equus caballus

<400> SEQUENCE: 7

Val Ser Asp Val Pro Arg Asp Leu Glu Val Ile Ala Thr Thr Pro Thr
1               5                   10                  15

Ser Ile Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asp Tyr Arg Thr
                85                  90

<210> SEQ ID NO 8
<211> LENGTH: 94
<212> TYPE: PRT
<213> ORGANISM: Mus musculus

<400> SEQUENCE: 8

Val Ser Asp Ile Pro Arg Asp Leu Glu Val Ile Ala Ser Thr Pro Thr
1               5                   10                  15

Ser Leu Leu Ile Ser Trp Glu Pro Pro Ala Val Ser Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Asn Asn Ile Lys Pro
    50                  55                  60

Gly Ala Asp Tyr Thr Ile Thr Leu Tyr Ala Val Thr Gly Arg Gly Asp
65                  70                  75                  80

Ser Pro Ala Ser Ser Lys Pro Val Ser Ile Asn Tyr Lys Thr
                85                  90

<210> SEQ ID NO 9
<211> LENGTH: 94
<212> TYPE: PRT
<213> ORGANISM: Rattus norvegicus

<400> SEQUENCE: 9

Val Ser Asp Val Pro Arg Asp Leu Glu Val Ile Ala Ser Thr Pro Thr
1               5                   10                  15

Ser Leu Leu Ile Ser Trp Glu Pro Pro Ala Val Ser Val Arg Tyr Tyr

```
                    20                  25                  30
Arg Ile Thr Tyr Gly Glu Thr Gly Gly Asn Ser Pro Val Gln Glu Phe
                35                  40                  45
Thr Val Pro Gly Ser Lys Ser Thr Ala Thr Ile Asn Asn Ile Lys Pro
             50                  55                  60
Gly Ala Asp Tyr Thr Ile Thr Leu Tyr Ala Val Thr Gly Arg Gly Asp
 65                  70                  75                  80
Ser Pro Ala Ser Ser Lys Pro Val Ser Ile Asn Tyr Gln Thr
                 85                  90

<210> SEQ ID NO 10
<211> LENGTH: 94
<212> TYPE: PRT
<213> ORGANISM: Ornithorhynchus anatinus

<400> SEQUENCE: 10

Val Ser Asp Val Pro Arg Asp Leu Glu Ile Ile Ala Thr Thr Pro Thr
 1               5                  10                  15
Ser Leu Leu Ile Asn Trp Glu Ala Pro Ala Val Thr Val Arg Tyr Tyr
                20                  25                  30
Arg Ile Thr Tyr Gly Glu Thr Gly Gly Thr Ser Pro Val Gln Glu Phe
                35                  40                  45
Thr Val Pro Gly Thr Lys Ser Ser Ala Thr Ile Ser Gly Leu Lys Pro
             50                  55                  60
Gly Ala Asp Tyr Ile Ile Thr Val Tyr Ala Val Thr Gly Arg Gly Asp
 65                  70                  75                  80
Ser Pro Ala Ser Ser Lys Pro Val Ser Ile Thr Tyr Arg Thr
                 85                  90

<210> SEQ ID NO 11
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 11

Val His Phe Ala Leu Pro Ala
 1               5

<210> SEQ ID NO 12
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 12

Tyr Leu Ser Asp Val Pro Asp Leu
 1               5

<210> SEQ ID NO 13
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 13

Val His Phe Ala Leu Pro Val
 1               5
```

```
<210> SEQ ID NO 14
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 14

His Ile Ser His Gln His Ile Leu
1               5

<210> SEQ ID NO 15
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 15

Val His Phe Ala Tyr Pro Thr
1               5

<210> SEQ ID NO 16
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 16

Asp Phe Pro Ser Ala Pro Pro Pro
1               5

<210> SEQ ID NO 17
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 17

Ser Pro Pro His Pro Phe Thr
1               5

<210> SEQ ID NO 18
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 18

Phe His Ala Phe Ser His Tyr Gln
1               5

<210> SEQ ID NO 19
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 19

Val Pro Ala His Pro Phe Ile
1               5
```

```
<210> SEQ ID NO 20
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 20

Tyr His Pro Val Pro His Pro His
1               5

<210> SEQ ID NO 21
<211> LENGTH: 15
<212> TYPE: PRT
<213> ORGANISM: Artificial
<220> FEATURE:
<223> OTHER INFORMATION: Polypeptide Scaffold Loop Region

<400> SEQUENCE: 21

His Glu Arg Ser Tyr Met Phe Ser Asp Leu Glu Asn Arg Cys Ile
1               5                   10                  15

<210> SEQ ID NO 22
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 22

Val Pro Phe Ala Phe Pro Thr
1               5

<210> SEQ ID NO 23
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 23

Thr Asn His Tyr Met Val Ile
1               5

<210> SEQ ID NO 24
<211> LENGTH: 6
<212> TYPE: PRT
<213> ORGANISM: Artificial
<220> FEATURE:
<223> OTHER INFORMATION: Polypeptide Scaffold Loop Region

<400> SEQUENCE: 24

Thr Asn His Tyr Met Val
1               5

<210> SEQ ID NO 25
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 25

Val His Phe Ala Trp Thr Val
1               5

<210> SEQ ID NO 26
```

```
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 26

Asn Trp Gly Asp Thr His Gln His
1               5

<210> SEQ ID NO 27
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 27

Val His Trp Ala Leu Pro Val
1               5

<210> SEQ ID NO 28
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 28

Trp Trp Ser Gly Gln Trp Met Pro
1               5

<210> SEQ ID NO 29
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 29

Val His Phe Ala Tyr Pro Ala
1               5

<210> SEQ ID NO 30
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 30

Asp Ile Thr Met Gly Tyr Met Tyr
1               5

<210> SEQ ID NO 31
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 31

Met Asp His Thr Trp Leu Pro
1               5

<210> SEQ ID NO 32
<211> LENGTH: 8
```

```
<212> TYPE: PRT
<213> ORGANISM: Artificial
<220> FEATURE:
<223> OTHER INFORMATION: Polypeptide Scaffold Loop Region

<400> SEQUENCE: 32

Gln Trp Asp Gln Asn Val Trp Pro
1               5

<210> SEQ ID NO 33
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 33

Trp Asp Trp His Thr Tyr Cys
1               5

<210> SEQ ID NO 34
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 34

Cys Val Trp Trp Asp Tyr Gln Glu
1               5

<210> SEQ ID NO 35
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 35

Glu Asn Ala Ala Tyr Val Cys
1               5

<210> SEQ ID NO 36
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 36

Cys Arg Leu Lys His Tyr Phe Asn
1               5

<210> SEQ ID NO 37
<211> LENGTH: 6
<212> TYPE: PRT
<213> ORGANISM: Artificial
<220> FEATURE:
<223> OTHER INFORMATION: Influenza VH1-69 Mab CDR1

<400> SEQUENCE: 37

Gly Thr Phe Ser Ser Tyr
1               5

<210> SEQ ID NO 38
<211> LENGTH: 7
<212> TYPE: PRT
```

<213> ORGANISM: Artificial
<220> FEATURE:
<223> OTHER INFORMATION: Influenza VH1-69 Mab CDR2

<400> SEQUENCE: 38

Ile Ile Pro Ile Phe Gly Thr
1               5

<210> SEQ ID NO 39
<211> LENGTH: 6
<212> TYPE: PRT
<213> ORGANISM: Artificial
<220> FEATURE:
<223> OTHER INFORMATION: Influenza F10 Mab CDR1

<400> SEQUENCE: 39

Val Thr Phe Ser Ser Phe
1               5

<210> SEQ ID NO 40
<211> LENGTH: 7
<212> TYPE: PRT
<213> ORGANISM: Artificial
<220> FEATURE:
<223> OTHER INFORMATION: Influenza F10 Mab CDR2

<400> SEQUENCE: 40

Ile Ser Pro Met Phe Gly Thr
1               5

<210> SEQ ID NO 41
<211> LENGTH: 6
<212> TYPE: PRT
<213> ORGANISM: Artificial
<220> FEATURE:
<223> OTHER INFORMATION: Influenza D8 Mab CDR1

<400> SEQUENCE: 41

Gly Thr Phe Ser Ala Tyr
1               5

<210> SEQ ID NO 42
<211> LENGTH: 7
<212> TYPE: PRT
<213> ORGANISM: Artificial
<220> FEATURE:
<223> OTHER INFORMATION: Influenza D8 Mab CDR2

<400> SEQUENCE: 42

Ile Ile Gly Met Phe Gly Thr
1               5

<210> SEQ ID NO 43
<211> LENGTH: 6
<212> TYPE: PRT
<213> ORGANISM: Artificial
<220> FEATURE:
<223> OTHER INFORMATION: Influenza A66 Mab CDR1

<400> SEQUENCE: 43

Gly Pro Phe Ser Met Thr
1               5

<210> SEQ ID NO 44
<211> LENGTH: 7
<212> TYPE: PRT
<213> ORGANISM: Artificial

<220> FEATURE:
<223> OTHER INFORMATION: Influenza A66 Mab CDR2

<400> SEQUENCE: 44

Ile Ser Pro Ile Phe Arg Thr
1               5

<210> SEQ ID NO 45
<211> LENGTH: 6
<212> TYPE: PRT
<213> ORGANISM: Artificial
<220> FEATURE:
<223> OTHER INFORMATION: Influenza G17 Mab CDR1

<400> SEQUENCE: 45

Val Thr Phe Ser Ser Tyr
1               5

<210> SEQ ID NO 46
<211> LENGTH: 7
<212> TYPE: PRT
<213> ORGANISM: Artificial
<220> FEATURE:
<223> OTHER INFORMATION: Influenza G17 Mab CDR2

<400> SEQUENCE: 46

Ile Ile Gly Val Phe Gly Val
1               5

<210> SEQ ID NO 47
<211> LENGTH: 6
<212> TYPE: PRT
<213> ORGANISM: Artificial
<220> FEATURE:
<223> OTHER INFORMATION: Influenza D7 Mab CDR1

<400> SEQUENCE: 47

Gly Ile Phe Asn Thr Asn
1               5

<210> SEQ ID NO 48
<211> LENGTH: 7
<212> TYPE: PRT
<213> ORGANISM: Artificial
<220> FEATURE:
<223> OTHER INFORMATION: Influenza D7 Mab CDR2

<400> SEQUENCE: 48

Val Ile Pro Leu Phe Arg Thr
1               5

<210> SEQ ID NO 49
<211> LENGTH: 6
<212> TYPE: PRT
<213> ORGANISM: Artificial
<220> FEATURE:
<223> OTHER INFORMATION: Influenza CR6261 Mab CDR1

<400> SEQUENCE: 49

Gly Pro Phe Arg Ser Tyr
1               5

<210> SEQ ID NO 50
<211> LENGTH: 7
<212> TYPE: PRT
<213> ORGANISM: Artificial
<220> FEATURE:

<223> OTHER INFORMATION: Influenza CR6261 Mab CDR2

<400> SEQUENCE: 50

Ile Ile Pro Ile Phe Gly Thr
1               5

<210> SEQ ID NO 51
<211> LENGTH: 94
<212> TYPE: PRT
<213> ORGANISM: Artificial
<220> FEATURE:
<223> OTHER INFORMATION: Mutant Fn3 Scaffold
<220> FEATURE:
<221> NAME/KEY: MISC_FEATURE
<222> LOCATION: (7)..(7)
<223> OTHER INFORMATION: Xaa can be Asn or Lys

<400> SEQUENCE: 51

Val Ser Asp Val Pro Arg Xaa Leu Glu Val Val Ala Ala Thr Pro Thr
1               5                   10                  15

Ser Leu Leu Ile Ser Trp Asp Ala Pro Ala Val Thr Val Arg Tyr Tyr
            20                  25                  30

Arg Ile Thr Tyr Gly Glu Thr Gly Gly Asn Ser Pro Val Gln Glu Phe
        35                  40                  45

Thr Val Pro Gly Ser Lys Ser Thr Ala Thr Ile Ser Gly Leu Lys Pro
    50                  55                  60

Gly Val Asp Tyr Thr Ile Thr Val Tyr Ala Val Thr Gly Arg Gly Asp
65                  70                  75                  80

Ser Pro Ala Ser Ser Lys Pro Ile Ser Ile Asn Tyr Arg Thr
                85                  90

<210> SEQ ID NO 52
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 52

Thr Glu Trp Pro Glu Gln Tyr
1               5

<210> SEQ ID NO 53
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 53

Arg Trp Asp Pro Phe Thr His
1               5

<210> SEQ ID NO 54
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 54

Asp Ala His Ser Phe Thr Ala
1               5

```
<210> SEQ ID NO 55
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 55

Asp Ala Pro Ala Val Thr Val
1               5

<210> SEQ ID NO 56
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 56

Ser Pro Leu Thr Phe Pro Ala
1               5

<210> SEQ ID NO 57
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 57

Arg His Leu Phe Glu Tyr Ala Glu
1               5

<210> SEQ ID NO 58
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 58

Gln Asn Trp Phe Asn Gln Thr Ser
1               5

<210> SEQ ID NO 59
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 59

Trp Asn Trp Phe Glu Gln Thr Asn
1               5

<210> SEQ ID NO 60
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 60

His Asn Phe Phe Ala Gln Ser Ala
1               5

<210> SEQ ID NO 61
```

```
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 61

Val Leu Thr His Asn Phe Asn Asn
1               5

<210> SEQ ID NO 62
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 62

Phe Asn Phe Phe Leu Gln Thr Ala
1               5

<210> SEQ ID NO 63
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 63

Met Trp Asp Lys Trp Ser Tyr
1               5

<210> SEQ ID NO 64
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 64

Pro Tyr Asp Lys Trp Ala Tyr
1               5

<210> SEQ ID NO 65
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 65

Trp Trp Ile Gly Glu Phe Pro Val
1               5

<210> SEQ ID NO 66
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 66

Arg Trp Tyr Trp Val Pro His Tyr
1               5

<210> SEQ ID NO 67
<211> LENGTH: 7
```

```
<212> TYPE: PRT
<213> ORGANISM: Artificial
<220> FEATURE:
<223> OTHER INFORMATION: Polypeptide Scaffold Loop Region

<400> SEQUENCE: 67

Gln Pro Thr Phe Met Pro Glu
1               5

<210> SEQ ID NO 68
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 68

Glu Trp Gln Val Asp Ala Glu
1               5

<210> SEQ ID NO 69
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 69

Met Glu Tyr Ser Trp Gln Tyr
1               5

<210> SEQ ID NO 70
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 70

Glu Arg Trp Ala Met Trp Tyr
1               5

<210> SEQ ID NO 71
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 71

Ala His Ala Trp Leu Pro Glu
1               5

<210> SEQ ID NO 72
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 72

Gln Glu Ala Ser Trp Leu Ser
1               5

<210> SEQ ID NO 73
<211> LENGTH: 7
<212> TYPE: PRT
```

```
<213> ORGANISM: Artificial
<220> FEATURE:
<223> OTHER INFORMATION: Polypeptide Scaffold Loop Region

<400> SEQUENCE: 73

Tyr Asp Glu Trp Phe Trp Thr
1               5

<210> SEQ ID NO 74
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 74

Arg Arg Phe Trp Pro Pro Phe
1               5

<210> SEQ ID NO 75
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 75

Ser Ser Thr Glu Trp Phe Val
1               5

<210> SEQ ID NO 76
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 76

Met Ile Pro Trp Met Val Pro Gly
1               5

<210> SEQ ID NO 77
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 77

Asp Trp Trp Trp Asp Thr Ile Glu
1               5

<210> SEQ ID NO 78
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 78

Pro Trp Asn Trp Val Asp Leu Thr
1               5

<210> SEQ ID NO 79
<211> LENGTH: 8
<212> TYPE: PRT
<213> ORGANISM: Artificial
```

```
<220> FEATURE:
<223> OTHER INFORMATION: Polypeptide Scaffold Loop Region

<400> SEQUENCE: 79

His Pro Trp Ile Lys Trp Tyr Trp
1               5

<210> SEQ ID NO 80
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 80

Trp His Pro Trp Phe Gln Tyr Glu
1               5

<210> SEQ ID NO 81
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 81

Trp Val Pro Glu Gln Phe Asp Gln
1               5

<210> SEQ ID NO 82
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 82

Asp Pro Trp Leu Met Pro Pro Ala
1               5

<210> SEQ ID NO 83
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 83

Thr Ala Thr Lys Ser Phe Trp Trp
1               5

<210> SEQ ID NO 84
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 84

Asp Ile Pro Lys Gln Trp Gly Lys
1               5

<210> SEQ ID NO 85
<211> LENGTH: 7
<212> TYPE: PRT
<213> ORGANISM: Artificial
<220> FEATURE:
```

```
<223> OTHER INFORMATION: Polypeptide Scaffold Loop Region

<400> SEQUENCE: 85

Thr Val His Ala Val Pro Thr
1               5

<210> SEQ ID NO 86
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 86

Ser Ala Asn Phe Pro Ser Val
1               5

<210> SEQ ID NO 87
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 87

Ala Asn Ala Pro Val Ala Thr
1               5

<210> SEQ ID NO 88
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 88

Ser Lys Ser Thr Phe His Val
1               5

<210> SEQ ID NO 89
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 89

Leu Ala Pro Leu Ser Val Val
1               5

<210> SEQ ID NO 90
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 90

Gln Phe Gln Tyr Pro Val Val
1               5

<210> SEQ ID NO 91
<211> LENGTH: 7
<212> TYPE: PRT
<213> ORGANISM: Artificial
<220> FEATURE:
<223> OTHER INFORMATION: Polypeptide Scaffold Loop Region
```

<400> SEQUENCE: 91

Ala Pro Pro Leu Asn Val Val
1               5

<210> SEQ ID NO 92
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 92

Ala Pro Ser Leu Pro Val Val
1               5

<210> SEQ ID NO 93
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 93

Phe Pro Ser Ser Leu Pro Val
1               5

<210> SEQ ID NO 94
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 94

Ser Thr Ser Pro Leu Pro Thr
1               5

<210> SEQ ID NO 95
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 95

Pro Pro Val Met Ser Pro Val
1               5

<210> SEQ ID NO 96
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 96

Leu Pro Pro Pro His Pro Leu
1               5

<210> SEQ ID NO 97
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 97

Tyr Val Thr Leu His Pro Val
1               5

<210> SEQ ID NO 98
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 98

Thr Leu Pro Met Leu Pro Thr
1               5

<210> SEQ ID NO 99
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 99

Asn Trp Arg Trp Val Met Glu Asp
1               5

<210> SEQ ID NO 100
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 100

Pro Ala Thr Gln His Pro Val
1               5

<210> SEQ ID NO 101
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 101

Leu Tyr Pro Leu Asp Gln Ser Ser
1               5

<210> SEQ ID NO 102
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 102

Asp Leu His Phe Tyr Val Val Ser
1               5

<210> SEQ ID NO 103
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 103

Leu Tyr Pro Met Gln Ala Ser Leu
1               5

<210> SEQ ID NO 104
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 104

Thr Ser Tyr Tyr Lys Lys Phe Pro
1               5

<210> SEQ ID NO 105
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 105

Leu Tyr Pro Tyr Pro Val Ala Ser
1               5

<210> SEQ ID NO 106
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 106

Ser Thr Tyr Pro Leu Leu Ile Phe
1               5

<210> SEQ ID NO 107
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 107

Leu Tyr Pro Lys Pro Glu Pro His
1               5

<210> SEQ ID NO 108
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 108

Leu Tyr Pro Phe Pro Thr Gln Asp
1               5

<210> SEQ ID NO 109
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 109

Leu Tyr Asn Pro Gln Tyr Met Tyr
1               5

<210> SEQ ID NO 110
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 110

Leu Tyr Pro Ser His Leu Ser Ser
1               5

<210> SEQ ID NO 111
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 111

Leu Tyr Pro Pro Ala Lys Val His
1               5

<210> SEQ ID NO 112
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 112

Leu Tyr Pro Tyr Pro Pro Ile Ser
1               5

<210> SEQ ID NO 113
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 113

Leu Tyr Pro Tyr Pro Thr His Leu
1               5

<210> SEQ ID NO 114
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 114

Leu Tyr Pro Tyr Pro Tyr Glu Tyr
1               5

<210> SEQ ID NO 115
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 115

Ser Ile His Met Gly Pro Arg Gly

```
<210> SEQ ID NO 116
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 116

Leu Tyr Pro Leu Pro Pro Leu Leu
1               5

<210> SEQ ID NO 117
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 117

Asp Ala His Ser Phe Thr Val
1               5

<210> SEQ ID NO 118
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 118

Pro Leu Tyr Gly Phe Gly Phe Met
1               5

<210> SEQ ID NO 119
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 119

Ala Gly Arg Thr Val Pro Gln
1               5

<210> SEQ ID NO 120
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 120

Trp Asp Trp Met Trp Pro Asn Met
1               5

<210> SEQ ID NO 121
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 121

Pro Leu Ser Pro Trp Gly Phe Gln
1               5
```

```
<210> SEQ ID NO 122
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 122

Pro Gly Asp Thr Trp Ala Ser
1               5

<210> SEQ ID NO 123
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 123

Asp Ile Gly Ala Phe Ala Ile Pro
1               5

<210> SEQ ID NO 124
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 124

Val Trp Thr Asn Val Asn Lys
1               5

<210> SEQ ID NO 125
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 125

Trp Trp Trp Leu Trp Pro Glu Gly
1               5

<210> SEQ ID NO 126
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 126

Tyr Arg Val Val His Gly Val
1               5

<210> SEQ ID NO 127
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 127

Phe Phe Trp Ser Trp Pro Lys Glu
1               5
```

```
<210> SEQ ID NO 128
<211> LENGTH: 6
<212> TYPE: PRT
<213> ORGANISM: Artificial
<220> FEATURE:
<223> OTHER INFORMATION: Polypeptide Scaffold Loop Region

<400> SEQUENCE: 128

Gln Pro Asp Arg Trp Ile
1               5

<210> SEQ ID NO 129
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 129

Asp Pro Trp His Met Met Phe Gln
1               5

<210> SEQ ID NO 130
<211> LENGTH: 54
<212> TYPE: DNA
<213> ORGANISM: Artificial
<220> FEATURE:
<223> OTHER INFORMATION: FNfn10 Scaffold BC1 Loop of Library 1

<400> SEQUENCE: 130
cgtgatacgg taataacgak makmakmakm akmakmakmc cagctgatca ggct          54

<210> SEQ ID NO 131
<211> LENGTH: 63
<212> TYPE: DNA
<213> ORGANISM: Artificial
<220> FEATURE:
<223> OTHER INFORMATION: FNfn10 Scaffold FG1 Loop of Library 1

<400> SEQUENCE: 131
aatcgagatt ggcttggaak makmakmakm akmakmakma kmagtaacag cgtatacagt    60
gat                                                                 63

<210> SEQ ID NO 132
<211> LENGTH: 54
<212> TYPE: DNA
<213> ORGANISM: Artificial
<220> FEATURE:
<223> OTHER INFORMATION: FNfn10 Scaffold BC2 Loop of Library 2
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
```

<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t

<400> SEQUENCE: 132
cgtgatacgg taataacgmd nmdnmdnmdn mdnmdnmdnc cagctgatca ggct        54

<210> SEQ ID NO 133
<211> LENGTH: 63
<212> TYPE: DNA
<213> ORGANISM: Artificial
<220> FEATURE:
<223> OTHER INFORMATION: FNfn10 Scaffold FG2 Loop of Library 2
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t
<220> FEATURE:
<221> NAME/KEY: misc_feature
<222> LOCATION: (39)..(39)
<223> OTHER INFORMATION: n is a, c, g, or t
<220> FEATURE:
<221> NAME/KEY: misc_feature
<222> LOCATION: (42)..(42)
<223> OTHER INFORMATION: n is a, c, g, or t

<400> SEQUENCE: 133
aatcgagatt ggcttggamd nmdnmdnmdn mdnmdnmdnm dnagtaacag cgtatacagt    60
gat        63

<210> SEQ ID NO 134
<211> LENGTH: 45
<212> TYPE: DNA
<213> ORGANISM: Artificial
<220> FEATURE:
<223> OTHER INFORMATION: FNfn10 Scaffold BC3 Loop of Library 3
<220> FEATURE:
<221> NAME/KEY: misc_feature
<222> LOCATION: (13)..(15)
<223> OTHER INFORMATION: N is A, T, C, or G and encodes any amino acid
      except Cys
<220> FEATURE:
<221> NAME/KEY: misc_feature
<222> LOCATION: (16)..(18)
<223> OTHER INFORMATION: N is A, T, C, or G and encodes any amino acid
      except Cys
<220> FEATURE:
<221> NAME/KEY: misc_feature
<222> LOCATION: (19)..(21)

```
<223> OTHER INFORMATION: N is A, T, C, or G and encodes any amino acid
      except Cys
<220> FEATURE:
<221> NAME/KEY: misc_feature
<222> LOCATION: (22)..(24)
<223> OTHER INFORMATION: N is A, T, C, or G and encodes any amino acid
      except Cys
<220> FEATURE:
<221> NAME/KEY: misc_feature
<222> LOCATION: (25)..(27)
<223> OTHER INFORMATION: N is A, T, C, or G and encodes any amino acid
      except Cys
<220> FEATURE:
<221> NAME/KEY: misc_feature
<222> LOCATION: (28)..(30)
<223> OTHER INFORMATION: N is A, T, C, or G and encodes any amino acid
      except Cys
<220> FEATURE:
<221> NAME/KEY: misc_feature
<222> LOCATION: (31)..(33)
<223> OTHER INFORMATION: N is A, T, C, or G and encodes any amino acid
      except Cys

<400> SEQUENCE: 134
ctgatcagct ggnnnnnnnn nnnnnnnnnn nnncgttatt accgt              45

<210> SEQ ID NO 135
<211> LENGTH: 48
<212> TYPE: DNA
<213> ORGANISM: Artificial
<220> FEATURE:
<223> OTHER INFORMATION: FNfn10 Scaffold FG3 Loop of Library 3
<220> FEATURE:
<221> NAME/KEY: misc_feature
<222> LOCATION: (13)..(15)
<223> OTHER INFORMATION: N is A, T, C, or G and encodes any amino acid
      except Cys
<220> FEATURE:
<221> NAME/KEY: misc_feature
<222> LOCATION: (16)..(18)
<223> OTHER INFORMATION: N is A, T, C, or G and encodes any amino acid
      except Cys
<220> FEATURE:
<221> NAME/KEY: misc_feature
<222> LOCATION: (19)..(21)
<223> OTHER INFORMATION: N is A, T, C, or G and encodes any amino acid
      except Cys
<220> FEATURE:
<221> NAME/KEY: misc_feature
<222> LOCATION: (22)..(24)
<223> OTHER INFORMATION: N is A, T, C, or G and encodes any amino acid
      except Cys
<220> FEATURE:
<221> NAME/KEY: misc_feature
<222> LOCATION: (25)..(27)
<223> OTHER INFORMATION: N is A, T, C, or G and encodes any amino acid
      except Cys
<220> FEATURE:
<221> NAME/KEY: misc_feature
<222> LOCATION: (28)..(30)
<223> OTHER INFORMATION: N is A, T, C, or G and encodes any amino acid
      except Cys
<220> FEATURE:
<221> NAME/KEY: misc_feature
<222> LOCATION: (31)..(33)
<223> OTHER INFORMATION: N is A, T, C, or G and encodes any amino acid
      except Cys
<220> FEATURE:
<221> NAME/KEY: misc_feature
<222> LOCATION: (34)..(36)
<223> OTHER INFORMATION: N is A, T, C, or G and encodes any amino acid
      except Cys

<400> SEQUENCE: 135
tacgctgtta ctnnnnnnnn nnnnnnnnnn nnnnnntcca agccaatc            48
```

```
<210> SEQ ID NO 136
<211> LENGTH: 45
<212> TYPE: DNA
<213> ORGANISM: Artificial
<220> FEATURE:
<223> OTHER INFORMATION: FNfn10 Scaffold BC4 Loop of Library 4
<220> FEATURE:
<221> NAME/KEY: misc_feature
<222> LOCATION: (13)..(15)
<223> OTHER INFORMATION: N is A, T, C, or G and encodes any amino acid
<220> FEATURE:
<221> NAME/KEY: misc_feature
<222> LOCATION: (16)..(18)
<223> OTHER INFORMATION: N is A, T, C, or G and encodes any amino acid
<220> FEATURE:
<221> NAME/KEY: misc_feature
<222> LOCATION: (19)..(21)
<223> OTHER INFORMATION: N is A, T, C, or G and encodes any amino acid
<220> FEATURE:
<221> NAME/KEY: misc_feature
<222> LOCATION: (22)..(24)
<223> OTHER INFORMATION: N is A, T, C, or G and encodes any amino acid
<220> FEATURE:
<221> NAME/KEY: misc_feature
<222> LOCATION: (25)..(27)
<223> OTHER INFORMATION: N is A, T, C, or G and encodes any amino acid
<220> FEATURE:
<221> NAME/KEY: misc_feature
<222> LOCATION: (28)..(30)
<223> OTHER INFORMATION: N is A, T, C, or G and encodes any amino acid

<400> SEQUENCE: 136
ctgatcagct ggnnnnnnnn nnnnnnnnnn tgtcgttatt accgt            45

<210> SEQ ID NO 137
<211> LENGTH: 48
<212> TYPE: DNA
<213> ORGANISM: Artificial
<220> FEATURE:
<223> OTHER INFORMATION: FNfn10 Scaffold FG4 Loop of Library 4
<220> FEATURE:
<221> NAME/KEY: misc_feature
<222> LOCATION: (16)..(18)
<223> OTHER INFORMATION: N is A, T, C, or G and encodes any amino acid
<220> FEATURE:
<221> NAME/KEY: misc_feature
<222> LOCATION: (19)..(21)
<223> OTHER INFORMATION: N is A, T, C, or G and encodes any amino acid
<220> FEATURE:
<221> NAME/KEY: misc_feature
<222> LOCATION: (22)..(24)
<223> OTHER INFORMATION: N is A, T, C, or G and encodes any amino acid
<220> FEATURE:
<221> NAME/KEY: misc_feature
<222> LOCATION: (25)..(27)
<223> OTHER INFORMATION: N is A, T, C, or G and encodes any amino acid
<220> FEATURE:
<221> NAME/KEY: misc_feature
<222> LOCATION: (28)..(30)
<223> OTHER INFORMATION: N is A, T, C, or G and encodes any amino acid
<220> FEATURE:
<221> NAME/KEY: misc_feature
<222> LOCATION: (31)..(33)
<223> OTHER INFORMATION: N is A, T, C, or G and encodes any amino acid
<220> FEATURE:
<221> NAME/KEY: misc_feature
<222> LOCATION: (34)..(36)
<223> OTHER INFORMATION: N is A, T, C, or G and encodes any amino acid

<400> SEQUENCE: 137
tacgctgtta cttgcnnnnn nnnnnnnnnn nnnnnntcca agccaatc         48

<210> SEQ ID NO 138
<211> LENGTH: 7
```

```
<212> TYPE: PRT
<213> ORGANISM: Artificial
<220> FEATURE:
<223> OTHER INFORMATION: Polypeptide Scaffold Loop Region

<400> SEQUENCE: 138

Pro Lys Leu Gly Val Asn Lys
1               5

<210> SEQ ID NO 139
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 139

Val Trp Glu Trp Asp Gln Pro Gln
1               5

<210> SEQ ID NO 140
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 140

Met His Gln Met Pro Trp Val
1               5

<210> SEQ ID NO 141
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 141

Tyr Trp Arg Thr Thr Pro Phe Met
1               5

<210> SEQ ID NO 142
<211> LENGTH: 23
<212> TYPE: PRT
<213> ORGANISM: Artificial
<220> FEATURE:
<223> OTHER INFORMATION: 2F5 peptide epitope

<400> SEQUENCE: 142

Cys Asn Glu Gln Glu Leu Leu Glu Leu Asp Lys Trp Ala Ser Leu Trp
1               5                   10                  15

Ser Gly Gly Arg Gly Gly Leu
            20

<210> SEQ ID NO 143
<211> LENGTH: 17
<212> TYPE: PRT
<213> ORGANISM: Artificial
<220> FEATURE:
<223> OTHER INFORMATION: 4E10 peptide epitope

<400> SEQUENCE: 143

Cys Ser Leu Trp Asn Trp Phe Asp Ile Thr Asn Trp Leu Trp Arg Arg
1               5                   10                  15

Lys
```

```
<210> SEQ ID NO 144
<211> LENGTH: 88
<212> TYPE: PRT
<213> ORGANISM: Human

<400> SEQUENCE: 144

Asp Ala Pro Ser Gln Ile Glu Val Lys Asp Val Thr Asp Thr Thr Ala
1               5                   10                  15

Leu Ile Thr Trp Phe Lys Pro Leu Ala Glu Ile Asp Gly Ile Glu Leu
            20                  25                  30

Thr Tyr Gly Ile Lys Asp Val Pro Gly Asp Arg Thr Thr Ile Asp Leu
        35                  40                  45

Thr Glu Asp Glu Asn Gln Tyr Ser Ile Gly Asn Leu Lys Pro Asp Thr
    50                  55                  60

Glu Tyr Glu Val Ser Leu Ile Ser Arg Arg Gly Asp Met Ser Ser Asn
65                  70                  75                  80

Pro Ala Lys Glu Thr Phe Thr Thr
                85

<210> SEQ ID NO 145
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 145

Ser Pro Pro Thr Phe Pro Met
1               5

<210> SEQ ID NO 146
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 146

Ser Leu Leu Asp Phe Pro Ile Val
1               5

<210> SEQ ID NO 147
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 147

Tyr Val Asn Ala Gln Val Val Phe
1               5

<210> SEQ ID NO 148
<211> LENGTH: 10
<212> TYPE: PRT
<213> ORGANISM: Artificial
<220> FEATURE:
<223> OTHER INFORMATION: Polypeptide Scaffold Loop Region

<400> SEQUENCE: 148

Ala Thr Glu Glu Leu His Val Val Ser Gln
1               5                   10
```

```
<210> SEQ ID NO 149
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 149

Leu Pro His Ala Pro Met Ala
1               5

<210> SEQ ID NO 150
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 150

Pro Phe Tyr Ser Phe Pro His Met
1               5

<210> SEQ ID NO 151
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 151

Met Pro Phe Val Phe Thr Pro
1               5

<210> SEQ ID NO 152
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 152

Ser Tyr Val Pro Phe Ala Asp Val
1               5

<210> SEQ ID NO 153
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 153

Leu His His Ser Pro Ser Ala
1               5

<210> SEQ ID NO 154
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 154

Leu Thr Leu Leu Pro Asn Tyr Val
1               5
```

```
<210> SEQ ID NO 155
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 155

His Ile Ser Phe Pro Tyr Thr
1               5

<210> SEQ ID NO 156
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 156

Ser Leu Phe Tyr Pro Val Pro Ser
1               5

<210> SEQ ID NO 157
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 157

Ala Thr Ser Leu Ser Thr Leu
1               5

<210> SEQ ID NO 158
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 158

Phe Pro Asn Tyr Ser Tyr Pro Leu
1               5

<210> SEQ ID NO 159
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 159

Ala Ser Ser Leu Pro Ser Leu
1               5

<210> SEQ ID NO 160
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 160

Phe Ala Pro Gln Leu His Thr Leu
1               5

<210> SEQ ID NO 161
```

```
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 161

Leu Gln Ser Ala Leu Phe Ala
1               5

<210> SEQ ID NO 162
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 162

Pro Tyr Phe Pro Ala Glu Phe Pro
1               5

<210> SEQ ID NO 163
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 163

Val Phe Trp Asp Gln Trp Thr
1               5

<210> SEQ ID NO 164
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 164

Trp Met Gln Trp Trp Glu Phe Gln
1               5

<210> SEQ ID NO 165
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 165

Gln Gln Pro Glu Asp Ala Ala Asp
1               5

<210> SEQ ID NO 166
<211> LENGTH: 7
<212> TYPE: PRT
<213> ORGANISM: Artificial
<220> FEATURE:
<223> OTHER INFORMATION: Polypeptide Scaffold Loop Region

<400> SEQUENCE: 166

Lys Ser Ser Glu Phe Tyr Pro
1               5

<210> SEQ ID NO 167
<211> LENGTH: 10
```

```
<212> TYPE: PRT
<213> ORGANISM: Artificial
<220> FEATURE:
<223> OTHER INFORMATION: Polypeptide Scaffold Loop Region

<400> SEQUENCE: 167

Leu Pro Ala Pro Met Glu Leu Lys Ser Pro
1               5                   10

<210> SEQ ID NO 168
<211> LENGTH: 8
<212> TYPE: PRT
<213> ORGANISM: Artificial
<220> FEATURE:
<223> OTHER INFORMATION: Polypeptide Scaffold Loop Region

<400> SEQUENCE: 168

Ser Phe Ser Ser Leu Phe Val Ser
1               5

<210> SEQ ID NO 169
<211> LENGTH: 89
<212> TYPE: PRT
<213> ORGANISM: Artificial
<220> FEATURE:
<223> OTHER INFORMATION: Consensus sequence of Tn3 domain of Tenascin C

<400> SEQUENCE: 169

Leu Pro Ala Pro Lys Asn Leu Val Val Ser Glu Val Thr Glu Asp Ser
1               5                   10                  15

Leu Arg Leu Ser Trp Thr Ala Pro Asp Ala Ala Phe Asp Ser Phe Leu
            20                  25                  30

Ile Gln Tyr Gln Glu Ser Glu Lys Val Gly Glu Ala Ile Asn Leu Thr
        35                  40                  45

Val Pro Gly Ser Glu Arg Ser Tyr Asp Leu Thr Gly Leu Lys Pro Gly
    50                  55                  60

Thr Glu Tyr Thr Val Ser Ile Tyr Gly Val Lys Gly Gly His Arg Ser
65                  70                  75                  80

Asn Pro Leu Ser Ala Glu Phe Thr Thr
                85
```